US008349793B2

(12) United States Patent
Braiman-Wiksman et al.

(10) Patent No.: US 8,349,793 B2
(45) Date of Patent: Jan. 8, 2013

(54) METHOD FOR TREATMENT OF INFLAMMATORY DISEASE AND DISORDER

(75) Inventors: Liora Braiman-Wiksman, Le-Zion (IL); Tamar Tennenbaum, Jerusalem (IL); Yuvai Sagiv, Gedera (IL); Marina Gartsbein, Tikva (IL); Ephraim Brener, Rishon Le Zion (IL); Moshe Ben-Hamo, Bene Braq (IL); Liat Hammer, Modiin (IL)

(73) Assignee: Heal0r, Ltd., Rehovot (IL)

( * ) Notice: Subject to any disclaimer, the term of this patent is extended or adjusted under 35 U.S.C. 154(b) by 0 days.

(21) Appl. No.: 13/181,687

(22) Filed: Jul. 13, 2011
(Under 37 CFR 1.47)

(65) Prior Publication Data

US 2012/0190611 A1 Jul. 26, 2012

Related U.S. Application Data

(63) Continuation-in-part of application No. PCT/IL2011/000032, filed on Jan. 11, 2011.

(60) Provisional application No. 61/293,794, filed on Jan. 11, 2010, provisional application No. 61/405,509, filed on Oct. 21, 2010.

(51) Int. Cl.
*A61K 38/08* (2006.01)

(52) U.S. Cl. ....... 514/1.7; 514/18.6; 514/18.7; 514/886; 514/887

(58) Field of Classification Search .................... 514/1.7, 514/18.6, 18.7, 886, 887
See application file for complete search history.

(56) References Cited

U.S. PATENT DOCUMENTS

| 3,549,747 A | 12/1970 | Krezanoski et al. |
| 3,767,788 A | 10/1973 | Rankin et al. |
| 3,767,789 A | 10/1973 | Rankin et al. |
| 3,856,919 A | 12/1974 | Rankin |
| 3,907,985 A | 9/1975 | Rankin |
| 3,920,810 A | 11/1975 | Rankin |
| 3,947,573 A | 3/1976 | Rankin |
| 3,987,163 A | 10/1976 | Rankin |
| 4,029,817 A | 6/1977 | Blanco et al. |
| 4,120,949 A | 10/1978 | Bapatla et al. |
| 4,131,651 A | 12/1978 | Shah et al. |
| 4,409,205 A | 10/1983 | Shively |
| 4,558,033 A | 12/1985 | Rudman |
| 4,673,649 A | 6/1987 | Boyce et al. |
| 4,808,402 A | 2/1989 | Leibovich et al. |
| 4,833,257 A | 5/1989 | Pettit et al. |
| 4,927,636 A | 5/1990 | Hijiya et al. |
| 4,940,660 A | 7/1990 | Hirai et al. |
| 5,019,400 A | 5/1991 | Gombotz et al. |
| 5,106,615 A | 4/1992 | Dickstein |
| 5,137,734 A | 8/1992 | Spiegelman et al. |
| 5,145,679 A | 9/1992 | Hinson |
| 5,158,935 A | 10/1992 | Nascimento et al. |
| 5,444,041 A | 8/1995 | Owen et al. |
| 5,461,030 A | 10/1995 | Lindenbaum |
| 5,591,426 A | 1/1997 | Dabrowski et al. |
| 5,591,709 A | 1/1997 | Lindenbaum |
| 5,603,943 A | 2/1997 | Yanagawa |
| 5,631,245 A | 5/1997 | Drube |
| 5,723,119 A | 3/1998 | Schwartz et al. |
| 5,770,228 A | 6/1998 | Edwards et al. |
| 5,830,507 A | 11/1998 | Armstrong |
| 5,869,037 A | 2/1999 | Crystal et al. |
| 5,942,487 A | 8/1999 | Ogawa et al. |
| 5,981,606 A | 11/1999 | Martin |
| 6,028,118 A | 2/2000 | Dupont et al. |
| 6,096,288 A | 8/2000 | Roth |
| 6,174,856 B1 | 1/2001 | Langballe et al. |
| 6,274,712 B1 | 8/2001 | Springer et al. |
| 6,319,907 B1 | 11/2001 | Ferguson |
| 6,403,656 B1 | 6/2002 | River et al. |
| 6,485,721 B1 | 11/2002 | Yoshida et al. |
| 6,489,306 B2 | 12/2002 | Mohapatra et al. |
| 6,537,973 B1 | 3/2003 | Bennett et al. |
| 6,541,447 B1 | 4/2003 | Dawson |
| 6,582,713 B2 | 6/2003 | Newell et al. |
| 6,686,334 B2 | 2/2004 | Messing et al. |
| 6,737,241 B2 | 5/2004 | Nolan et al. |
| 6,841,472 B2 | 1/2005 | Mayuzumi |
| 7,074,408 B2 | 7/2006 | Fanslow et al. |
| 7,261,881 B1 | 8/2007 | Sierra-Honigmann |
| 7,402,571 B2 | 7/2008 | Tennenbaum et al. |
| 7,638,484 B2 | 12/2009 | Braiman-Wiksman et al. |
| 2001/0036955 A1 | 11/2001 | Gerritsen et al. |
| 2002/0119914 A1 | 8/2002 | Zhu et al. |
| 2003/0124503 A1 | 7/2003 | Olivencia-Yurvati |
| 2003/0147855 A1 | 8/2003 | Zolotukhin et al. |
| 2003/0148924 A1 | 8/2003 | Tennenbaum et al. |

(Continued)

FOREIGN PATENT DOCUMENTS

EP 0 280 460 8/1988

(Continued)

OTHER PUBLICATIONS

Turban, et al. "Protein kinase C isoforms: Mediators of reactive lipid metabolites in the development of insulin resistance", *J. FEBS Letters* 585 (2011), pp. 269-274.

Dulbecco, et al. "Plaque formation and isolation of pure lines with poliomyelitis viruses", *J. Exp. Med.* 99(2), (1954), pp. 167-182.

Višnjić, et al. "Different roles of protein kinase C and isoforms in the regulation of neutral sphingomyelinase activity in HL-60 cells", *Biochem. J.* 344, (1999), pp. 921-928.

Ai, et al. "The experimental study of bone marrow mesenchymal stem cells on the repair of skin wound combined with local radiation injury", *Zhonhghua Yi Xue Za Zhi*, 82(23), (2002), pp. 1632-1636; Pubmed Abstract PMID 12667374.

Aldhahi, et al. "Adipokines, Inflammation, and the Endothelium in Diabetes", *Current Diabetes Reports*, 3 (2003), pp. 293-298.

(Continued)

*Primary Examiner* — Cecilia J Tsang
*Assistant Examiner* — Kristina M Hellman
(74) *Attorney, Agent, or Firm* — Fulbright & Jaworski LLP

(57) ABSTRACT

The present disclosure provides a method, composition and kit for treatment of inflammatory disease and disorder using PKC isoform modulators. Exemplary modulators include inhibitors of PKC-alpha, PKC-epsilon and PKC-eta, as well as activators of PKC-delta.

8 Claims, 51 Drawing Sheets

U.S. PATENT DOCUMENTS

| | | |
|---|---|---|
| 2004/0037828 A1 | 2/2004 | Tennenbaum et al. |
| 2004/0116499 A1 | 6/2004 | Mayser et al. |
| 2004/0175384 A1 | 9/2004 | Mohapatra et al. |
| 2005/0054608 A1 | 3/2005 | Linge et al. |
| 2006/0177418 A1 | 8/2006 | Braiman-Wiksman et al. |
| 2006/0177443 A1 | 8/2006 | Fanslow et al. |
| 2006/0258562 A1 | 11/2006 | Tennenbaum |
| 2008/0159978 A1 | 7/2008 | Braiman-Wiksman et al. |
| 2008/0182780 A1 | 7/2008 | Linge et al. |
| 2008/0280816 A1 | 11/2008 | Tennenbaum et al. |
| 2009/0042803 A1 | 2/2009 | Terreux et al. |
| 2010/0092452 A1 | 4/2010 | Sullivan et al. |
| 2010/0129332 A1 | 5/2010 | Tennenbaum et al. |
| 2010/0167987 A9 | 7/2010 | Tennenbaum et al. |
| 2010/0215634 A1 | 8/2010 | Tennenbaum et al. |
| 2010/0310542 A1 | 12/2010 | Tennenbaum et al. |
| 2011/0021422 A1 | 1/2011 | Tennenbaum et al. |

FOREIGN PATENT DOCUMENTS

| | | |
|---|---|---|
| EP | 0 508 792 A1 | 10/1992 |
| EP | 0 561 330 | 9/1993 |
| EP | 0 679 402 | 2/1995 |
| EP | 2404928 A1 * | 1/2012 |
| GB | 2 369 572 | 6/2002 |
| JP | 63-303929 | 12/1988 |
| JP | 05-043453 | 2/1993 |
| JP | 06-510453 | 11/1994 |
| JP | 07-316066 | 12/1995 |
| JP | 08-003067 | 1/1996 |
| JP | 10-265405 | 10/1998 |
| JP | 2002-272831 | 9/2002 |
| RU | 2104935 | 2/1998 |
| RU | 211 54 10 | 7/1998 |
| RU | 2161489 | 1/2001 |
| RU | 2 249 467 C2 | 4/2005 |
| WO | WO 85/05036 | 11/1985 |
| WO | WO 89/10129 A1 | 11/1989 |
| WO | WO 90/11071 A1 | 10/1990 |
| WO | WO 90/11075 | 10/1990 |
| WO | WO 92/18147 | 10/1992 |
| WO | WO 93/04691 A | 3/1993 |
| WO | WO 93/25660 A1 | 12/1993 |
| WO | WO 96/09810 | 4/1996 |
| WO | WO 96/20724 | 7/1996 |
| WO | WO 96/23522 | 8/1996 |
| WO | WO 99/18920 | 4/1999 |
| WO | WO 99/34821 | 7/1999 |
| WO | WO 99/35283 | 7/1999 |
| WO | WO 99/53943 | 10/1999 |
| WO | WO 00/30628 A2 | 6/2000 |
| WO | WO 01/07910 A1 | 2/2001 |
| WO | WO 0171042 A2 * | 9/2001 |
| WO | WO 01/76650 | 10/2001 |
| WO | WO 02/09639 A2 | 2/2002 |
| WO | WO 02/17980 A2 | 3/2002 |
| WO | WO 02/43751 | 6/2002 |
| WO | WO 02/066067 A2 | 8/2002 |
| WO | WO 02/072092 A1 | 9/2002 |
| WO | WO 02/087576 A1 | 11/2002 |
| WO | WO 02/094877 A2 | 11/2002 |
| WO | 03/002154 A1 | 1/2003 |
| WO | WO 2005/007072 A2 | 1/2005 |
| WO | WO 2005/009437 A1 | 2/2005 |
| WO | WO 2005/013885 A2 | 2/2005 |
| WO | WO 2005/025602 A1 | 3/2005 |
| WO | WO 2006014579 A2 * | 2/2006 |
| WO | WO 2007/026356 A2 | 3/2007 |
| WO | WO 2007/075911 A2 | 7/2007 |
| WO | WO 2009/016629 A2 | 5/2009 |
| WO | WO 2009097133 A2 * | 8/2009 |
| WO | WO 2010/097788 A9 | 9/2010 |
| WO | WO 2011/0083482 A2 | 7/2011 |
| WO | WO 2011/0083483 A2 | 7/2011 |

OTHER PUBLICATIONS

Alessenko, et al. "Selective changes in protein kinase C isoenzymes in rat liver nuclei during liver regeneration", *Biochem. Biophys, Commun.*, 182, (1992), pp. 1333-1339.

Andre, et al. "Protein kinases C-gamma and -delta are involved in insulin-like growth factor I-Induced migration of colonic epithelial cells", *Gastroent.* 116(1) (1999), pp. 64-77.

Anonymous "Dulbecco's Phosphate Buffered Saline (D-PBS)", Internet Article Abstact from URL:http://www.hyclone.com/media/dulbeccos_phosphate.htm>, accessed Mar. 3, 2009.

Ao, et al. "External application of insulin ointment to incurable skin ulcers", *J. Okayama Saiseikai Hen. Hosp.* 15 (1983), pp. 67-72 [English abstract only].

Aris, et al. "Molecular and biochemical characterization of a recombinant human PKC-delta family member", Database on NCBI.nlm.nih.gov, Genbank Accession No. L07860, Nov. 2, 1993.

Badiavas, et al. "Treatment of Chronic Wounds With Bone Marrow-Derived Cells", *Arch Dermatol.*, 139 (2003), pp. 510-516.

Bajou, et al. "Absence of host plasminogen activator inhibitor 1 prevents cancer invasion and vascularization", *Nat. Med.*, 4 (1998), pp. 923-928.

Bandyopadhyay, et al. "Effects of transienly expressed atypical ($\xi$, $\lambda$), conventional ($\alpha$, $\beta$) and novel ($\delta$, $\epsilon$) [..]", *Biochem. J.*, 337 (1999), pp. 461-470.

Belfield, et al.: "The use of insulin in open-wound healing", from a paper presented a $81^{st}$ Annual Convention of the California Veterinary Medical Association, Oct. 3, 1969.

Benes, et al. "The C2 domain of PKC $\delta$ is a phosphotyrosine binding domain", *Cell*, 121 (2005), pp. 271-280.

Bitar, et al. "Insulin and glucocorticoid-dependent suppression of the IGF-I system I diabetic wounds", *Surgery*, 127(6) (2000), pp. 687-695.

Boorsma, et al. "IP-10 mRNA expression in cultured keratinocytes is suppressed by inhibition of protein kinase-C and tyrosine and elevation of cAMP", *Cytokine*, 11(7) (1999), pp. 469-475, Abstract.

Braiman, et al. "Tyrosine phosphorylation pf specific protein kinase C izoenzymes participates in insulin stimulation of glucose transport in primary cultures of rat skeletal muscle", *Diaetes*, 48(10) (1999), pp. 1922-1929.

Braiman, et al. "Protein Kinase C$\delta$ Mediates Insulin-Induced Glucose Transport in Primary Cultures of Rat Skeletal Muscle", *Endocrin.*, 13(12), pp. 2002-2012.

Braiman-Wiksman, et al. "Novel Insights into Wound Healing Sequence of Events", *Toxicologic Pathology*, GB, vol. 35, No. 6, (2007), pp. 767-779.

Castellot: "Blood Vessel Formation During Wound Healing", Report, Tufts University, Boston, MA, 1995.

Chida, et al. "The $\eta$ isoform of protein kinase C is localized on rough endoplasmic reticulum", *Mol. Cell Biol.* 14 (1994), pp. 3782-3790.

Cordeiro "Beyond mitomycin: TGF-$\beta$ and wound healing", *Progress and Eye Res.* 21 (2002) 75-89.

Di Peppe, et al. "Adenovirus-mediated $VEGF_{165}$ gene transfer enhances wound healing by promoting angiogenesis in CD1 diabetic mice", *Gene Therapy* 9 (2002), pp. 1271-1277.

Dobson, et al. "1-Butyryl-Glycerol: A Novel Angiogenesis Factor Secreted by Differentiating Adipocytes", *Cell*, 61 (1990), pp. 223-230.

Dulbecco's Phosphate Buffered Saline (D-PBS), hy-Clone Media; XP-002520219.

Ferber, et al. "Pancreatic and duodenal homeobox gene 1 induces expression of insulin genes in liver and amellorates [..]", *Nature Med.* 6(5) (2000) pp. 568-572.

Finck et al.: "Tumor necrosis factor (TNF)-$\alpha$ induces leptin production through th e p55 TNF receptor", *Am.J.Physiol. Regulatory Comp. Physiol.* 278 (2000), pp. R537-R543.

Formisano, et al. "In NIH-3T3 fibroblasts, insulin receptor interaction with specific protein kinase C isoforms controls receptors intracellular routing", *J. Biol, Chem.*, 273 (1998), pp. 12197-13202.

Frank, et al. "Leptin enhances wound re-epithelialization and constitutes a direct function of leptin in skin repair", *J. Clin. Investigation*, 2000, vol. 106, pp. 501-509.

Gallucci, et al. "Interleukin-6 Treatment Augments Cutaneous Wound Healing in Immunosuppressed Mice", *J.Interf. Citokine Res.*, 21 (2001) pp. 603-609.

Gsshwendt "Protein kinase C$\delta$", *Eur. J. Biochem.*, 259 (1999), pp. 555-564.

Glatiramer atsetat. http://www.risnet.ru/mnn_qlatirameraatsetat.html, revised 2010.
Graham, et al. "Protein Kinase C Regulation of Corneal Endothelial Cell Proliferation and Cell Cycle", *Invest. Ophtalmol. & Visual Sci.*, 41 (2000) No. 13, pp. 4124-4132.
Greenway, et al.: "Topical insulin in wound healing: a randomised, double-blind, placebo-controlled trial", *J. Wound Care*, vol. 8, No. 10 (1999) pp. 526-528.
Hengge, et al. "Epidemis as target for in vivo gene-therapy", *J. Invest. Dermatol.* 105(3) (1995) p. 448.
Hofmann "The potential for isoenzyme-selective modulation of protein kinase C", *The FASEB J.*, 11 (1997), pp. 649-669.
Hussain, et al. "Identification and Characterization of Novel Lipophilic Antimicrobial Peptides Derived from Naturally Occurring Proteins", *Int'l J. Peptide Res. Ther.*, vol. 12, No. 3 (2006), pp. 269-273.
http://www.drugs.com/pdr/lletin_ll.html Information for patient Aug. 4, 2006.
Jameson, et al. "A role for skin gammadelta T cells in wound repair", *Sci.*, 296 (5568) (2002) pp. 747-749. Abstract.
Jeschke, et al. "IGF-I gene transfer in thermally injured rats", *Gene Ther.*, 6(6) (1999), pp. 1015-1020.
Jeschke, et al. "Effect of multiple gene transfer of insulinlike growth factor I complementary DNA gene constructs in rats after thermal injury", *Arch. Surg.*, 134(10) (1999), pp. 1137-1141.
Jones, et al. "Staurosporine, a non-specific PKC inhibitor, induces keratinocyte differentiation and raises intracellular calcium, but Ro31-8220, a specific inhibitor does not", *J. of Cell. Physiol.*, vol. 159, No. 2, (1994), pp. 324-330; Abstract XP-002520100, Database EMBASE [Online], Elsevier Science Publishers, Amsterdam, NL (1994).
Kirton: Presentation at Symposium Keloids and Hypertrophic Scars, Grand Rounds, Oct. 1999; http://www.uic.edu/depts/doms/rounds/rounds-35.html.
Kusunoki, et al. "A case of diabetic foot gangrene effectively treated by local injection of insulin" *J. of Aichi Med. Univ. Assoc.* 15 (1987), pp. 597-603 [English abstract only].
Leesnitzer, et al., "Functional Consequences of Cysteine Modification in the Ligand Binding Sites of Peroxisome Proliferator Activated Receptors by GW9662", *Biochem.* 41 (2002), pp. 6640-6650.
Lesion definition: http://216.251.232.159/semdweb/internetsornd/ASP/1533197.asp Jun. 23, 2005.
Liao, et al. "Effect of α-Protein Kinase C Neutralizing Antibodies and the Pseudosubstrate Peptide on Phosphorylation, Migration, and Growth of REF52 Cells", *Cell Growth and Differentiation*, vol. 4, No. 4, (1993), pp. 309-316.
Lindenbaum, et al. "Serum-free cell culture medium induces acceleration of wound heating in guinea-pigs", *Burns*, 21(2) (1995), pp. 110-115.
MacFarlane, et al. "Glucose stimulates translocation of the homeodomain of transcription factor PDX1 from the cytoplasm to the nucleus of pancreatic bet-cells", *J. Biol. Chem.*, 274(2), (1999), pp. 1001-1016.
Madibally, et al. "Influence of insulin therapy on burn wound healing in rats", *J. Surg. Res.*, 109 (2003), pp. 92-100.
Michalik, et al. "Impaired skin wound healing in perioxisome proliferator-activated receptor (PRAR) and PPAR mutant mice", *J. Cell. Biol.*, (154) (2001) pp. 799-814.
Mischak, et al. "Phorbol ester—induced myeloid differentiation is mediated by protein kinase C-α and -δ and not by protein kinase C-βII, -ε, -ξ, and -η", *J. Biol. Chem.*, 268 (1993), pp. 20110-20115.
Mischak, et al. "Overexpression of Protein Kinase C-δ and -ε in NIH 3T3 Cells Induces Opposite Effects [..]", *J. Biol. Chem.*, 268(9), (1993), pp. 6090-6096.
Mooney, et al. "Tumor necrosis factor and wound healing", *Annals of Surgery*, 211 (2), (1990) pp. 124-129.
Nishizuka: "The molecular heterogeneity of protein kinase C and its implications for cellular regulation", *Nature* vol. 334 (1988), No. 6184, pp. 661-665.
Ohba, et al. "Induction of differentiation in normal human keratinocytes by adenovirus-mediated introduction [..]", *Mol. Cel. Biol.*, 18(9)(1998), pp. 5199-5207.
Orgill, et al. <<Design of an artificial skin. IV. Use of island graft to isolate organ regeneration from scar synthesis and other processes leading to skin wound closure., *J. BiomedMater Res.* 39 (1998), p. 531-5, Abstract.
Osada, et al. "A phorbol ester receptor/protein kinase [..]", *J. Biol. Chem.*, 265 (1990), pp. 22434-22440.
Papp, et al. "Protein kinase C isozymes regulate proliferation and high cell density-mediated differentiation in HaCaT keratinocytes", *Experim. Dermatol.*, GB, vol. 12, No. 6, (2003) pp. 811-824.
Pellegrini, et al. "Cultivation of human keratinocyte stem, cells: current and future clinical applications", *Med. Biol. Eng. Comp.* 36(6), (1998), pp. 778-790.
Perletti, et al. "Protein Kinase Cε is oncogenic in colon epithelial cells by interaction with the *ras* signal transduction pathway", *Oncogene* 16(1998), pp. 3345-3348.
Pierre, et al. "Effects of Insulin on Wound Healing", *J. of Trauma*, US, vol. 44, No. 2 (1998), pp. 342-345.
Pittelkow, et al. "Serum-free culture of normal human melanocytes: growth kinetics and growth factor requirements", *J. Cel. Physiol.*, 140(3) (1989), pp. 565-576.
Rangwala and Lazar "Adipogenic transcriptional regulation", *Annu. Rev. Nutr.*, (20) (2000), pp. 535-559.
Reynolds, et al. "Down-regulation of langerhans cell protein kinase C-beta isoenzyme expression in inflammatory and hyperplastic dermatoses", *Br. J. Dermatol.*, 133(2), (1995), pp. 157-167 [PMED Abstract 7547380].
Reynolds, et al. "SCH 47112, a novel staurosporine derivative, inhibits 12-O-tetradecanoylphorbol-13-acetate-induced inflammation and epidermal hyperplasia in hairless mouse skin", *Arch. Dermatol. Res.*, 287 (1997), pp. 540-546.
Ring, et al. "Systematically and topically administered leptin both accelerate wound healing in diabetic *ob/ob* mice", *Endocrin.*, 141(1), (2000), pp. 446-449.
Servold, et al., "Growth factor impact on wound healing", *Clinics in Pod. Med. Surg.*, 8(4), (1991), pp. 937-953.
Setoguchi, et al. "Ex vivo and in vivo gene transfer to the skin using replication-deficient recombinant adenovirus vectors", *J. Invest Dermatol.* 102(4) (1994) pp. 415-421.
Shen, et al., "Protein Kinase C activation: a divergence point in the signaling of insulin and insulin like growth factor-1 induced proliferation of skin keratinocytes", Bar Ilan Univ., Ramat Gan, Israel (Abstract).
Shen, et al. "A Divergence Point in the Signaling of Insulin and IGF-1-Induced Proliferation of Skin Keratinocytes", *Diabetes*, US, vol. 50, No. 2 (2001), pp. 255-264.
Smith, et al. "Peroxisomes in Dermatology. Part II", *J. Cutaneous Med. Surg.* 5 (2001) pp. 315-322.
Soltoff and Toker "Carbachol, substance P, and phorbol ester promote the tyrosine phosphorylation of protein kinase Cδ in salivary gland epithelial cells", *J. Biol. Chem.*, 270 (1995), pp. 13490-13495.
Spravchikov, et al., "The interactive effects of hyperglycemia, insulin and IGF-1 in murine skin cells—an IR-null mouse model", Dept. of Pathol., Sackler School of Medicine, Tel Aviv Univ., Israel (Abstract).
Spravchikov, et al., "Glucose effects on skin keratinocytes: implications for diabetes skin complications", *Diabetes*, 50(7) (2001), pp. 1627-1635.
Stanwell, et al. "Staurosporine induces a complete program of terminal differentiation in neoplastic mouse keratinocytes via activation of protein kinase C", *Carcinogenesis*, GB, (1996), vol. 17, No. 6, pp. 1259-1265.
Sun, et al. "Squamous metaplasia of normal and carcinoma in situ of HPV 16-immortalized human endocervical cells", *Cancer Res.*, 52 (1992), pp. 4254-4260.
Taran, et al. "Improved vitality of experimental random dorsal skin flaps in rats treated with enriched cell culture medium", *Plast. Reconstr. Surg.*, 104(1)(1999), pp. 148-151.
Tennenbaum, et al. "Selective changes in laminin adhesion and $\alpha_6 \beta_4$ integrin regulaion are associated with the initial steps in keratinocyte maturation", *Cell Growth Differ.*, 7 (1996), pp. 615-628.
Traverso, et al. "Immunological evidence for increased oxidative stress in diabetic rats", *Diabetologia* (1998) 41: 265-170.

Varker, et al. "Involvement of the muscarinic acetylcholine receptor in inhibition of cell migration", *Biochem. Pharmocol.*, US, vol. 63, No. 4, (2002), pp. 597-605.

Volevodz, et al. "STH and IGF-I in case of diabetes mellitus: their role in pathogenesis of microvascular complications" (2000) http://www.diabet.ru/Sdiabet/2000-01/2000-01-13.htm.

Wallis, et al. "The α Isoform of Protein Kinase C is Involved in Signaling the Response of Desmosomes to Wounding in Cultured Epithelial Cells", *Molecular Biol. of the Cell*, US, vol. 11, No. 3, (2000), pp. 1077-1092.

Wang, et al. "Differential localization of protein kinase C δ by phorbol esters and related compounds using a fusion protein with green fluorescent protein", *J. Biol. Chem.*, 274 (1999), pp. 37233-37239.

Wertheimer, et al., "The effects of insulin signaling on skin proliferation and differentiation—lessons from the IR- and IRS1 Null Models", Dept. of Pathol., Sackler School of Medicine, Tel Aviv Univ., Israel (Abstract).

Wertheimer, et al. "Differential roles of insulin receptor and insulin-like growth factor-1 receptor I differentiation of murine skin keratinocytes", *J. Invest. Dermatol.*, (2000), pp. 24-29.

Wertheimer, et al. "The regulation of skin proliferation and differentiation in the IR null mouse: implications for skin complications of diabetes", *Endocrin.*, 142(3) (2001), pp. 1234-1241.

Yoshida, et al. "Topical application of insulin ointment to diabetic aging skin", IRYO 39 (1985), No. 2, pp. 147-150.

Yuli "Innovative PKC modulating formulation dramatically improves the healing of diabetic wounds", *J. Investigative Dermat.* Abstract 290, XP009121582, p. A49, vol. 122, No. 3 (2004).

Yuspa, et al. "Expression of Murine Epidermal Differentiation Markers Is Tightly Regulated by Restricted Extacellular Calcium Concentrations In Vitro", *J. of Cell Biol.*, US, vol. 109, No. 3, (1989), pp. 1207-1217.

Yuspa "The pathogenesis of squamous cell cancer: lessons learned from studies of carcinogenesis", *Cancer Res.*, 54 (1994), pp. 1178-1189.

Skvara, et al. "The PKC inhibitor AEB071 may be a therapeutic option for psoriasis", *J. Clin. Investigation*, 118 No. 9 (2008), pp. 3151-3159.

Cataisson, et al. "Activation of Cutaneous Protein Kinase Cα Induces Keratinocyte Apoptosis and Intraepidermal Inflammation by Independent Signaling Pathways", *J. of Immunol.*, US, vol. 171, No. 5, (2003), pp. 2703-2713.

Cataisson, et al. "Protein Kinase Cα—Mediated Chemotaxis of Neutrophils Requires NF-κB Activity but Is Independent of TNFα Signaling in Mouse Skin iln Vivo[1] ", *J. Immunol.* 174 (2005), pp. 1686-1692.

Denning, Mitchell "Epidermal keratinocytes: regulation of multiple cell phenotypes by multiple protein kinase C isoforms", *Int. J. Biochem. & Cell Biol.* 36 (2004), pp. 1141-1146.

Denning, et al. "Specific protein kinase C isozymes mediate the induction of keratinocyte differentiation markers by calcium", *Cell Growth Differ.*, 6 (1995), pp. 149-157.

Deucher, et al. "Calcium-dependent Involucrin Expression Is Inversely Regulated by Protein Kinase C (PKC)α and PKCδ", *J. Biol. Chem.* 277 No. 19 (2002), pp. 17032-17040.

Dlugosz and Yuspa "Coordinate changes in gene expression which mark the spinous to granular call transition in epidermis are regulated by protein kinase C", *J. Cell Biol.*, 120 (1993), pp. 217-225.

Fitch, et al. "Pathophysiology of Psoriasis: Resent Advances on IL-23 and Th17 Cytokines", *Curr. Rheumatol. Rep.* 9(6)(2007), pp. 461-467.

Frank, et al. "Interleukin-2 Therapy in Patients with HIV Infection", *N. Engl. J. Med.*, 361 (2009), pp. 1548-1559.

Hafler, et al. "Multiple sclerosis", *Immunol. Rev.* 204 (2005), pp. 208-231.

Jansen, et al. "Relation of the Induction of Epidermal Ornithine Decarboxylase and Hyperplasia to the Different Skin Tumor-Promotion Susceptibilities of Protein Kinase Cα, -δ and -ε Transgenic Mice", *Int. J. Cancer*, 93 (2001), pp. 635-643.

Lee, et al. "Differentiation of Cultured Human Epidermal Keratinocytes at High Cell Densities is Mediated by Endogenous Activation of the Protein Kinase C Signaling Pathway", *The Soc. for Investigative Dermatology, Inc.* 1998, pp. 762-766.

Matsui, et al. "Protein Kinase C in Normal Human Epidermal Keratinocytes During Proliferation and Calcium-Induced Differentiation", *The Soc. for Investigative Dermatology, Inc.* 1992, pp. 565-571.

Ng, et al. "PKCα regulates β1 integrin-dependent cell motility through association and control of integrin traffic", *EMBRO J.* 18(14) (1999),pp. 3909-3923.

Punnonen, et al "Keratinocyte Differentiation Is Associated with Changes in the Expression and Regulation of Phospholipase C Isoenzumes", *The Soc. for Investigative Dermatology, Inc.* 1993, pp. 719-726.

Tennenbaum, et al. "The Suprabasal Expression of α6β4 Integrin Is Associated with a High Risk for Malignant Progression in Mouse Skin Carcinogenesis", *Cancer Res.* 53 (1993), pp. 4803-4810.

Tibudan, et al. "Activation of Protein Kinase C triggers Irreversible Cell Cycle Withdrawal I Human Keratinocytes", *The Soc. for Investigative Dermatology, Inc.* 2002, pp. 1282-1289.

Tomakidi, et al. "Discriminating expression of differentiation markers evolves in transplants of benign and malignant human skin keratinocytes through stromal interactions", *J. Pathol.*, 200 (2003), pp. 298-307.

Yang, et al. "Role of Protein Kinase C α in Clcium Induced Keratinocyte Differentiation: Defective Regulation in Squamous Cell Carcinoma", *J. Cell. Physiol.*, 195 (2003), pp. 249-259.

Wang, et al. "Overexpression of protein kinase C-α in the epidermis of transgenic mice results in striking alterations in phorbol ester-induced inflammation and COX-2, MIP-2 and TXF-α expression but not tumor promotion", *J. Cell Sci.*, 112 (1999), pp. 3497-3506.

Wang, et al. "Further identification of protein kinase C isozymes in mouse epidermis", *J. cancer Res. Clin. Oncol.*, 119 (1993) pp. 279-287 [Abstract].

Eichholtz, et al. "A Myristoylated Pseudosubstrate Peptide, a Novel Protein Kinase C Inhibitor", *J. Biol. Chem.* 268, No. 3 (1993), pp. 1982-1986.

Braiman-Wiksman, et al. "Adipocytes and adiponectin secretion plays a major role in skin physiology and in diabetes wound healing pathology", *J. Investig. Dermatol.* 130 (1) (2010), p. S99, Abstract XP009158112.

Ellis, et al. "Troglitazone Improves Psoriasis and Normalizes Models of Proliferative Skin Disease", *Arch. Dermatol.* 136(5) (2000), pp. 609-616.

Ferringer, et al. "Cutaneous manifestations of diabetes mellitus", *Dermatol. Clin.* 20 (2002), pp. 483-492.

Mandil-Levin, et al., "New role for adipose tissue is skin physiology and wound healing", *J. Investig. Dermatol.* 126 (1) (2006), Abstract XP009158113.

Michalik, et al. "Peroxisome proliferator-activated receptors (PPARs) in skin health, repair and disease", *Biochimica et Biophysica Acta*, Elsevier, NL, 1771 No. 8 (2007), pp. 991-998.

\* cited by examiner

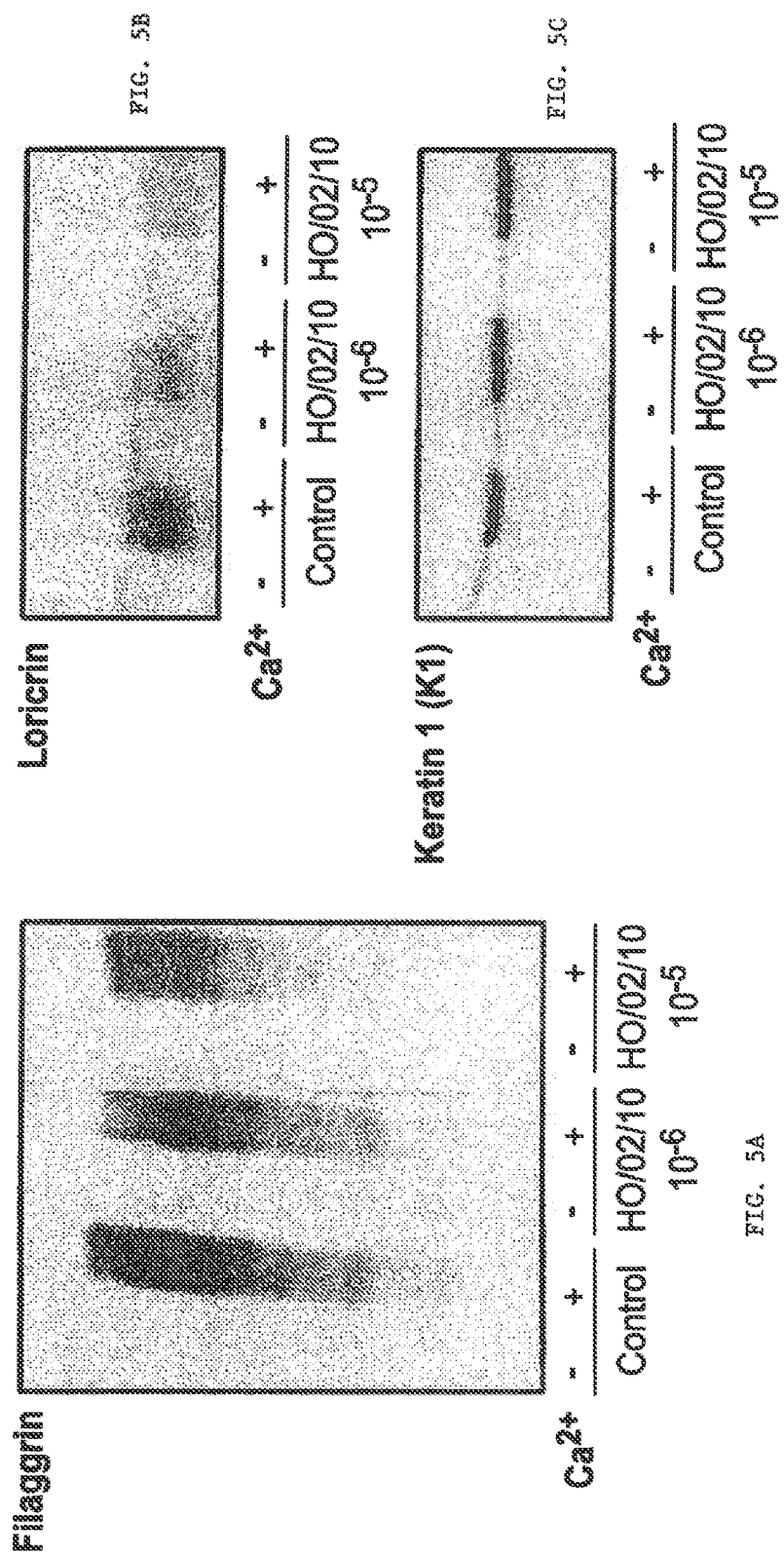

Untreated Control

1. Keratinocytes

2. Endothelium

HO/02/10 treated

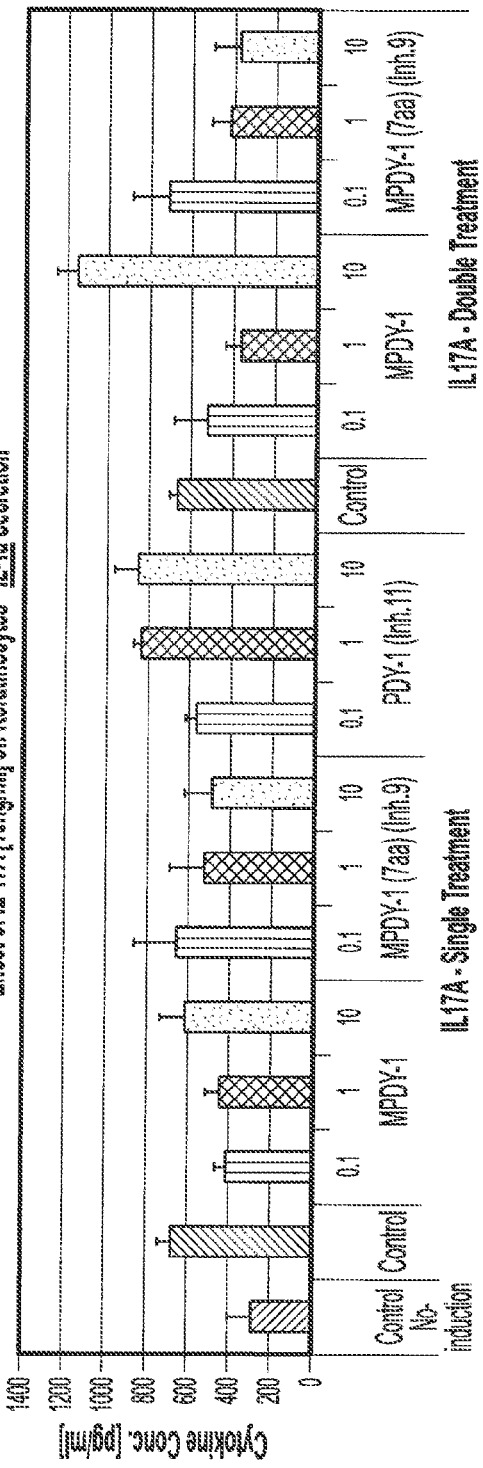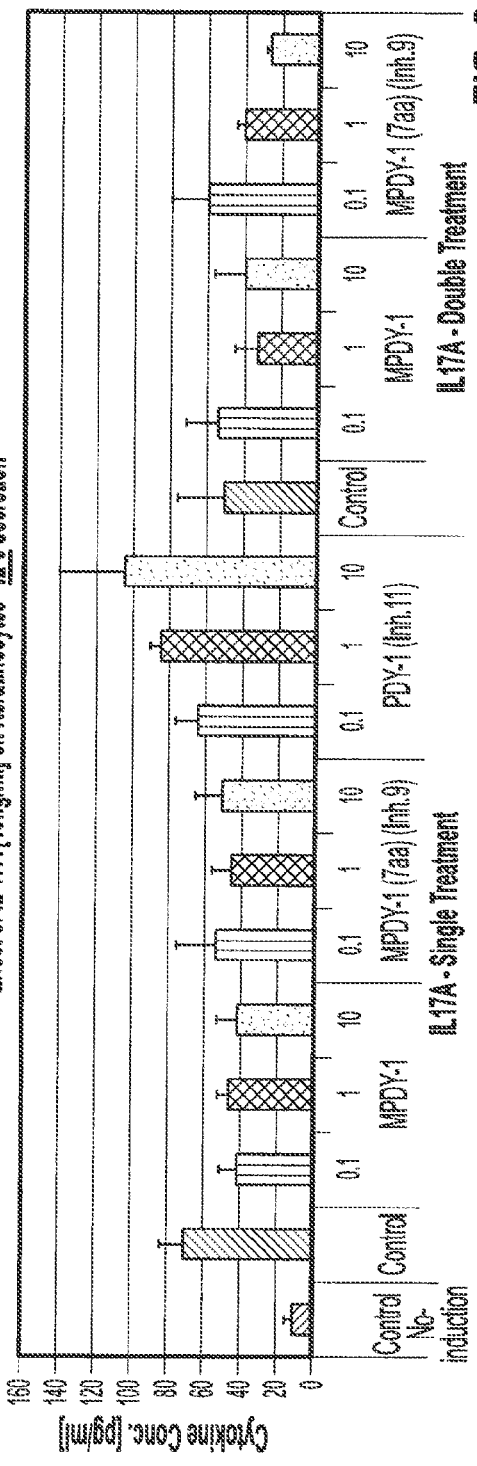

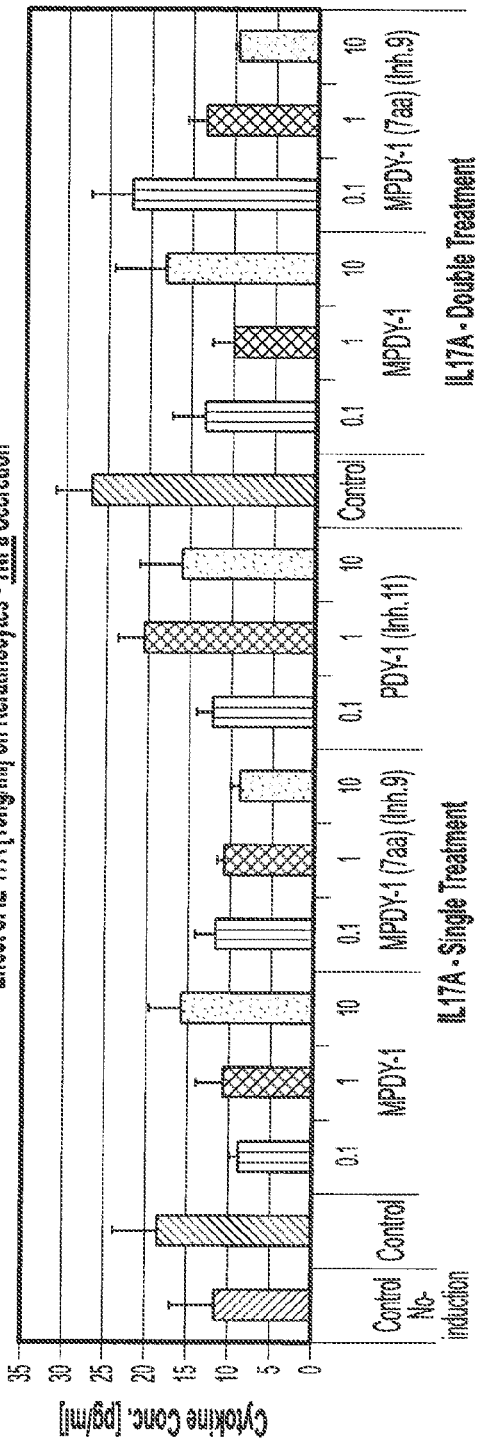
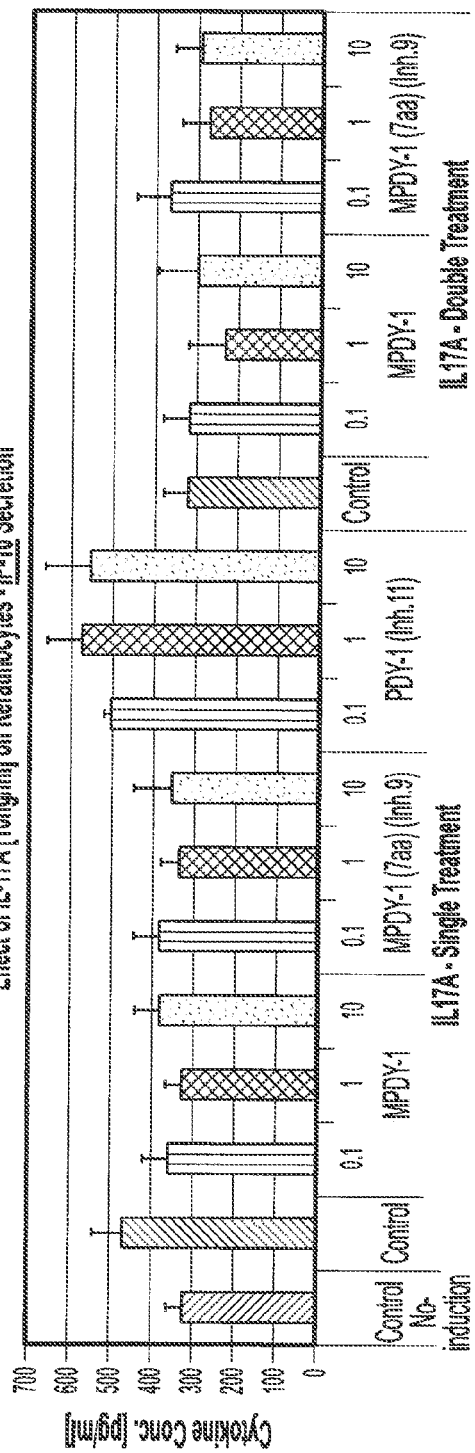
FIG. 25A
FIG. 25B

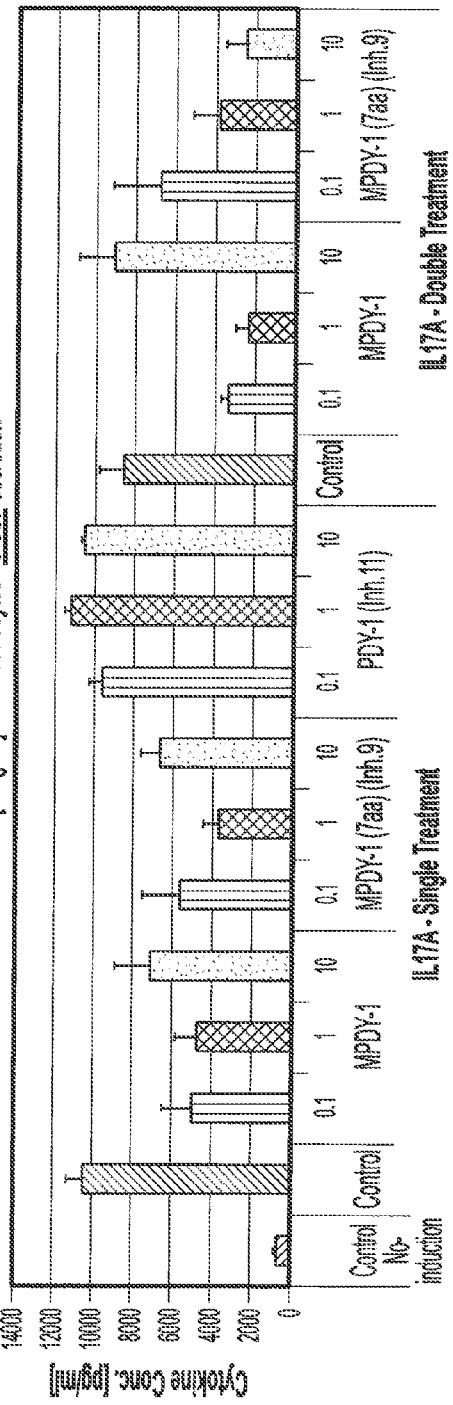
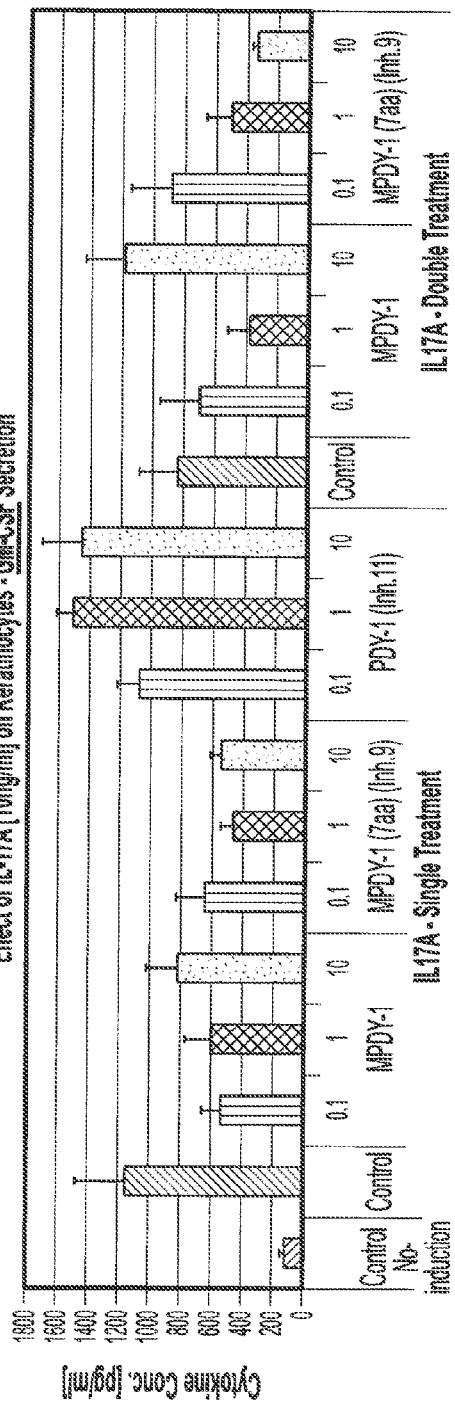
FIG. 26A
FIG. 26B

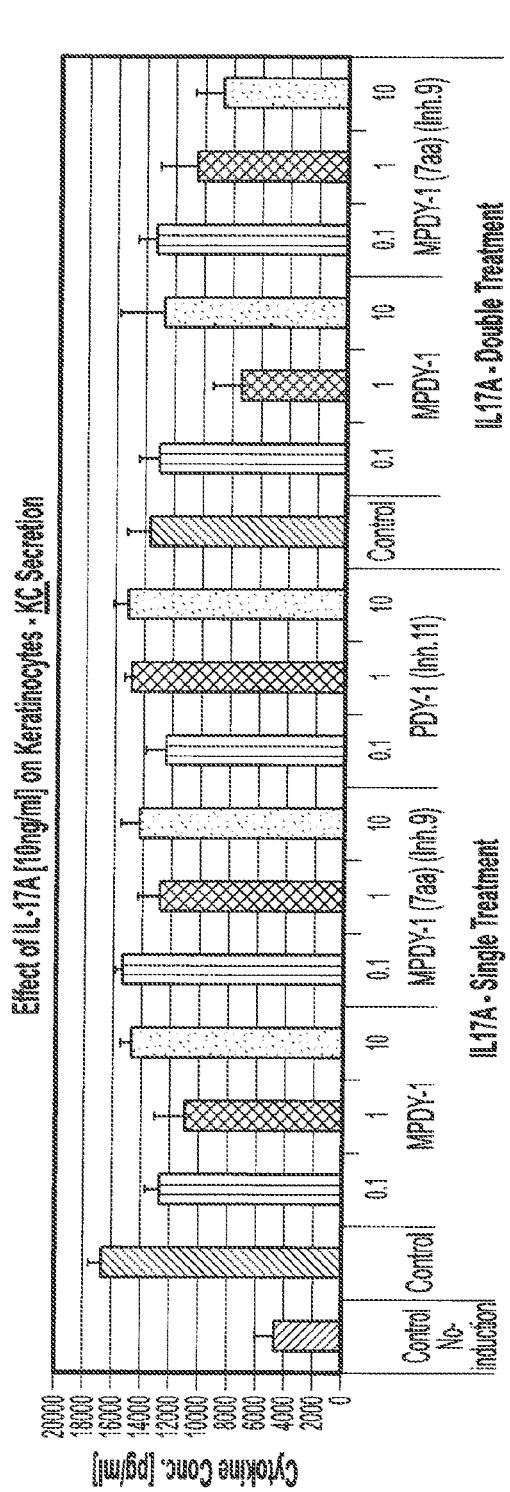
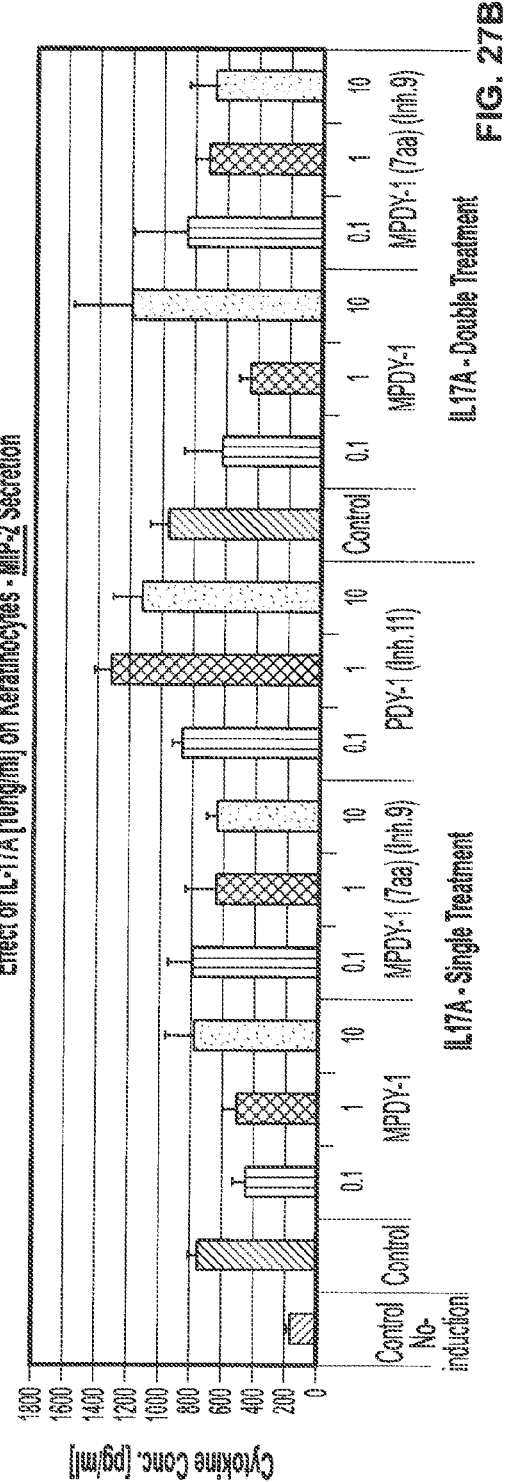

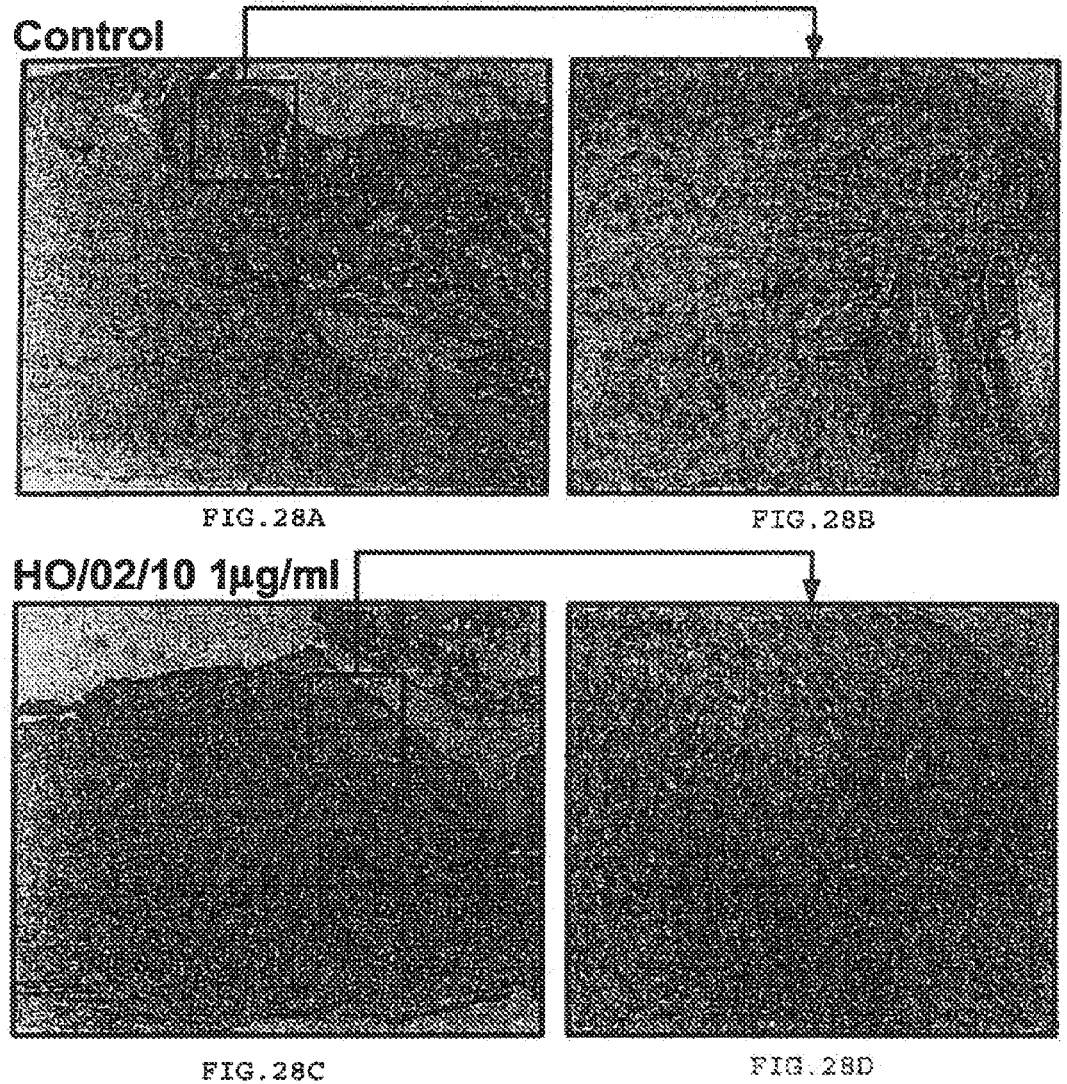

Cream 10ppm
Female
Prick Test
Pre Treatment: Histamine Solution

| VT No. | Cells Type | Stimulation | Treatment | Results |
|---|---|---|---|---|
| 98 | Splenocytes | LPS[0.2ng/ml] | MPDY-1 [1µg/ml] | ↓ IL-6 (50%), |
| | | LPS[1µg/ml] | MPDY-1 [1µg/ml] | ↓ IL-1 (45%), ↓ TNFα (35%), |
| | | | HO/03/03 | ↓ IL-1 (30%), ↓ TNFα (25%), |
| 103 | Splenocytes | LPS[1µg/ml] | MPDY-1 [1µg/ml] | ↓ KC (30%), |
| 107 | Splenocytes | LPS[1µg/ml] | DAP-1 Activator [1,10µg/ml] | DAP-1 ↓ TNFα (25%), ↓ MIP-2 (40%), ↓ IL-6 (30%), ↓ G-CSF (40%), ↓ KC (50%), |
| 106 | DC's | TNFα[5ng/ml] | MPDY-1 [1µg/ml] | ↓ IP-10 (20%), ↓ KC (17%), |
| | Mφ | LPS[1ng,10ng, 100ng,1µg,10µg/ml] LPS[100ng/ml] | MPDY-1 [1µg/ml] | ↓ IL-1α (45%), ↓ IL-1β (50%), ↓ TNFα (37%), ↓ IL-12(70) (40%), ↓ MIP-2 (25%), ↓ KC (40%), ↓ G-CSF (30%), |
| | | | HO/03/03 | ↓ IL-1α (20%), ↓ IL-1β (30%), ↓ IL-12(70) (30%), ↓ G-CSF (30%), |

FIG. 35

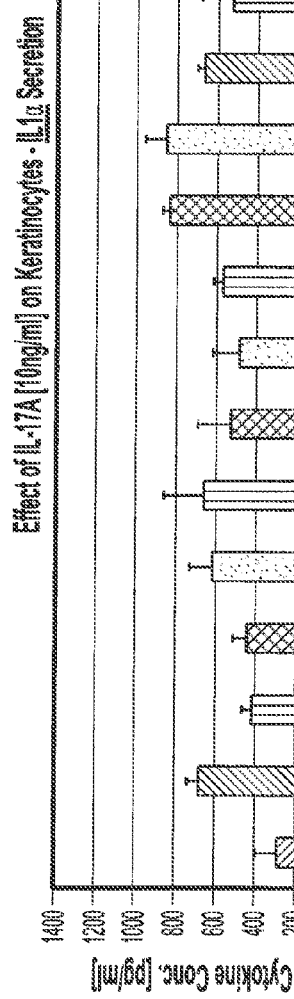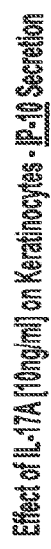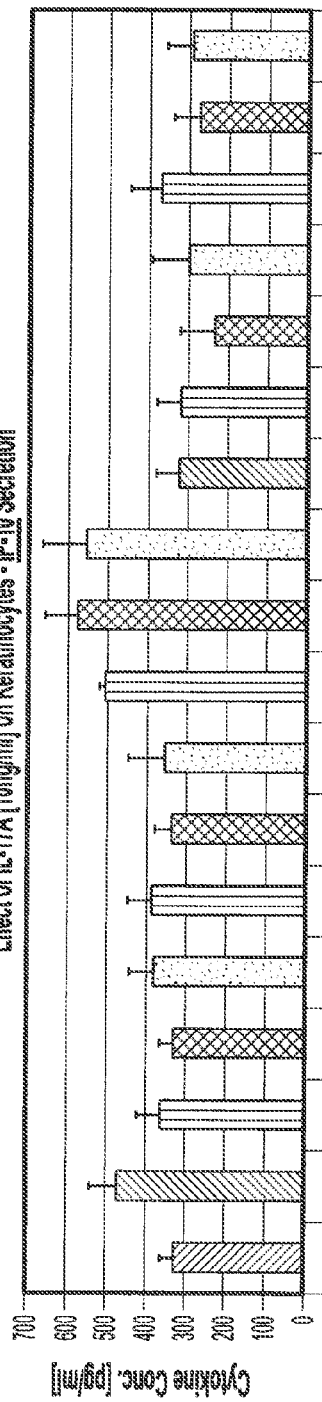

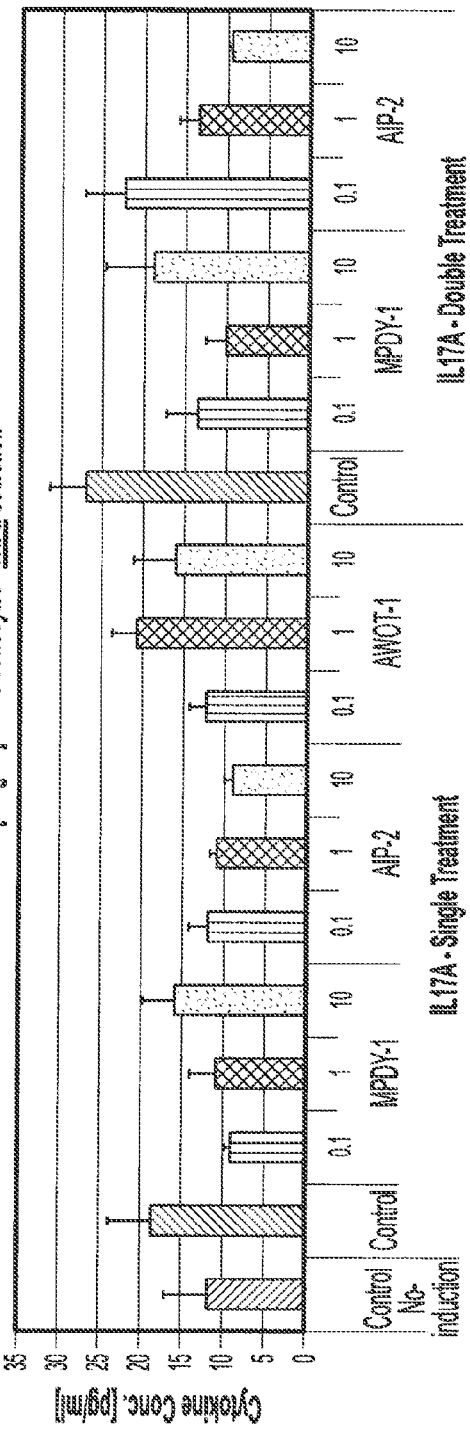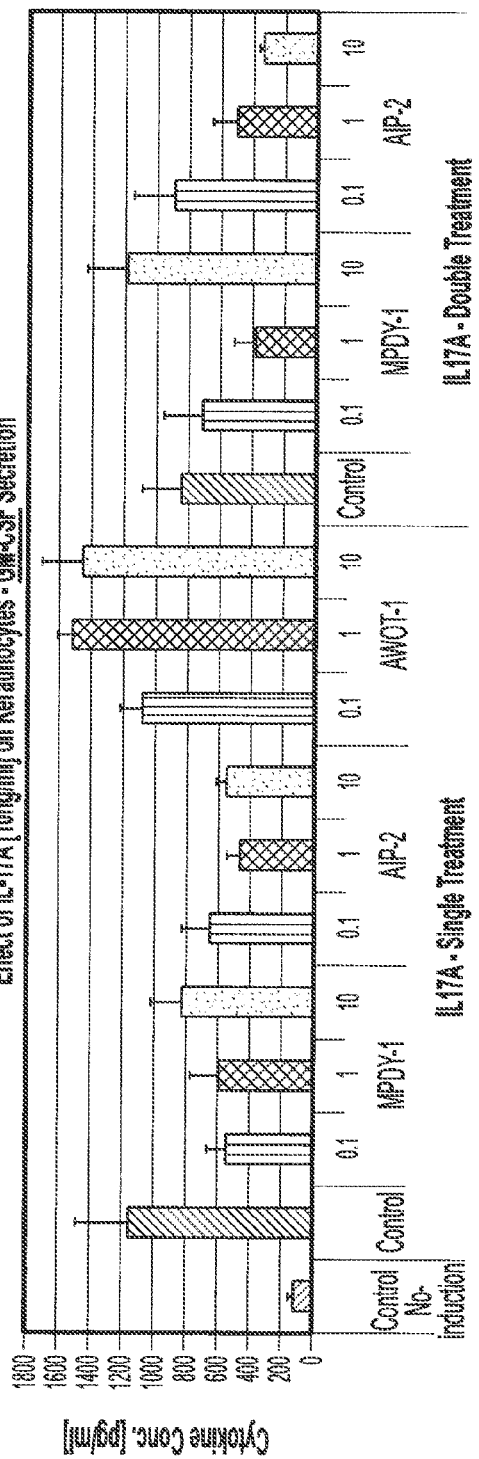

| Stimulation | Treatment | Results |
|---|---|---|
| LPS [1μg/ml] | MPDY-1 [1μg/ml] | TNFα (-60%), IL-6 (-60%), IP-10 (-100%), MIP-2 (-45%), G-CSF (-100%), IL-1α (-10%), GM-CSF (-10%), KC (-25%) |
| | AIP-2 [1μg/ml] | TNFα (-80%), IL-6 (-70%), IP-10 (-100%), MIP-2 (-60%) |
| | AIP-1 [1μg/ml] | G-CSF (-60%), IL-6 (-30%), KC (-30%), IL-10 (-25%), G-CSF (-50%) |
| | AWOT [1μg/ml] | IL-6 (-20%), G-CSF (-160%), IL-6 (-30%), KC (-30%) |
| | PPDY-1 [1μg/ml] | KC (-10%), IL-10 (-40%) |
| LPS [100ng/ml] | MPDY-1 [1μg/ml] | G-CSF (-50%), MIP-2 (-30%), KC (-90%), IL-1α (-80%), L-6 (-50%), GM-CSF (-90%), IL-6 (-15%), MIP-2 (-15%), TNFα (-100%) |
| | AIP-2 [1μg/ml] | IP-10 (-10%), MIP-2 (-20%) |
| | AWOT [1μg/ml] | IP-10 (-70%), MIP-2 (-70%) |
| | PPDY-1 [1μg/ml] | IP-10 (-85%), MIP-2 (-85%) |
| TNFα [35ng/ml] | MPDY-1 [1μg/ml] | IL-1α (-95%), G-CSF (-75%), GM-CSF (-45%), MIP-2 (-25%), IP-10 (-25%) |
| | AIP-2 [1μg/ml] | IL-1α (-80%), G-CSF (-50%), GM-CSF (-60%), IP-10 (-50%), KC (-15%) |
| | AIP-1 [1μg/ml] | GM-CSF (-35%), IL-1α (-85%), G-CSF (-70%), KC (-50%) |
| | PPDY-1 [1μg/ml] | IL-1α (-30%) |
| IL-17α [10ng/ml] | MPDY-1 [0.1μg/ml] | IL-1α (-70%), IL-6 (-40%), TNFα (-160%), G-CSF (50%), GM-CSF (-60%), KC (-65%), MIP-2 (-50%) |
| | MPDY-1 [1μg/ml] | IL-1α (-65%), IL-6 (-30%), TNFα (-130%), IP-10 (-100%), G-CSF (-50%), GM-CSF (-50%), KC (-50%), MIP-2 (-45%) |
| | MPDY-1 [10μg/ml] | IL-1α (-25%), IL-6 (-50%), TNFα (-30%), IP-10 (-75%), G-CSF (-30%), GM-CSF (-30%), KC (-15%) |
| | AIP-2 [0.1μg/ml] | IL-6 (-25%), TNFα (-100%), IP-10 (-100%), G-CSF (-50%), GM-CSF (-50%), KC (-10%) |
| | AIP-2 [1μg/ml] | IL-1α (-50%), IL-6 (-40%), TNFα (-130%), IP-10 (-130%), G-CSF (70%), GM-CSF (-65%), KC (-65%), MIP-2 (-15%) |
| | AIP-2 [10μg/ml] | IL-1α (-50%), IL-6 (-30%), TNFα (-180%), IP-10 (-90%), G-CSF (30%), GM-CSF (-55%), KC (-20%), MIP-2 (-15%) |
| | AWOT [0.1μg/ml] | IL-1α (-35%), IL-6 (-10%), TNFα (-85%), KC (-65%) |
| | AWOT [1μg/ml] | KC (-15%) |
| | AWOT [10μg/ml] | TNFα (-30%), KC (-15%) |

FIG. 70

METHOD FOR TREATMENT OF INFLAMMATORY DISEASE AND DISORDER

CROSS REFERENCE TO RELATED APPLICATIONS

This application is a continuation-in-part of International patent application number PCT/IL2011/000032 filed Jan. 11, 2011, which claims the benefit of provisional application No. 61/293,794 filed Jan. 11, 2010 and the benefit of provisional application No. 61/405,509 filed Oct. 21, 2010.

FIELD OF THE DISCLOSURE

The disclosure relates to treatment of inflammatory diseases and disorders by modulation of PKC activity.

BACKGROUND OF THE DISCLOSURE

Initiation of inflammation begins with an inflammatory response and leads to the activation of neutrophils, granulocytes, monocytes, macrophages, as well as other immunomodulatory cells. This may result in a topical or systemic inflammatory cascade involving inflammatory cytokines and mediators, such as interleukins (ILs), Tumor necrosis factor alpha (TNFα), and prostaglandins. This complex inflammatory mediated cascade triggers a whole range of responses, such as cellular chemotaxis and endothelial injury and leads to the recruitment of additional cells from the innate and adaptive immune systems.

The skin serves as an important boundary between the internal body and the environment, preventing contact with potentially harmful pathogens. In the case of antigen/pathogen penetration, an inflammatory response is often induced to eliminate the antigen. This response leads to a dermal infiltrate that consists predominantly of T cells, polymorphonuclear cells, and macrophages.

The inflammatory response is not necessarily associated with external stimuli, or may be caused by a non-harmful environmental substances (in case of allergies). In both cases an over-expression of proinflammatory cytokines without proper controls leads to inflammation which is the hallmark of topical and systemic inflammation generally, as well as a variety of inflammatory diseases and disorders. Inflammation is associated with a variety of disorders such as eczema and dermatitis, including for example, atopic dermatitis, seborrheic dermatitis, dyshidrotic eczema, nummular dermatitis, stasis dermatitis, allergic dermatitis, psoriasis, pruritis, multiple sclerosis, cutaneous inflammation, cicatricial pemphigoid, scleroderma, hidradenitis suppurativa, toxic epidermal necrolysis, acne, osteitis, graft vs. host disease (GvHD), pyroderma gangrenosum, and Behcet's Syndrome.

Over production of proinflammatory cytokines has been implicated in many inflammatory and autoimmune diseases. For example, the secretion of cytokines such as TNFα and Interleukin-23 (IL-23), which stimulates survival and proliferation of Th17 cells, are highly associated with psoriasis, where IL-6 is required for Th17 development in addition to its general role as proinflammatory cytokine. Other cytokines like IL-12 and IP-10 are initiators and involves in Th1 pathway which is typical to psoriasis and other autoimmune diseases. IL-5, a cytokine that increases the production of eosinophils, is over-expressed in asthma resulting in accumulation of eosinophils in the asthmatic bronchial mucosa, a hallmark of allergic inflammation. IL-4 and IL-13 are known mediators of the hypercontractility of smooth muscle found in inflammatory bowel disease and asthma. Additionally, as discussed further below, inflammatory cytokines have been shown to be implicated in, by way of example, psoriasis, multiple sclerosis, arthritis, ischemia, septic shock, and organ transplant rejection.

Similarly, granulocyte macrophage-colony stimulating factor (GM-CSF) is a regulator of maturation of granulocyte and macrophage lineage population and has been implicated as a key factor in many inflammatory and autoimmune diseases. For example, antibodies that inhibit GM-CSF secretion have been shown to ameliorate autoimmune disease.

Thus, development of therapeutics that reduce secretion of proinflammatory cytokines and/or regulate immunomodulators would be beneficial in alleviating topical and systemic inflammation generally, as well as a host of inflammatory and/or autoimmune diseases as discussed herein. Several lines of evidence point to modulators of PKC isoforms as useful in achieving these results.

Several in vivo studies have shown the involvement of T helper (Th) 17 cells as well as secretion of cytokines such as interleukins and TNFα, by skin associated cells such as keratinocytes, dendritic and T helper cells, as key players in the development of the inflammatory response involved in the pathogenesis of psoriasis and other autoimmune inflammatory diseases. The secretion of cytokines such as TNFα and Interleukin (IL)-23, which stimulates survival and proliferation of Th17 cells, also serves as a key master cytokine regulator for these diseases. (Fitch et al. (2007) *Curr Rheumatol Rep.* 9:461-7). Th17 cells within dermis in turn, induce secretion of IL-17A and IL-22. IL-22, in particular, derive keratinocyte hyperproliferation and augment the inflammatory response in psoriasis (Fitch et al. (2007) *Curr Rheumatol Rep* 9:461-7).

The protein kinase C (PKC) family represents a group of phospholipid dependent enzymes catalyzing the covalent transfer of phosphate from ATP to serine and threonine residues of proteins. The family is currently considered as composed of at least 12 individual isoforms which belong to 3 distinct categories based on their activation by calcium ion(s) and other factors. The PKC family consists of at least ten members, usually divided into three subgroups: classical, novel and atypical PKCs (FIG. 1). The specific cofactor requirements, tissue distribution, and cellular compartmentalization suggest differential functions and the tuning of specific signaling cascades for each isoform. Thus, specific stimuli can lead to differential responses via isoform specific PKC signaling regulated by their factors, such as: expression, localization, and/or phosphorylation status in particular biological settings. PKC isoforms are activated by a variety of extracellular signals and, in turn, modify the activities of cellular proteins including receptors, enzymes, cytoskeletal proteins, and transcription factors. Accordingly, the PKC family plays a central role in cellular signal processing including regulation of cell proliferation, differentiation, survival and death.

PKCα, which is highly abundant in skin, is the major conventional, $Ca^{2+}$ responsive, PKC isoform in epidermis and it was initially the only cPKC detected in the keratinocytes in vitro and in vivo (Dlugosz et al. (1992) *Biomed Pharmacother* 46:304; Wang et al. (1993) *J Cancer Res Clin Oncol* 119:279-287). Therefore, PKCα had been proposed as a key player in $Ca^{2+}$ induced differentiation (Denning et al. (1995) *Cell Growth Differ* 6:149-157; Dlugosz et al. (1992) *Biomed Pharmacother* 46:304). Being in epidermis and mainly restricted to suprabasal layers (Denning et al. (2004) *Int J Biochem Cell Biol* 36:1141-1146), PKCα is involved in cell cycle withdrawal and primarily associated with the keratin cytoskeleton and desmosomal cell-cell junctions (Jansen et al. (2001) *Int J Cancer* 93:635-643; Tibudan et al. (2002) *J Invest Dermatol.* 119:1282-1289). Since, upon exposure to the classical PKC activator TPA (12-O-tetradecanoylphorbol-13-acetate), spinous markers were suppressed, PKCα was thought to be largely responsible for the shift from spinous to granular differentiation as a result of TPA activation (Dlugosz and Yuspa (1993) *J Cell Biol* 120:217-225; Lee et al. (1998) *J Invest Dermatol* 111:762-766; Matsui et al. (1992) *J Invest Dermatol* 99:565-571; Punnonen et al. (1993) *J Invest Dermatol* 101:719-726). Indeed, blocking PKCα activity or its synthesis by antisense oligonucleotides appeared to abolished granular markers and revive spinous markers like K1 and K10. Likewise, implementation of dominant negative PKCα appeared to restore the (late) spinous marker involucrin (Deucher et al. (2002) *J Biol Chem* 277: 17032-17040). Accordingly, defective differentiation in skin cancer (Tennenbaum et al. (1993) *Cancer Res* 3:4803-4810; Tomakidi et al. (2003) *J Pathol* 200:298-307) correlates with elevated PKCα activity, also observed in tumor cells in vitro (Dlugosz et al. (1992) *Biomed Pharmacother* 46:304; Yang et al. (2003) *J Cell Physiol.* 195:249-259). However, over-expression of PKCα in normal human keratinocytes did not appear to alter their differentiation pattern (Deucher et al. (2002) *J Biol Chem* 277:17032-17040). The influence of PKCα on the cellular traffic and membrane recruitment of β1-integrin during migration (Ng et al. (1999) *EMBO J.* 18:3909-3923) may well promote both wound reepithelialization and tumor cell invasion.

Over-expression of PKCα in transgenic mice has appeared to induce a striking inflammatory response, increased epidermal thickening and edema correlated with neutrophil infiltration, multiple micro-abscesses, and a marked increase of inflammatory cytokines and chemokines, such as TNFα, macrophage inflammatory protein-2 (MIP-2), Cyclooxygenase-2 (COX-2) or macrophage inflammatory protein (MIP). These results implicate PKCα in the epidermal inflammatory response (Wang and Smart (1999) *J Cell Sci* 112:3497-3506). Treatment with 12-O-tetradecanoyl phorbol-13-acetate (TPA, a PKCα activator) apparently caused epidermal hyperplasia, intra-epidermal inflammation, and massive apoptosis (Cataisson et al. (2003) *J Immunol* 171:2703-2713; Jansen et al. (2001) *Int J Cancer* 93:635-643). In addition, recent in vivo studies in PKC isoenzyme-selective knockout and transgenic mice appear to have highlighted distinct functions of individual PKCs in the immune system. These genetic analyses, along with biochemical studies appear to indicate that PKC-regulated signaling pathways play a significant role in many aspects of the immune responses. For example, members of the PKC family appear crucial in T cell signaling pathways. Particularly, PKCα, isotype appears to determine the nature of lymphocyte-specific in vivo effector. PKCα is also discussed as being involved in macrophages activation and was apparently shown to be involved in mast cell signaling (Cataisson et al. (2005) *J Immunol* 174:1686-1692).

One example of an inflammatory disease is psoriasis. There are two main hypotheses about the basic pathology leading to psoriasis development. The first considers psoriasis as primarily a disorder of excessive growth and reproduction of skin cells. The second hypothesis considers psoriasis as an immune-mediated disorder in which the excessive reproduction of skin cells is secondary to factors produced by the immune system. Accordingly, most drugs for psoriasis target one component of the disease, either the hyper-proliferative state of skin cells, or the skin inflammatory response as presented in psoriasis plaques.

Recent data support the notion that both pathways underlie the pathology of the diseases through a cross talk between skin cells and immunological milieu (encompassing environment, surroundings, location and/or setting). Classic genome wide linkage analysis has identified nine locations (loci) on different chromosomes associated with tendency to develop psoriasis named psoriasis susceptibility 1 through 9 (PSORS1 through PSORS9) loci. In these locations several genes were characterized and found to encode for proteins expressed in epidermal cells such as corneodesmosin, expressed in the granular and cornified layers of the epidermis and upregulated in psoriasis. On the other hand, other psoriasis linked genes encode for proteins involved in modulation of the immune system where characterized such as IL-12B on chromosome 5q (Frank et al. (2009) *N Engl J Med* 361:496-509).

WO 2005/007072 of some of the inventors of the present application discloses pharmaceutical compositions for topical administration, for inducing or accelerating a healing process of a damaged skin or skin wound, comprising insulin and additional agent, such as alpha PKC inhibitor, acting in synergy with the insulin.

WO 2009/016629 of some of the inventors of the present application discloses compositions comprising a delta-PKC activator, an alpha PKC inhibitor, and a carrier that is free of calcium ($Ca^{2+}$) and magnesium ($Mg^{2+}$) cations for decreasing inflammation at the site of a skin wound.

Current therapies for combating inflammatory diseases generally fail to provide a multi-component approach targeting multiple components of pathogenesis. For example, many treatments for autoimmune diseases involve targeting a single component of a disease, either by blocking cellular proliferation, or by suppressing the immune response in order to block inflammation. Consequently, there is a strong need to provide effective therapeutics which target multiple components of inflammatory disease pathogenesis by targeting and modulating PKC isoform activity. Specifically targeted therapeutics that are capable of selective inhibition or activation of specific PKC isoforms are necessary and would provide for a therapeutic approach that targets multiple components of inflammatory disease pathogenesis, while retaining a low level of side effects, for example, when topically administered. Thus, development of therapeutics that reduce secretion of proinflammatory cytokines and/or regulate immunomodulators via PKC isoform modulation would be beneficial in alleviating topical and systemic inflammation generally and specifically, inflammation of the skin and other epithelial tissues.

SUMMARY OF THE DISCLOSURE

The present disclosure relates to treatment of inflammatory diseases and disorders by administering to a subject a modulator of PKC, such as an inhibitor of PKCα, PKCε, or PKCη, or an activator of PKCδ. Specifically, the compositions and methods of the present invention are useful for the treatment of inflammatory disorders and diseases the skin and other epithelial tissues. In particular it is shown that specific peptide or polypeptide modulators of PKC isoforms are capable, not only of promoting wound healing but also to treat skin and other epithelial tissue diseases and disorders. According to some embodiments the compositions are unexpectedly effective when applied topically as a sole active ingredient.

Without wishing to be bound by any specific theory, it is suggested that the peptide modulators of PKC according to the present invention, even when applied topically, have not only local effect on the skin cells, but also systemic effect on the immune system, leading to inhibition of the pro-inflammatory cytokine cascade.

As exemplified herein, the modulatory peptides of the present disclosure exhibit direct effects on secretion of cytokines by splenocytes. The direct effects of the modulatory peptides are also significant on keratinocytes.

Accordingly, in one aspect, the present disclosure provides a method of inhibiting the secretion of a pro-inflammatory cytokine in a subject suffering from an inflammatory disease or disorder, comprising administering a pharmaceutical composition comprising at least one PKC modulator peptide, thereby treating the inflammatory disease or disorder. More specifically, inflammatory diseases or disorders of the skin or other epithelial tissue are treated by administering to the subject a modulator of PKC.

According to some embodiments, the PKC modulator is an inhibitor of certain PKC isoforms. According to some embodiments, the PKC inhibitor selectively inhibits PKCα, PKCε or PKCη. According to some particular embodiments, the PKC inhibitor is a peptide according to any one of SEQ ID NOs: 1-5, 6-11, and 12-13 which selectively inhibits PKCα, PKCε and PKCη, respectively, or a salt, analog or derivative thereof.

According to some embodiments, the PKC modulator is an activator of other PKC isoforms. According to some embodiments, the PKC activator selectively activates PKCι. In various embodiments, the activator is a peptide of according to any one of SEQ ID NOs: 14-17, or a salt, analog or derivative thereof.

According to some specific embodiments, a PKC modulator used in the methods of the present invention is an inhibitor of PKC alpha or epsilon selected from the group consisting of: AIP-1 (SEQ ID NO: 3), AIP-2 (SEQ ID NO: 4), EPIP-1 (SEQ ID NO: 6), EPIP-2 (SEQ ID NO: 7), EPIP-3 (SEQ ID NO: 8), EPIP-4 (SEQ ID NO: 9), EPIP-5 (SEQ ID NO: 10), EPIP-6 (SEQ ID NO: 11), or an analog, salt or derivative thereof; or an activator of PKC delta selected from the group consisting of DAP-1 (SEQ ID NO: 16), DAP-2 (SEQ ID NO: 14), DAP-3 (SEQ ID NO: 15), DAP-4 (SEQ ID NO: 17), ZIP-1 (SEQ ID NO: 18), or an analog, salt or derivative thereof. Each possibility is a preferred embodiment of the present invention.

According to yet other embodiments, the PKC modulator used in the methods of the present invention is: i. an inhibitor of PKC alpha or epsilon selected from the group consisting of AIP-1 (SEQ ID NO: 3), AIP-2 (SEQ ID NO: 4), EPIP-1 (SEQ ID NO: 6), EPIP-2 (SEQ ID NO: 7), EPIP-3 (SEQ ID NO: 8), EPIP-4 (SEQ ID NO: 9), or an analog, salt or derivative thereof or an activator of PKC delta selected from the group consisting of: DAP-1 (SEQ ID NO: 16), DAP-2 (SEQ ID NO: 14), DAP-3 (SEQ ID NO: 15), ZIP-1 (SEQ ID NO: 18), or an analog, salt or derivative thereof. Each possibility is a preferred embodiment of the present invention.

According to some embodiments, derivatives of the PKC modulator peptides are provided, comprising a permeability moiety conjugated to the peptide sequence.

According to some embodiments, the permeability moiety is connected, by a covalent bond, to the N-terminus of the peptide.

According to some embodiments the permeability moiety attached to the PKC modulator peptide is selected from the group consisting of i. hydrophobic moiety such as fatty acid, steroid and bulky aromatic or aliphatic compound; ii. moiety which may have cell-membrane receptors or carriers, such as steroid, vitamin and sugar; and iii. transporter peptide or amino acid.

According to some embodiments, the fatty acid comprises an aliphatic tail of 3-12 carbons. According to some particular embodiments, the fatty acid is selected from the group consisting of: myristic acid, palmitic acid and cholesterol.

According to some particular embodiments, the PKC modulator, comprising a permeability moiety is a peptide according to any one of SEQ ID NOs: 19-25, or an analog, derivative or salt thereof.

According to some embodiments, peptides analogs, comprising modified amino- or carboxy-terminus of the PKC modulator peptide, are provided. According to some particular embodiments, the modification is selected from the group consisting of: N-terminus acylation, C-terminus amidation and modification of the C-terminal acid to an alcohol.

According to some embodiments, the inflammatory disease of the skin is selected from the group consisting of: pruritus, skin inflammation, psoriasis, atopic dermatitis, allergic contact dermatitis, irritant contact dermatitis, and seborrhoeic dermatitis.

According to a particular embodiment, the inflammatory disease of the skin is pruritus.

According to yet other embodiments, the inflammatory disease or disorder of epithelial tissue is selected from the group consisting of: keratinopathy, asthma, inflammatory bowel disease such as ulcerative colitis and Crohn's disease.

A pharmaceutical composition according to the present invention, comprising at least one PKC mediator, and a carrier, diluent or excipient, may be, according to some embodiments, free of calcium ($Ca^{2+}$) and magnesium ($Mg^{2+}$) cations. According to yet other embodiment, a pharmaceutical composition according to the present invention may comprise calcium ($Ca^{2+}$) and/or magnesium ($Mg^{2+}$) cations.

A pharmaceutical composition comprising a PKC modulator according to the present invention may be administered by any suitable route of administration, including topically or systemically. Modes of administration include but are not limited to topical and transdermal routes as well as parenteral routes such as intravenous and intramuscular injections, as well as via nasal or oral ingestion.

According to some embodiments, the PKC modulator is administered topically. According to other embodiments, the PKC modulator is administered systemically.

As it is known to those skilled in the art a pharmaceutical composition comprising a PKC modulator according to the present invention may be administered alone or in conjunction with additional treatments for the conditions to be treated.

In various aspects, the present disclosure provides a kit for carrying out the method of the disclosure. In one embodiment, the kit includes an inhibitor of PKC, such as an inhibitor of PKCα, PKCε or PKCη, or an activator of PKCδ, as well as instructions for administering the inhibitor or activator.

Some of the specific peptide modulators of PKC isoformes used in the methods of the present invention are listed in Table 1:

TABLE 1

Examples of PKC Isoform Inhibitor and Activator Peptides

| Name | Amino Acid Sequence | SEQ ID |
|---|---|---|
| | PKCα Inhibitors | |
| | Phe-Ala-Arg-Lys-Gly-Ala | 1 |
| | Phe-Ala-Arg-Lys-Gly-Ala-Arg-Gln | 2 |
| | Palmitoyl-Phe-Ala-Arg-Lys-Gly-Ala-Arg-Gln | 19 |

TABLE 1-continued

Examples of PKC Isoform Inhibitor and Activator Peptides

| Name | Amino Acid Sequence | SEQ ID |
|---|---|---|
| AIP-1 | Thr-Leu-Asn-Pro-Gln-Trp-Glu-Ser | 3 |
|  | Phe-Ala-Arg-Lys-Gly-Ala-Leu | 4 |
| AIP-2 | Myristoyl-Phe-Ala-Arg-Lys-Gly-Ala-Leu | 20 |
| MPDY-1 | Myristoyl-Phe-Ala-Arg-Lys-Gly-Ala-Leu-Arg-Gln | 21 |
| AWOT | Phe-Ala-Arg-Lys-Gly-Ala-Leu-Arg-Gln | 5 |
| PPDY-1 | Palmitoyl-Phe-Ala-Arg-Lys-Gly-Ala-Leu-Arg-Gln | 22 |
| PKCε Inhibitors | | |
| EPIP-1 | Glu-Ala-Val-Ser-Leu-Lys-Pro-Thr | 6 |
| EPIP-2 | Pro-Tyr-Ile-Ala-Leu-Asn-Val-Asp | 7 |
| EPIP-3 | Pro-Ala-Trp-His-Asp | 8 |
| EPIP-4 | Leu-Glu-Pro-Glu-Ala-Ala-Ala-Ala-Ala-Gly-Lys | 9 |
| EPIP-5 | His-Phe-Glu-Asp-Trp-Ile-Asp | 10 |
| EPIP-6 | Val-Tyr-Val-Ile-Ile-Asp-Leu | 11 |
| PKCη Inhibitors | | |
|  | Lys-Arg-Thr-Leu-Arg | 12 |
|  | Myristoyl-Lys-Arg-Thr-Leu-Arg | 23 |
|  | Thr-Arg-Lys-Arg-Gln-Arg-Ala-Met-Arg-Arg-Arg-Val-His-Gln-Ile-Asn-Gly | 13 |
| MPE-1 | Myristoyl-Thr-Arg-Lys-Arg-Gln-Arg-Ala-Met-Arg-Arg-Arg-Val-His-Gln-Ile-Asn-Gly | 24 |
| PKCδ Activators | | |
| DAP-2 | His-Phe-Glu-Asp-Thr-Ile-Asp | 14 |
| DAP-3 | His-Phe-Glu-Asp-Trp-Ile-Asp-His-Phe-Glu-Asp-Trp-Ile-Asp | 15 |
| DAP-1 | Met-Arg-Ala-Ala-Glu-Ala-Ala-Ala-Glu-Pro-Met | 16 |
| DAP-4 | Val-Tyr-Val-Ile-Ile-Asp-Leu-His-Phe-Glu-Asp-Trp-Ile-Asp | 17 |
| PKCζ Inhibitor | | |
|  | Ser-Ile-Tyr-Arg-Arg-Gly-Ala-Arg-Arg-Trp-Arg-Lys-Leu | 18 |
| ZIP-1 | Myristoyl-Ser-Ile-Tyr-Arg-Arg-Gly-Ala-Arg-Arg-Trp-Arg-Lys-Leu | 25 |

In another aspect, the present disclosure provides an isolated peptide modulator of PKC.

According to some embodiments, the peptide modulator of PKC is set forth in a sequence selected from the group consisting of SEQ ID NO: 9, SEQ ID NO: 15, SEQ ID NO: 16 and SEQ ID NO: 17 or an analog, derivative or salt thereof. Each possibility represents a separate embodiment of the present invention.

According to some embodiments, the peptide modulator of PKC is a peptide of 6-30 amino acids comprising the sequence Glu-Ala-Ala-Ala-Ala (SEQ ID NO:26). According to some specific embodiments, the peptide modulator is set forth in a sequence selected from the group consisting of SEQ ID NO: 9 and SEQ ID NO: 16, or an analog, derivative or salt thereof. Each possibility represents a separate embodiment of the present invention.

According to other embodiments, the peptide modulator of PKC is a peptide multimer of 12-60 amino acids, comprising at least two, identical or different, sequences wherein at least one of the sequences is set forth in a sequence selected from the group consisting of SEQ ID NOs: 1-18. Each possibility represents a separate embodiment of the present invention.

According to some specific embodiments, the peptide multimer comprises the sequence His-Phe-Glu-Asp-Trp-Ile-Asp (SEQ ID NO: 14). According to particular embodiments, the peptide multimer is set forth in a sequence selected from SEQ ID NO: 15 and SEQ ID NO:17. Each possibility represents a separate embodiment of the present invention.

According to some embodiments the peptide modulator or peptide multimer comprises a permeability moiety. According to particular embodiments, the permeability moiety is a fatty acid. According to some specific embodiments an N-myristoylated peptide of any one of SEQ ID NOs: 9, 15, 16 and 17 is provided. Each possibility represents a separate embodiment of the present invention.

The present disclosure further provides a pharmaceutical composition comprising at least one isolated peptide modulator of PKC and a pharmaceutically acceptable vehicle, diluent or excipient. According to some embodiments, the peptide modulator is a peptide of SEQ ID NO: 9, 15, 16 or 17, or an analog, derivative or salt thereof. According to some particular embodiments, the pharmaceutical composition comprises a peptide multimer comprising at least two, identical or different, sequences wherein at least one of the sequences is set forth in a sequence selected from the group consisting of SEQ ID NOs: 1-18. According to specific embodiments, the pharmaceutical compositions comprises a peptide multimer according to SEQ ID NO: 15 and SEQ ID NO:17. According to some specific embodiments, the pharmaceutical compositions comprise an N-myristoylated-derivative of a peptide of any one of SEQ ID NO: 9, 15, 16 and 17; and a pharmaceutically acceptable vehicle, diluent or excipient.

In another aspect, the present invention provides a method of treating an inflammatory disease or disorder comprising administering to a subject in need thereof, a pharmaceutical composition comprising at least one peptide set forth in a sequence selected from the group consisting of: SEQ ID NO: 9, SEQ ID NO: 15, SEQ ID NO: 16 and SEQ ID NO: 17, or a peptide multimer comprising at least two, identical or different, sequences wherein at least one of the sequences is set forth in a sequence selected from the group consisting of SEQ ID NOs: 1-18 or a salt, derivative or analog thereof.

BRIEF DESCRIPTION OF THE DRAWINGS

FIGS. 5A-5C are a series of pictorial representations showing expression of Filaggrin (Fil), Loricrin (Lor) and Keratin 1 (K1) with or without treatment with a pharmaceutical composition (denoted HO/02/10) comprising the PKCα inhibitor of SEQ ID NO:21 (MPDY-1).

FIG. 6A is a pictorial representation showing expression of PCNA. FIG. 6B is a histogram comparing the percentage of PCNA positive cells treated with HO/02/10 and control.

FIG. 16A-16B is a series of stains showing MAC-2 expression. FIG. 16C is a histogram comparing the number of cells per field of MAC-2 positively stained cells with control, 1, 10 and 100 micrograms per mL MDPY-1 (from left).

FIG. 17A compares secretion of IL-6, IL-1α, and GM-CSF. FIG. 17B compares secretion of G-CSF. FIG. 17C compares secretion of MIP-2. FIG. 17D compares secretion of KC.

FIG. 18A compares secretion of G-CSF, KC and MIP-2. FIG. 18B compares secretion of IL-1α(left bars of histogram pairs) and TNFα (right bars of histogram pairs). FIG. 18C compares secretion of IL-1β (left bars of histogram pairs) and IL-12 (right bars of histogram pairs).

FIG. 21A compares secretion of IL-1A. FIG. 21B compares secretion of IL-6.

FIG. 22A compares secretion of G-CSF. FIG. 22B compares secretion of GM-CSF.

FIG. 23A compares secretion of MIP-2. FIG. 22B compares secretion of IP-10.

FIGS. 24A and 24B are histograms comparing cytokine secretion in IL-17A activated keratinocytes treated with peptide PKCα inhibitors. FIG. 24A compares secretion of IL-1A. FIG. 24B compares secretion of IL-6.

FIGS. 25A and 25B are histograms comparing cytokine secretion in IL-17A activated keratinocytes treated with peptide PKCα inhibitors. FIG. 25A compares secretion of TNFα. FIG. 25B compares secretion of IP-10.

FIGS. 26A and 25B are histograms comparing cytokine secretion in IL-17A activated keratinocytes treated with peptide PKCα inhibitors. FIG. 26A compares secretion of G-CSF. FIG. 26B compares secretion of GM-CSF.

FIGS. 27A and 27B are histograms comparing cytokine secretion in IL-17A activated keratinocytes treated with peptide PKCα inhibitors. FIG. 27A compares secretion of KC. FIG. 27B compares secretion of MIP-2.

FIGS. 28A-28E are a series of pictorial and graphical representations showing down regulation of T cell infiltration to the dermis and epidermis during the inflammatory stage after treatment with HO/02/10. FIGS. 28A-28D are a series of stains using anti-CD3 antibodies. FIG. 28E is a histogram comparing the number of cells per field of CD3 positively stained cells after treatment with HO/02/10.

FIG. 31A is a stain using neutrophil specific antibodies. FIG. 31B is a histogram comparing the number of cells per field of neutrophil specific positively stained cells.

FIG. 35 is a table of data collected in in vitro immunological tests for PKCα inhibitor MPDY-1 (SEQ ID NO:21) and PKCδ activator DAP-1 (SEQ ID NO: 16).

FIG. 62 is a histogram comparing cytokine secretion in IL-17A activated keratinocytes treated with peptide PKCα inhibitors MPDY-1 (SEQ ID NO: 21), AWOT-1 (SEQ ID NO: 5), and AIP-2 (SEQ ID NO: 20).

FIG. 63 is a histogram comparing cytokine secretion in IL-17A activated keratinocytes treated with peptide PKCα inhibitors MPDY-1 (SEQ ID NO: 21), AWOT-1 (SEQ ID NO: 5), and AIP-2 (SEQ ID NO: 20).

FIG. 64 is a histogram comparing cytokine secretion in IL-17A activated keratinocytes treated with peptide PKCα inhibitors MPDY-1 (SEQ ID NO: 21), AWOT-1 (SEQ ID NO: 5), and AIP-2 (SEQ ID NO: 20).

FIG. 65 is a histogram comparing cytokine secretion in IL-17A activated keratinocytes treated with peptide PKCα inhibitors MPDY-1 (SEQ ID NO: 21), AWOT-1 (SEQ ID NO: 5), and AIP-2 (SEQ ID NO: 20).

FIG. 70 is a tabular summary of results for various PKCα inhibitors of cytokine secretion in keratinocytes treated with LPS, TNFα or IL-17A and inhibitor.

DETAILED DESCRIPTION OF THE DISCLOSURE

Figure 1:
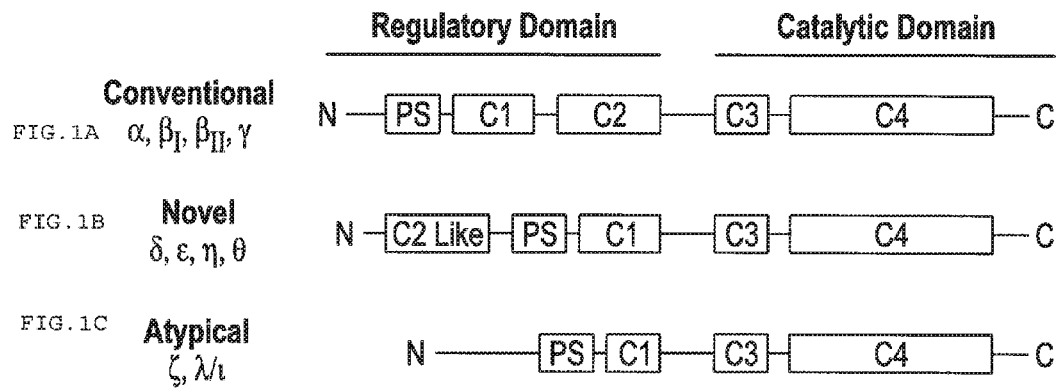
FIGS. 1A-1C show a pictorial representation depicting various members of the PKC family of isoforms.

The present disclosure is based on the discovery that modulators of PKC isoforms may be administered as sole active ingredients in effective treatments for inflammatory diseases and disorders of skin and other epithelial tissues. The involvement of PKC isoforms in major cellular processes of skin cells, as well as many components of the immune system, marks it as a potential target for the treatment of inflammatory pathologies. The data presented herein, demonstrate that PKC family isoforms regulate activation processes in skin and immune cells associated with inflammation and inflammatory diseases.

It is to be understood that this disclosure is not limited to particular compositions, methods, and experimental conditions described, as such methods and conditions may vary. It is also to be understood that the terminology used herein is for purposes of describing particular embodiments only, and is not intended to be limiting, as the scope of the present disclosure will be limited only in the appended claims.

The principles and operation of the methods according to the present disclosure may be better understood with reference to the figures and accompanying descriptions.

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

Unless defined otherwise, all technical and scientific terms used herein have the same meaning as commonly understood by one of skill in the art to which this disclosure belongs. Although any methods and materials similar or equivalent to those described herein can be used in the practice or testing of the disclosure, some preferred methods and materials are now described.

As used herein, the term "subject" refers to a mammalian subject. As such, treatment of any animal in the order mammalian is envisioned. Such animals include, but are not limited to horses, cats, dogs, rabbits, mice, goats, sheep, non-human primates and humans. Thus, the method of the present disclosure is contemplated for use in veterinary applications as well as human use.

"Treatment" of a subject herein refers to both therapeutic treatment and prophylactic or preventative measures. Those in need of treatment include those already with an inflammatory disease or disorder as well as those in which it is to be prevented. Hence, the subject may have been diagnosed as having an inflammatory disease or disorder or may be predisposed or susceptible to an inflammatory disease or disorder.

As used herein, an "inflammatory disease or disorder" is intended to include any disease and disorder having etiologies associated with PKC family isoform regulation. Such diseases include, and are not limited to, pruritus, skin inflammation, psoriasis, multiple sclerosis, rheumatoid arthritis, osteoarthritis, systemic lupus erythematosus, Hashimoto's thyroidis, myasthenia gravis, diabetes type I or II, asthma, inflammatory lung injury, inflammatory liver injury, inflammatory glomerular injury, atopic dermatitis, allergic contact dermatitis, irritant contact dermatitis, seborrhoeic dermatitis, Sjoegren's syndrome, keratoconjunctivitis, inflammatory bowel disease, Crohn's disease, ulcerative colitis, an inflammatory disease of the joints, skin, or muscle, acute or chronic idiopathic inflammatory arthritis, myositis, a demyelinating disease, chronic obstructive pulmonary disease, interstitial lung disease, interstitial nephritis and chronic active hepatitis.

A "symptom" of an inflammatory disease or disorder is any morbid phenomenon or departure from the normal in structure, function, or sensation, experienced by the subject and indicative of an inflammatory disease or disorder.

The expression "effective amount" refers to an amount of an inhibitor or activator of a PKC isoform, such as the polypeptides of SEQ ID NOs: 1-25, that is effective for preventing, ameliorating or treating an inflammatory disease or disorder. Such an effective amount will generally result in an improvement in the signs, symptoms and/or other indicators of an inflammatory disease or disorder. For example, in skin inflammation, an effective amount results in the reduction of swelling and/or inflammation and/or clearance of redness. For pruritus, an effective amount may result in the clearance of redness and/or itchiness.

As used herein, the term "PKC isoform" as used herein encompasses all PKC isoforms including PKCα, PKCβ, PKCδ, PKCε, PKCη, PKCζ, PKCγ, PKCθ, and PKCλ.

The phrase "modulating expression and/or activity of a PKC isoform" relates to an increased or reduced expression and/or activity of a PKC isoform. Increase of the expression leads to increased production of the PKC isoform.

The term "activator" is used herein to describe a molecule that enhances expression and/or activity of a PKC isoform. The term "inhibitor" is used herein to describe a molecule that inhibits expression and/or activity of a PKC isoform. Among others, the phosphoryl transfer region, the pseudosubstrate domain, the phorbolester binding sequences, and the phosphorylation sites may be targets for modulation of PKC activity.

The "pseudosubstrate region" or autoinhibitory domain of a PKC isoform is herein defined as a consensus sequence of substrates for the kinase with essentially no phosphorylatable residue. The pseudosubstrate domain is based in the regulatory region, closely resembling the substrate recognition motif, which blocks the recognition site and prevents phosphorylation. Thus, inhibitory peptides of PKC isoforms, such as some of the peptides of the present disclosure, are obtained as by replacing a phosphorylatable residue of serine (S) or tyrosine (Y) by a non-phosphohorylatable residue such as, for example alanine (A), valine (V), leucine (L). PKCδ is the only PKC isoform known to have additional binding site enabling the isoform's activation on the C2 domain, the conserved domain 2 of PKCδ.

"Permeability" refers to the ability of an agent or substance to penetrate, pervade, or diffuse through a barrier, membrane, particularly cells' membrane, or a skin layer. Any conjugate which succeeds in penetrating into the cells whether by a passive diffusion (e.g., lipophilic moieties that penetrate the lipid bilayer of the cells), or a passive mechanist (e.g., encapsulation or liposome uptake or the like), or by active uptake (e.g. attachment to a moiety that is transported into the cells or through the membrane), is included within the scope of the present invention.

A "permeability moiety", denoted also "a permeability enhancing moiety", according to the invention may be any moiety biological or chemical (natural, semi-synthetic or synthetic) capable of facilitating or enhancing entry, penetration, pervading or diffusion of the PKC modulator to which it is conjugated, through a barrier, membrane, particularly cells' membrane, or a skin layer, or into the target cells. Non-limiting examples of permeability moieties include hydrophobic moieties such as lipids, fatty acids, steroids and bulky aromatic or aliphatic compounds; moieties which may have cell-membrane receptors or carriers, such as steroids, vitamins and sugars, natural and non-natural amino acids and transporter peptides. More specific examples include cationic protein transduction domains (PTDs) such as HIV-1 TAT, Drosophila Antennapedia, poly-arginine (R7) (synthetic), PTD-5 (synthetic), amphipathic PTDs such as transportan (chimeric, galanin fragment plus mastoparan), KALA and more. Other examples are small organic molecules, notably lipophilic that are known to promote transfer across cell membranes of agents that are complexed or covalently attached to them.

Non-limiting examples for lipidic moieties which may be used according to the present invention: Lipofectamine, Transfectace, Transfectam, Cytofectin, DMRIE, DLRIE, GAP-DLRIE, DOTAP, DOPE, DMEAP, DODMP, DOPC, DDAB, DOSPA, EDLPC, EDMPC, DPH, TMADPH, CTAB, lysyl-PE, DC-Cho, -alanyl cholesterol, DCGS, DPPES, DCPE, DMAP, DMPE, DOGS, DOHME, DPEPC, Pluronic, TWEEN, BRIJ, plasmalogen, phosphatidylethanolamine, phosphatidylcholine, glycerol-3-ethylphosphatidylcholine, dimethyl ammonium propane, trimethyl ammonium propane, diethylammonium propane, triethylammonium propane, dimethyldioctadecylammonium bromide, a sphingolipid, sphingomyelin, a lysolipid, a glycolipid, a sulfatide, a glycosphingolipid, cholesterol, cholesterol ester, cholesterol salt, oil, N-succinyldioleoylphosphatidylethanolamine, 1,2-dioleoyl-sn-glycerol, 1,3-dipalmitoyl-2-succinylglycerol, 1,2-dipalmitoyl-sn-3-succinylglycerol, 1-hexadecyl-2-palmitoylglycerophosphatidylethanolamine, palmitoylhomocystiene, N,N'-Bis (dodecyaminocarbonylmethylene)-N, N'-bis((-N,N,N-trimethylammonium-ethylaminocarbonylmethylene)ethylenediamine tetraiodide, N,N"-Bis(hexadecylaminocarbonylmethylene)-N,N,N"-tris ((—N,N,N-trimethyl-ammonium-ethylaminocarbonylmethylenediethylenetriamine hexaiodid, N,N'-Bis (dodecylaminocarbonylmethylene)-N,N"-bis((—N,N,N-trimethylammon-ium ethylaminocarbonylmethylene) cyclohexylene-1,4-diamine tetraiodide, 1,7,7-tetra-((-N,N,N,N-tetramethylammoniumethylaminocarbonylmethylene)-3-hexadecylaminocarbonyl-methylene-1,3,7-triaazaheptane heptaiodide, N,N,N',N'-tetra((-N,N,N-trimethylammonium-ethylaminocarbonylmethylene)-N-'-(1,2-dioleoylglycero-3-phosphoethanolamino carbonylmethylene)diethylenetriamine tetraiodide, dioleoylphosphatidylethanolamine, a fatty acid, a lysolipid, phosphatidylcholine, phosphatidylethanolamine, phosphatidylserine, phosphatidylglycerol, phosphatidylinositol, a sphingolipid, a glycolipid, a glucolipid, a sulfatide, a glycosphingolipid, phosphatidic acid, palmitic acid, stearic acid, arachidonic acid, oleic acid, a lipid bearing a polymer, a lipid bearing a sulfonated saccharide, cholesterol, tocopherol hemisuccinate, a lipid with an ether-linked fatty acid, a lipid with an ester-linked fatty acid, a polymerized lipid, diacetyl phosphate, stearylamine, cardiolipin, a phospholipid with a fatty acid of 6-8 carbons in length, a phospholipid with asymmetric acyl chains, 6-(5-cholesten-3b-yloxy)-1-thio-b-D-galactopyranoside, digalactosyldiglyceride, 6-(5-cholesten-3b-yloxy)hexyl-6-amino-6-deoxy-1-thio-b-D-galactopyranosid-e, 6-(5-cholesten-3b-yloxy)hexyl-6-amino-6-deoxyl-1-thio-a-D-mannopyranosi-de, 12-(((7'-diethylamino-coumarin-3-yl)carbonyl)methylamino)-octadecanoic acid, N-[12-(((7'-diethylaminocoumarin-3-yl)carbonyl)methyl-amino)octadecanoyl]-2-aminopalmitic acid, cholesteryl)4'-trimethyl-ammonio)butanoate, N-succinyldioleoyl-phosphatidylethanolamine, 1,2-dioleoyl-sn-glycerol), 1,2-dipalmitoyl-sn-3-succinyl-glycerol, 1,3-dipalmitoyl-2-succinylglycerol, 1-hexadecyl-2-palmitoyl glycero-phosphoethanolamine, and palmitoylhomocysteine.

The PKC modulator according to the invention may be conjugated by any known means, for example via its amino, carboxy, S—S groups. The conjugation between the PKC modulator and the cell entering moiety may also involve a linker. Suitable linkers are known in the art. Preferably the linker is of the type that can be cleaved by intracellular enzymes this separating the modulator from the permeability moiety.

In the specification and in the claims the term "linker" denotes any chemical compound, which may be present between the permeability enhancing moiety and the peptide. Preferably, the linker may be cleaved from the peptide by chemical means, by enzymatic means, or may decompose spontaneously. The linker may be pharmacologically inert or may itself provide added beneficial pharmacological activity. The term "spacer" denoting a moiety used to allow distance between the permeability-enhancing moiety and the peptide, may also be used interchangeably as a synonym for linker.

The linker may optionally comprise a protease specific cleavable sequence. A "Protease specific cleavable sequence" denotes any peptide sequence which comprises a peptide bond cleavable by a specific protease, which is more abundant within or in proximity to the malignant cells. Non-limiting examples for protease specific cleavable sequence are described in WO 02/020715. Typically a protease specific cleavable sequence includes peptides of from about two to about fourteen amino acids comprising at least one site that is cleaved by a specific protease.

Non-limiting examples for specific biodegradable sequences that are degraded by proteases that are more abundant within or in proximity to the malignant cells are: Matrix metalloproteinases (for example collagenases, gelatinases and stromelysins); Aspartic proteases (for example cathepsin D, cathepsin E, pepsinogen A, pepsinogen C, rennin); Serine proteases (for example plasmin, tissue-type plasminogen activator (tPA), urokinase type plasminogen activator (uPA); cysteine proteases (for example cathepsin B, cathepsin L, cathepsin S); asparaginyl proteases (for example legumain).

Epithelium lines both the outside (skin) and the inside cavities and lumen of bodies. The outermost layer of our skin is composed of dead stratified squamous, keratinized epithelial cells. Tissues that line the inside of the mouth, the esophagus and part of the rectum are composed of nonkeratinized stratified squamous epithelium. Other surfaces that separate body cavities from the outside environment are lined by simple squamous, columnar, or pseudostratified epithelial cells. Other epithelial cells line the insides of the lungs, the gastrointestinal tract, the reproductive and urinary tracts, and make up the exocrine and endocrine glands. The outer surface of the cornea is covered with fast-growing, easily-regenerated epithelial cells. Endothelium (the inner lining of blood vessels, the heart, and lymphatic vessels) is a specialized form of epithelium. Another type, mesothelium, forms the walls of the pericardium, pleurae, and peritoneum. Asthma is categorized as epithelial disease (Chanez 2005, European Respiratory Journal 25, 945-946).

PKC is a major signaling pathway, which mediates keratinocyte proliferation, migration and differentiation. Many PKC isoforms are known to be expressed in skin tissue and their expression/activity appears to play a role in cell proliferation and/or cell migration and/or cell differentiation. However, their specific modulation of expression and activity to effectuate treatment of inflammatory diseases was previously unknown and is demonstrated in the present disclosure.

Overall, the results presented herein demonstrate that modulating expression and/or activity of distinct PKC isoforms is effective in treatment of inflammation and inflammatory diseases of the skin and other epithelial tissues.

Thus, in one aspect, the present disclosure provides a method of treating an inflammatory disease or disorder of the skin or epithelial tissue, in a subject. The method includes administering to the subject an inhibitor of PKC, thereby treating the inflammatory disease or disorder in the subject. In exemplary embodiments, the inhibitor is a peptide which selectively inhibits PKCα, PKCε or PKCη, such as the peptides of SEQ ID NOs: 1-13 and 18-25.

As disclosed in the Examples, administration of PKC isoform inhibitors has been shown to reduce secretion of pro-inflammatory cytokines, chemokines and Th1 cytokines in a variety of different skin cell types (not just skin cells i.e. macrophages and splenocytes that are found in other tissues). In addition, administration of PKC isoform reduces the expression of activating factors such as ICAM-1 on keratinocytes and endothelial cells and mac-2 on macrophages. Additionally, PKCα inhibitors have been found effective in the treatment of skin inflammation and to attenuate the inflammatory symptoms in inflammatory skin models of psoriasis. As discussed further in the Examples, the mechanism of action of inhibitors of PKC isoforms now elucidated implicates their use as an effective therapy for inflammatory diseases and disorders, particularly those of the skin and epithelial tissues. For example, peptide inhibitors of PKC isoforms have been shown to: 1) normalize epidermal differentiation marker expression by reducing terminal differentiation; 2) attenuate abnormal hyper-proliferation; 3) regulate skin structure and augment skin strength; and/or 4) down-regulate inflammation by differentially affecting different cell type recruitment and activation in various steps of the inflammatory process as summarized, for example, in FIG. 30 and tables 8-10.

Also, as disclosed in the Examples activators of PKCδ have also been shown to reduce secretion of pro-inflammatory cytokines in a variety of different skin cell types and immune cells affecting the skin and other cells. Thus, in another aspect, the present disclosure provides a method of treating an inflammatory disease or disorder in a subject by administering to the subject an activator of PKCδ, thereby treating the inflammatory disease or disorder in the subject. In various embodiments, the activator is a peptide which selectively activates PKCδ, such as the peptides of SEQ ID NOs: 14-17.

Further, administration of PKC isoform inhibitors has been found effective in the treatment of pruritus. As such, in another aspect, the present disclosure provides a method of treating pruritus in a subject. The method includes administering to the subject an inhibitor of PKC, thereby treating pruritus in the subject.

The Examples and Figures present data showing the ability of activators of PKCδ to inhibit the secretion of major pro-inflammatory cytokines, such as IL-1, IL-6 and TNFα. Similar data is shown for a variety of PKC isoform inhibitors, including PKCα, PKCε and PKCη. As shown in the Examples, formulations including the PKC inhibitors and activators of the present disclosure have been shown to inhibit the secretion of major pro-inflammatory cytokines. As regards psoriasis, without being bound to a particular theory, it is believed that reducing the level of pro-inflammatory agents prevents the activation of endothelial cells in near-by blood vessels, and thus the recruitment of neutrophiles, macrophages and T cells to the psoriatic plaque. Moreover, TH1 and TH17 cells were shown to be implicated in the pathogenesis of psoriasis by the secretion of specific cytokines, which appear to enhance inflammation or drive keratinocyte hyper-proliferation, respectively. The above mentioned pro-inflammatory cytokines appear essential for the development of these TH17 cells (Mangan et al. (2006) *Nature* 441:231-234; Bettelli et al. (2006) *Nature* 441:235-238) and for TH1 cell activity. The decrease of their secretion by PKC inhibitors and activators implicates their use in the effective treatment of inflammatory disorders and pruritus.

In various embodiments, the modulators of PKC isoforms are peptides or polypeptides. The terms "polypeptide", "peptide" are used interchangeably herein to designate a series of natural, non-natural and/or chemically modified amino acid residues connected one to the other by peptide (amide) or non-peptide bonds, typically between the alpha-amino and carboxy groups of adjacent residues.

Peptides according to the present invention may are typically linear but cyclic versions of the peptides disclosed herein, are also within the scope of the present invention. Cyclization of peptides may take place by any means known in the art, for example through free amino and carboxylic groups present in the peptide sequence, or through amino acids or moieties added for cyclization. Non limiting examples of cyclization types are: side chain to side chain cyclization, C-to-N terminal cyclization, side chain to terminal cyclization, and any type of backbone cyclization incorporating at least one $N^{\alpha}$-ω-substituted amino acid residue/s as described for example in WO 95/33765.

The peptides of the present invention are preferably synthesized using conventional synthesis techniques known in the art, e.g., by chemical synthesis techniques including peptidomimetic methodologies. These methods include exclusive solid phase synthesis, partial solid phase synthesis methods, fragment condensation, classical solution synthesis. Solid phase peptide synthesis procedures are well known in the art and further described by John Morrow Stewart and Janis Dillaha Young, Solid Phase Peptide Syntheses (2nd Ed., Pierce Chemical Company, 1984). A skilled artesian may synthesize any of the peptides of the present invention by using an automated peptide synthesizer using standard chemistry such as, for example, t-Boc or Fmoc chemistry. Synthetic peptides can be purified by preparative high performance liquid chromatography (Creighton T. 1983, Proteins, structures and molecular principles. WH Freeman and Co. N.Y.), and the composition of which can be confirmed via amino acid sequencing. Some of the peptides of the invention, which include only natural amino acids, may further be prepared using recombinant DNA techniques known in the art. The conjugation of the peptidic and permeability moieties may be performed using any methods known in the art, either by solid phase or solution phase chemistry. Some of the preferred compounds of the present invention may conveniently be prepared using solution phase synthesis methods. Other methods known in the art to prepare compounds like those of the present invention can be used and are comprised in the scope of the present invention.

The term "amino acid" is used in its broadest sense to include naturally occurring amino acids as well as non-naturally occurring amino acids including amino acid analogs. In view of this broad definition, one skilled in the art would know that reference herein to an amino acid includes, for example, naturally occurring proteogenic (L)-amino acids, (D)-amino acids, chemically modified amino acids such as amino acid analogs, naturally occurring non-proteogenic amino acids such as norleucine, and chemically synthesized compounds having properties known in the art to be characteristic of an amino acid. As used herein, the term "proteogenic" indicates that the amino acid can be incorporated into a protein in a cell through a metabolic pathway. The amino acids used in this invention are those which are available commercially or are available by routine synthetic methods. Certain residues may require special methods for incorporation into the peptide, and either sequential, divergent and convergent synthetic approaches to the peptide sequence are useful in this invention. When there is no indication, either the L or D isomers may be used.

Conservative substitution of amino acids as known to those skilled in the art are within the scope of the present invention. Conservative amino acid substitutions includes replacement of one amino acid with another having the same type of functional group or side chain e.g. aliphatic, aromatic, positively charged, negatively charged. These substitutions may enhance oral bioavailability, affinity to the target protein, metabolic stability, penetration into the central nervous system, targeting to specific cell populations and the like. One of skill will recognize that individual substitutions, deletions or additions to peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art.

The following six groups each contain amino acids that are conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), methionine (M), Valine (V); and
6) Phenylalanine (F), Tyrosine (Y), Tryptophan (W).

Also included within the scope of the invention are salts of the peptides, analogs, and chemical derivatives of the peptides of the invention.

As used herein the term "salts" refers to both salts of carboxyl groups and to acid addition salts of amino or guanido groups of the peptide molecule. Salts of carboxyl groups may be formed by means known in the art and include inorganic salts, for example sodium, calcium, ammonium, ferric or zinc salts, and the like, and salts with organic bases such as salts formed for example with amines such as triethanolamine, piperidine, procaine, and the like. Acid addition salts include, for example, salts with mineral acids such as, for example, acetic acid or oxalic acid. Salts describe here also ionic components added to the peptide solution to enhance hydrogel formation and/or mineralization of calcium minerals.

A "chemical derivative" as used herein refers to peptides containing one or more chemical moieties not normally a part of the peptide molecule such as esters and amides of free carboxy groups, acyl and alkyl derivatives of free amino groups, phospho esters and ethers of free hydroxy groups. Such modifications may be introduced into the molecule by reacting targeted amino acid residues of the peptide with an organic derivatizing agent that is capable of reacting with selected side chains or terminal residues. Preferred chemical derivatives include peptides that have been phosphorylated, C-termini amidated or N-termini acetylated.

"Functional derivatives" of the peptides of the invention as used herein covers derivatives which may be prepared from the functional groups which occur as side chains on the residues or the N- or C-terminal groups, by means known in the art, and are included in the invention as long as they remain pharmaceutically acceptable, i.e., they do not destroy the activity of the peptide, do not confer toxic properties on compositions containing it and do not adversely affect the antigenic properties thereof. These derivatives may, for example, include aliphatic esters of the carboxyl groups, amides of the carboxyl groups produced by reaction with ammonia or with primary or secondary amines, N-acyl derivatives of free amino groups of the amino acid residues formed by reaction with acyl moieties (e.g., alkanoyl or carbocyclic aroyl groups) or O-acyl derivatives of free hydroxyl group (for example that of seryl or threonyl residues) formed by reaction with acyl moieties.

The term "peptide analog" indicates molecule which has the amino acid sequence according to the invention except for one or more amino acid changes or one or more modification/replacement of an amide bond. Peptide analogs include amino acid substitutions and/or additions with natural or non-natural amino acid residues, and chemical modifications which do not occur in nature. Peptide analogs include peptide mimetics. A peptide mimetic or "peptidomimetic" means that a peptide according to the invention is modified in such a way that it includes at least one non-coded residue or non-peptidic bond. Such modifications include, e.g., alkylation and more specific methylation of one or more residues, insertion of or replacement of natural amino acid by non-natural amino acids, replacement of an amide bond with other covalent bond. A peptidomimetic according to the present invention may optionally comprises at least one bond which is an amide-replacement bond such as urea bond, carbamate bond, sulfonamide bond, hydrazine bond, or any other covalent bond. The design of appropriate "analogs" may be computer assisted. Additional peptide analogs according to the present invention comprise a specific peptide or peptide analog sequence in a reversed order, namely, the amino acids are coupled in the peptide sequence in a reverse order to the amino acids order which appears in the native protein or in a specific peptide or analog identified as active. Whether completely or partially non-peptide, peptidomimetics according to this invention provide a spatial arrangement of chemical moieties that closely resembles the three-dimensional arrangement of groups in the peptide on which the peptidomimetic is based. As a result of this similar active-site structure, the peptidomimetic has effects on biological systems, which are similar to the biological activity of the peptide.

A modified amino acid residue is an amino acid residue in which any group or bond was modified by deletion, addition, or replacement with a different group or bond, as long as the functionality of the amino acid residue is preserved or if functionality changed (for example replacement of tyrosine with substituted phenylalanine) as long as the modification did not impair the activity of the peptide containing the modified residue.

Peptide PKC inhibitors or activators may have modified amino acid sequences or non-naturally occurring termini modifications. Modifications to the peptide sequence can include, for example, additions, deletions or substitutions of amino acids, provided the peptide produced by such modifications retains PKCα inhibitory activity. Additionally, the peptides can be present in the formulation with free termini or with amino-protected (such as N-protected) and/or carboxy-protected (such as C-protected) termini. Protecting groups include: (a) aromatic urethane-type protecting groups which include benzyloxycarbonyl, 2-chlorobenzyloxycarbonyl, 9-fluorenylmethyloxycarbonyl, isonicotinyloxycarbonyl and 4-methoxybenzyloxycarbonyl; (b) aliphatic urethane-type protecting groups which include t-butoxycarbonyl, t-amyloxycarbonyl, isopropyloxycarbonyl, 2-(4-biphenyl)-2-propyloxycarbonyl, allyloxycarbonyl and methylsulfonylethoxycarbonyl; (c) cycloalkyl urethane-type protecting groups which include adamantyloxycarbonyl, cyclopentyloxycarbonyl, cyclohexyloxycarbonyl and isobornyloxycarbonyl; (d) acyl protecting groups or sulfonyl protecting groups. Additional protecting groups include benzyloxycarbonyl, t-butoxycarbonyl, acetyl, 2-propylpentanoyl, 4-methylpentanoyl, t-butylacetyl, 3-cyclohexylpropionyl, n-butanesulfonyl, benzylsulfonyl, 4-methylbenzenesulfonyl, 2-naphthalenesulfonyl, 3-naphthalenesulfonyl and 1-camphorsulfonyl.

According to some embodiments the amino terminus of the peptide is modified, e.g., it may be acylated. In particular embodiments, the peptide PKC inhibitors or activators are N-acylated by an acyl group. According to some embodiments, the acyl group is derived from a C4-C24 fatty acid. According to particular embodiments the acyl group is derived from a C12-C20 fatty acid, such as C1-4 acyl (myristoyl) or C1-6 acyl (palmitoyl).

According to additional embodiments the carboxy terminus is modified, e.g., it may be amidated, reduced to alcohol or esterified.

In various embodiments, Examples of peptide PKC activators and inhibitors that can be used include, without being limited to, peptides of SEQ ID NOs: 1-17 as shown in Table 1 or analogs, derivatives or physiologically acceptable salts thereof, as well as the peptides of SEQ ID NOs: 18-25 of Table 1 which comprises a permeability moiety, particular modifications or terminal protecting groups.

In various embodiments, the peptide PKC inhibitors or activators typically contain between 5-25 amino acids, or 6 and 12 amino acids, but may be longer or shorter in length. In various embodiment a peptide PKC inhibitor or activator may range in length from 6 to 45, 6 to 40, 6 to 35, 6 to 30, 6 to 25, 6 to 20, 6 to 15, or 6 to 10 amino acids. In one embodiment the peptide includes 6, 7, 8, 9, 10, 11, 12, 13, 14 or 15 amino acids.

In general, peptide PKCα inhibitors include the common motif sequence Phe-Ala-Arg-Lys-Gly-Ala (SEQ ID NO: 1), alternatively, in another embodiment, PKCα inhibitors include the common motif sequence Thr-Leu-Asn-Pro-Gln-Trp-Glu-Ser (SEQ ID NO: 5).

A "peptide-multimer" according to the present invention refers to a construct comprising at least two, covalently linked, peptides. The at least two peptides may be identical or different and may be modulators of same or different PKC isoform. A peptide-multimer may further include a permeability moiety and/or N or C terminal modifications.

While the peptide PKC inhibitors and activators may be defined by exact sequence or motif sequences, one skilled in the art would understand that peptides that have similar sequences may have similar functions. Therefore, peptides having substantially the same sequence or having a sequence that is substantially identical or similar to a PKC inhibitor or activator of Table 1 are intended to be encompassed. As used herein, the term "substantially the same sequence" includes a peptide including a sequence that has at least 60+% (meaning sixty percent or more), preferably 70+%, more preferably 80+%, and most preferably 90+%, 95+%, or 98+% sequence identity with the sequences defined by SEQ ID NOs: 1-25 and inhibit or activate PKC isoform activity.

A further indication that two peptides are substantially identical is that one peptide is immunologically cross reactive with that of the second. Thus, a peptide is typically substantially identical to a second peptide, for example, where the two peptides differ only by conservative substitutions.

The terms "identical" or percent "identity" in the context of two peptide sequences, refer to two or more sequences or subsequences that are the same or have a specified percentage of amino acid residues that are the same, when compared and aligned for maximum correspondence, as measured using a sequence comparison algorithm or by visual inspection.

The phrase "substantially identical," in the context of two polypeptides, refers to two or more sequences or subsequences that have at least 60+%, preferably 80+%, most preferably 90-95+% amino acid residue identity, when compared and aligned for maximum correspondence, as measured using a sequence comparison algorithm or by visual inspection.

As is generally known in the art, optimal alignment of sequences for comparison can be conducted, for example, by the local homology algorithm of Smith & Waterman ((1981) *Adv Appl Math* 2:482), by the homology alignment algorithm of Needleman & Wunsch ((1970) *J Mol Biol* 48:443), by the search for similarity method of Pearson & Lipman ((1988) *Proc Natl Acad Sci USA* 85:2444), by computerized implementations of these algorithms by visual inspection, or other effective methods.

In various embodiments, peptide PKC isoform inhibitors and activators may be administered by any suitable means, including topical, parenteral, subcutaneous, intraperitoneal, intrapulmonary, intranasal, intravenous, and/or intralesional administration in order to treat the subject. However, in exemplary embodiments, the peptides are formulated for topical application, such as in the form of a liquid, cream, gel, ointment, foam spray or the like.

Therapeutic formulations of the PKC isoform inhibitor or activator used in accordance with the present disclosure are prepared, for example, by mixing a PKC isoform inhibitor or activator having the desired degree of purity with optional pharmaceutically acceptable carriers, excipients and/or stabilizers (see, for example: Remington's Pharmaceutical Sciences, 16th edition, Osol, A. Ed. (1980)). Acceptable carriers, excipients, or stabilizers are nontoxic to recipients at the dosages and concentrations employed, and may include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (for example, Zn-protein complexes); and/or non-ionic surfactants such as TWEEN™, PLURONICS™ or polyethylene glycol (PEG).

In exemplary embodiments, the PKC isoform inhibitor or activator, are formulated in a cream. The inhibitors and activators of PKC isoforms are ideal for topical treatment of skin inflammation and other inflammatory disorders since the activity of PKC enzymes, may be specifically targeted. Inhibition or activation of specific PKC enzymes is achieved by the ability to selectively modulate a PKC isoform in lower concentrations, without affecting other PKC isoforms.

An exemplary formulation for topical administration is disclosed in Example 4, in which the peptide designated MPDY-1 (SEQ ID NO: 6) is formulated as a cream for topical administration. However, one skilled in the art would understand that alterations of the formulation may be made while retaining the essential characteristics of the cream, such as viscosity, stabilization, non-toxicity and the like. Also, one skilled in the art would recognize that the formulation may be used as a vehicle for any of the peptide PKC inhibitors or activators of the present disclosure.

In another embodiment, an article of manufacture, such as a kit containing materials useful for carrying out the treatment method of the disclosure is provided. In various embodiments, the kit includes a PKC isoform activator or inhibitor, namely a peptide PKC isoform inhibitor or activator as disclosed herein, and instructions for administering the activator or inhibitor to the subject.

The term "instructions" or "package insert" is used to refer to instructions customarily included in commercial packages of therapeutic products, that contain information about the indications, usage, dosage, administration, contraindications, other therapeutic products to be combined with the packaged product, and/or warnings concerning the use of such therapeutic products, and the like.

As disclosed herein, the modulator of PKC may be formulated for a specific route of administration. As such, the kit may include a formulation including a modulator of PKC that is contained in a suitable container, such as, for example, tubes, bottles, vials, syringes, and the like. The containers may be formed from a variety of materials such as glass or plastic. The container holds or contains a composition that is effective for treating the inflammatory skin/epithelial disease and may have a sterile access port (for example the container may be an intravenous solution bag or a vial having a stopper pierceable by a hypodermic injection needle). At least one component in the formulation is an inhibitor or activator of a PKC isoform. The label or package insert indicates that the composition is used for treating inflammatory skin/epithelial disease in a subject suffering therefrom with specific guidance regarding dosing amounts and intervals for providing the formulation including an inhibitor or activator of a PKC isoform. The article of manufacture may further include other materials desirable from a commercial and user standpoint, including other buffers, diluents, filters, needles, and syringes.

It will be understood, that the specific dose level and frequency of dosage for any particular subject in need of treatment may be varied and will depend upon a variety of factors including the activity of the PKC isoform inhibitor or activator employed, the metabolic stability and length of action of that compound, the age, body weight, general health, sex, diet, mode and time of administration, the severity of the particular condition, and the host undergoing therapy. Generally however, dosage will approximate that which is typical for known methods of administration of the specific PKC isoform inhibitor or activator. Persons of skill in the art can easily determine optimum dosages, dosing methodologies and repetition rates. The exact formulation and dosage can be chosen by the individual physician in view of the patient's condition (Fingl et al. "The Pharmacological Basis of Therapeutics", Ch. 1 p. 1 (1975)).

Thus, depending on the severity and responsiveness of the condition to be treated, dosing can be a single or repetitive administration, with course of treatment lasting from several days to several weeks or until cure is effected or diminution of the disorder is achieved.

In particular embodiments, the PKC isoform inhibitor or activator peptide is provided in the composition at a concentration of between 0.001 and 100 µg/ml. For example, the concentration may be between 0.001 and 100, 0.01 and 50, 0.01 and 10, 0.01 and 1, and 0.01 and 0.5 µg/ml.

In one exemplary dosing protocol, the method comprises administering a peptide PKC isoform inhibitor or activator to the subject topically, for example as a cream or gel. The peptide is topically applied at a concentration of from about 1 µg/ml to about 1000 µg/ml, 1 µg/ml to about 500 µg/ml, 1 mg/ml to about 100 µg/ml, 1 µg/ml to about 10 µg/ml, or 10 µg/ml to about 100 µg/ml. The peptide is administered at least once daily until the condition is treated.

In another dosing protocol, the method comprises administering a peptide PKC isoform inhibitor or activator to the subject parentally, subcutaneously or intravenously. The peptide is applied in a concentration of from about 1 µg/ml to about 1000 µg/ml, 1 µg/ml to about 500 µg/ml, 1 µg/ml to about 100 µg/ml, 1 µg/ml to about 10 µg/ml, or 10 µg/ml to about 100 µg/ml. The peptide is administered at least once daily, weekly, biweekly, or monthly until the condition is treated.

The following examples are provided to further illustrate the embodiments of the present disclosure, but are not intended to limit the scope. While they are typical of those that might be used, other procedures, methodologies, or techniques known to those skilled in the art may alternatively be used.

Example 1

Figure 2:
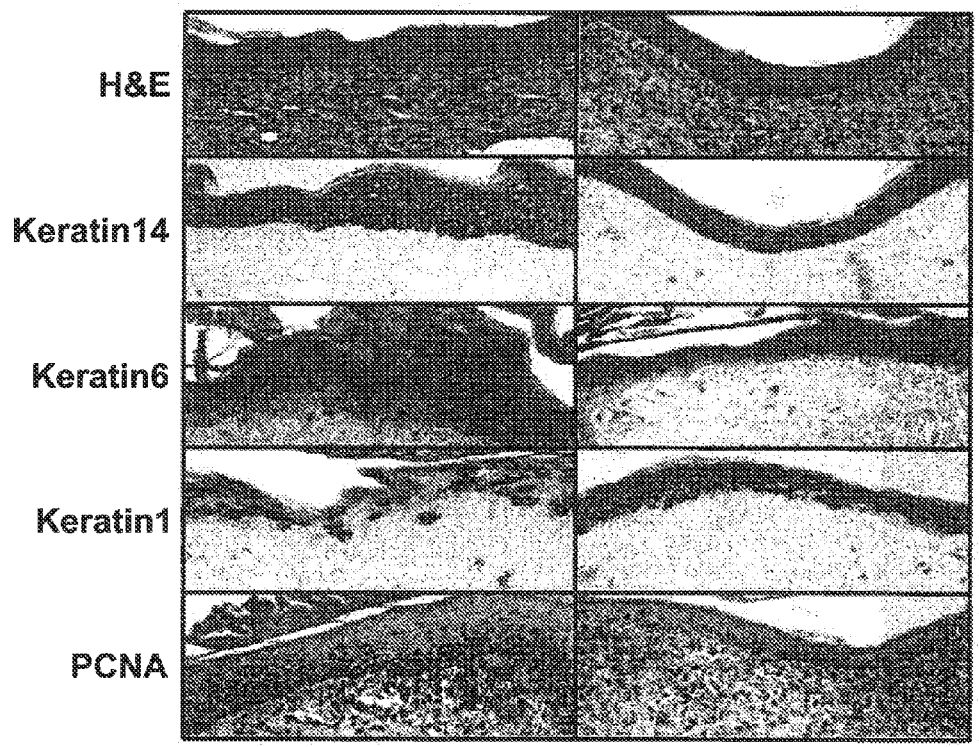
FIG. 2 is a series of pictorial representations depicting inhibition of PKCα which regulates keratinocytes structure integrity characteristic to psoriasis. Skin tissues were paraffin embedded and stained for hematoxiline and eosine (H&E) general histological staining or distinct markers for the various skin layers including Keratin 14 (K14) for basal layer, Keratin 1 (K1) for spinous layer, Keratin 6 (K6) for keratinocytes migration and skin proliferation cell nuclear antigen (PCNA) for keratinocytes proliferation. The results demonstrate normalization of skin properties following PKCα inhibition (left column is WT, right column is PKCα knock out).

Inhibition of PKCα Regulates Keratinocyte Structure Integrity Characteristic to Inflammatory Skin Disorder Psoriasis Inhibition of PKCα was shown to regulate keratinocyte structure integrity characteristic to psoriasis. Skin tissues were paraffin embedded and stained for H&E (hematoxiline and eosine) general histological staining or for distinct markers for the various skin layers including Keratin 14 (K14) for basal layer, Keratin 1 (K1) for spinous layer, Keratin 6 (K6) for keratinocytes migration and PCNA for keratinocytes proliferation. The results demonstrate normalization of skin properties following PKCα inhibition by knockout (FIG. 2).

Example 2

Models for Assessing In Vivo and Ex Vivo Treatment of Inflammation Via Psoriasis Models Numerous animal models have been previously used to study psoriasis, however, none of these models were sufficient to adequately mimic the human disease pathology characterized by excessive skin production, formation of new blood vessels, and severe immune dysfunction. In general, to be considered as a useful model of psoriasis, the model has to share some histopathology features with psoriasis, exhibit similar pathogenesis and/or disease mechanism, and respond similarly to therapeutic agents for the treatment of the disease. Existing models exhibit several characteristics including acanthosis, altered epidermal differentiation, increase in vascularization, and Leukocytic/T cell infiltration. However, among the existing mice models, not many respond to existing drugs and therapies. As such, existing models were used to develop new in-vitro, ex-vivo and in-vivo models to assess psoriasis treatment which were utilized in the following Examples.

In Vitro Models

Developed models included cell culture studies using cell lines and primary cultures of skin-derived cells as well as immune cells, utilizing constructs and tools to over-express and inactivate STAT3 and PKCα mediated signaling pathways. A vast set of techniques for the study of skin cell proliferation, migration, differentiation, inflammation and signaling were utilized and proved useful in studying the mechanism of psoriasis development and to study the therapeutic effect of PKCα inhibition in psoriasis.

In Vivo Models

A PKCα over-expressing and knockout mouse models were used. Over-expression of PKCα in keratinocytes using a K5-PKCα transgenic mice, was shown to exhibit severe intra-epidermal neutrophil infiltration and disruption of the epidermis that mimic conditions such as pustular psoriasis. Both PKCα and dominant negative (DN) forms of transgenic mice were established which were studied in vivo by sub-dermal application. In addition, PKCα knockout mice are also used to study the effects of PKCα inactivation on skin structure and function.

A STAT3 over-expressing mouse model used. Among the leading mice models for psoriasis, in terms of similarity to human psoriasis, is a transgenic mouse in which Stat3, is over-expressed in epidermal keratinocytes. These mice, develop psoriasiform epidermal acanthosis and have a cutaneous lymphocytic infiltrate that is predominantly CD4+ in the dermis, and CD8+ in the epidermis, all are features that are similar to psoriasis in human.

Wound as a model for skin inflammation and hyperplasia. A screening methodology was developed to detect and quantitatively assess inflammation in skin lesions in a wound setting which allows to follow cutaneous inflammatory response in the different skin compartments and identify agents that affect this response.

Ex Vivo Models

Psoriatic skin grafting on Chick Chorioalantoic Membrane (CAM). A technique of psoriatic skin grafting on CAM was developed for the purpose of testing ex-vivo treatment applications. While this technique is commonly used for skin tumor studies and angiogenesis experiments, it was adopted and used for psoriasis studies. This original approach allows the application of new drugs directly on human psoriatic skin, thus creating a more clinically relevant study of new drugs for the treatment of psoriasis. Following grafting, psoriatic human skin is utilized to establish efficacy and timing of various treatments in various formulations, analyzed using morphological, histological and biochemical analysis.

Example 3

Attenuation of Scaling in PKCα Knock Out Mice

A PKCα knockout mouse model was developed and utilized to study the effects of PKCα inactivation on skin structure and function. The fur on the back of the mice was trimmed and shaved. The Middle back section of the mice were treated daily by application of 62 mg of Imiquimod for 8 days. Mice were monitored daily for erythema and scales.

Figure 3:
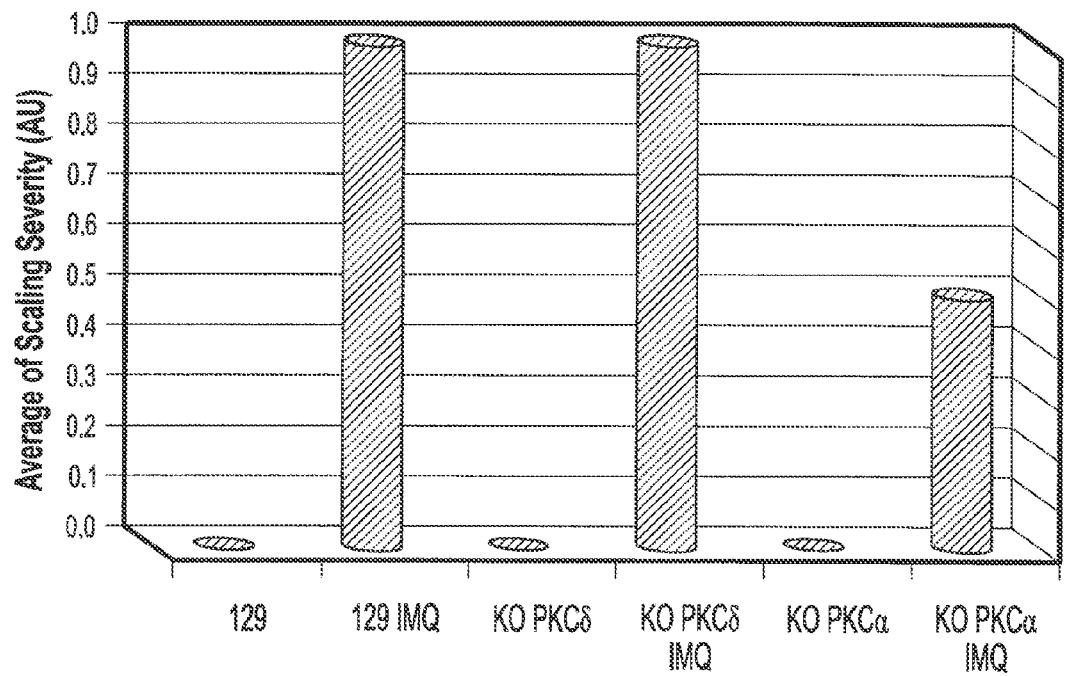
FIG. 3 is a histogram comparing severity of scaling in different knock out mice as compared to control after treatment with the anti cancer agent Imiquimod.
Figures 4A, 4B, 4C:
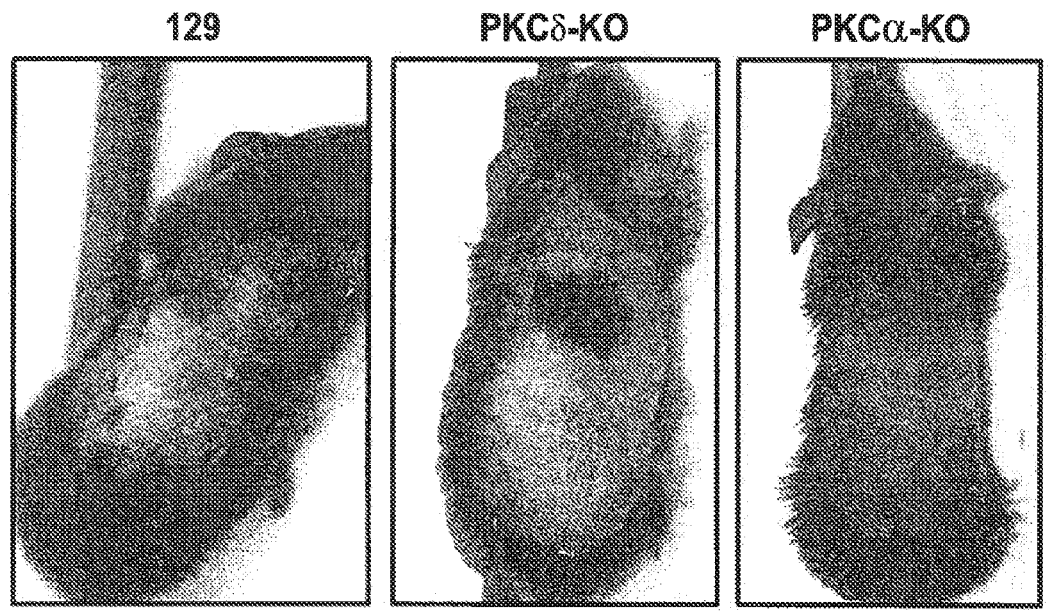
FIGS. 4A-4C are a series of pictorial representations showing scaling in knock out mice as compared with control after treatment with Imiquimod.

FIG. 3 is a histogram showing that the average scaling severity was reduced by over 50% in PKCα knock out mice as compared to control evidencing that inhibition of PKCα is a key requirement in treating psoriasis. As shown in FIG. 3, attenuation of scaling was observed in PKCα knock out mice. This is also shown in FIG. 4, which is a series of pictures comparing scaling in different mice.

Example 4

Topical PKCα Inhibitor Formulation

A topical PKCα inhibitor formulation was developed and assessed for effectiveness in treatment of psoriasis. The peptide PKCα inhibitor MPDY-1 (SEQ ID NO: 21) was formulated in a cream (referred to herein as HO/02/10), the components of which are shown in Table 2.

TABLE 2

HO/02/10 Cream Based Formulation

| INGREDIENTS | |
| --- | --- |
| Water | 50%-80% |
| Glycerine | 2%-10% |
| Propylene Glycol | 2%-20% |
| Methylparaben | 0.2%-0.5% |
| Phenoxyethanol | 0.5%-1% |
| Glyceryl Stearate SE | 2%-12% |
| Cetyl Alcohol | 3%-10% |
| Cosbiol | 2%-10% |
| PEG-40 Stearath | 0.5%-5% |
| Sucrose Distearate | 0.2%-5% |
| Isopropyl Myristate | 3%-10% |
| Butylated Hydroxy Toluene | 0.02%-0.1% |
| Paraffin Oil | 1%-10% |
| Capric/Caprylic Triglyceride | 1%-10% |
| VASELINE ®, petroleum jelly | 1%-15% |
| Propylparaben | 0.2%-0.5% |
| MPDY-1 | 10-1000 ppm |

Additional Cream formulations developed for administering the peptides in the methods of the invention are described in Tables 3 and 4:

TABLE 3

Additional topical cream formulation

| INGREDIENTS | |
| --- | --- |
| Water | 50%-80% |
| Glycerine | 2%-10% |
| Propylene Glycol | 2%-20% |
| Methylparaben | 0.2%-0.5% |
| Phenoxyethanol | 0.5%-1% |
| Glyceryl Stearate SE | 2%-12% |
| Cetyl Alcohol | 3%-10% |
| Cosbiol | 2%-10% |
| PEG-40 Stearath | 0.5%-5% |
| Sorbitan monostearate | 0.2%-5% |
| Isopropyl Myristate | 3%-10% |
| Butylated Hydroxy Toluene | 0.02%-0.1% |
| Paraffin Oil | 1%-10% |
| Capric/Caprylic Triglyceride | 1%-10% |
| VASELINE ®, petroleum jelly | 1%-15% |
| Propylparaben | 0.2%-0.5% |
| Active peptide | 10-1000 ppm |

TABLE 4

Additional topical cream formulation

INGREDIENTS

| | |
|---|---|
| Water | 50%-80% |
| Glycerine | 2%-10% |
| Propylene Glycol | 2%-20% |
| Methylparaben | 0.2%-0.5% |
| Phenoxyethanol | 0.5%-1% |
| Glyceryl Stearate SE | 2%-12% |
| Cetyl Alcohol | 3%-10% |
| Cosbiol | 2%-10% |
| PEG-40 Stearath | 0.5%-5% |
| Sorbitan monostearate | 0.2%-5% |
| 2-octyldodecanol | 3%-12% |
| Butylated Hydroxy Toluene | 0.02%-0.1% |
| Paraffin Oil | 1%-10% |
| Capric/Caprylic Triglyceride | 1%-10% |
| VASELINE ®, petroleum jelly | 1%-15% |
| Propylparaben | 0.2%-0.5% |
| Active peptide | 10-1000 ppm |

Gel formulations are described in tables 5 and 6:

TABLE 5

Exemplary gel formulation

| Ingredient | percent |
|---|---|
| Water | 70-90% |
| Disodium EDTA | 0.1-0.3% |
| Allantoin | 0.05-2% |
| Glycerin | 2.5-15% |
| Propylene glycol | 2-20% |
| Methylparaben | 0.05-0.5% |
| Carbomer1342 | 0.3-15% |
| DMDMH hydantion | 0.1-1% |
| Tea | 0.2-2% |

TABLE 6

Additional gel formulation

| Ingredient | percent |
|---|---|
| Acetate buffer (pH = 5.6) | 70-90% |
| Disodium EDTA | 0.1-0.3% |
| Allantoin | 0.05-2% |
| Glycerin | 2.5-15% |
| Propylene glycol | 2-20% |
| Methylparaben | 0.05-0.5% |
| Carbomer1342 | 0.3-15% |
| DMDMH hydantion | 0.1-1% |
| Tea | 0.2-2% |
| Lactic acid | 0.02-5% |
| Urea | 2-15% |

Example 5

Effect of PKCα Inhibitors on In Vitro Epidermal Differentiation

The HO/02/10 formulation, comprising the PKC epsilon peptide inhibitor of SEQ ID NO:21, described in Example 4 was determined to control epidermal differentiation in vitro. Basal keratinocytes differentiate to form the spinous layer, characterized by K1/K10 keratins, the granular layer that is characterized by Loricrin/Filaggrin and the stratum corneum. Defects in expression and incorporation of Loricrin and Filaggrin filaments are associated with various immunological skin diseases including psoriasis. Thus, the effects of HO/02/10, were assessed on skin differentiation and proliferation. As shown in FIGS. 5 and 6, HO/02/10 normalized skin proliferation (PCNA) (FIG. 6) and regulated skin differentiation by reducing the expression of Loricrin and Filaggrin, while spinous layer remained unaffected (FIG. 5). Since psoriatic skin keratinocytes differentiate rapidly to produce granular and mainly large amounts of corneal cells (scales), while the spinous layer thins, HO/02/10 served to normalize psoriatic skin by amending the skin characteristics toward a normal phenotype.

FIG. 5 shows that HO/02/10 controls epidermal granular differentiation in vitro. Keratinocytes derived from C57BL/6J mice were incubated in medium containing $Ca^{2+}$ to induce keratinocytes differentiation. Cells were then incubated in the presence of 1-10/02/10 (1 µg/ml). Cells were harvested, run on SDS PAGE gel and immunoblotted using anti-Filaggrin (Fil), anti Loricrin (Lor) and anti-Keratin 1 (K1) antibody.

Figure 6A:
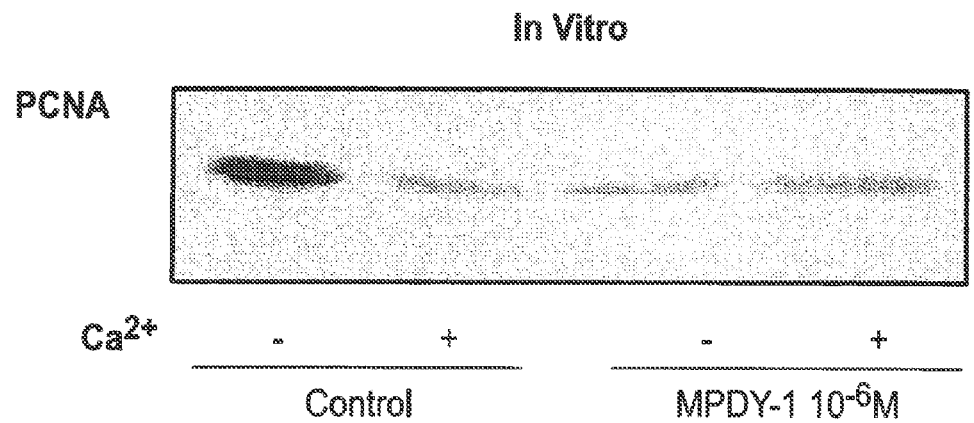
FIGS. 6A and 6B are a series of pictorial and graphical representations assessing keratinocytes proliferation in vitro and in vivo.
Figure 6B:
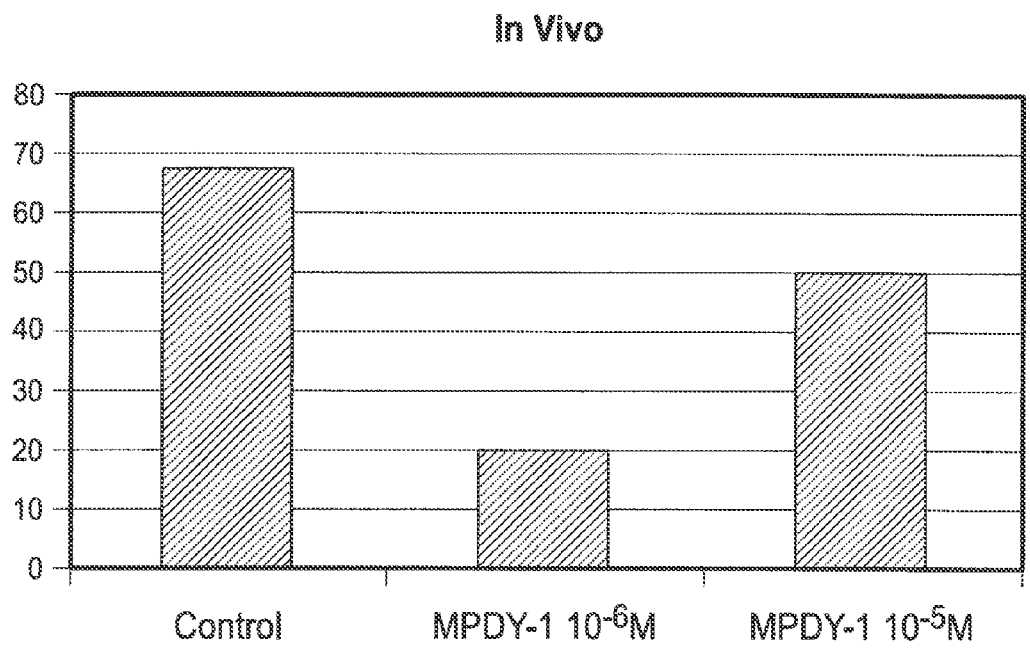

FIG. 6 shows that HO/02/10 reduced keratinocytes proliferation in vitro and in vivo. Primary murine keratinocytes from 2 days old Balb/c mice were grown for 5 days to reach full confluence in 0.05 mM $Ca^{2+}$ MEM medium. HO/02/10 treatment ($10^{-6}$M and $10^{-5}$M) was applied 6 hours prior to induction of differentiation. Cells were harvested, run on SDS PAGE gel and immunoblotted using anti-PCNA antibodies. Results are shown in FIG. 6A. In addition, C57Black mice, 8-10 weeks of age were subjected to full thickness wounding in the upper back area to induce epidermis remodeling and differentiation. Following the wounding, mice were treated daily with HO/02/10 (ranged 40-4000 mg/kg/day) for 7 days. At the termination point, mice were euthanized and upper back skin samples were fixed in 4% paraformaldehyde solution, following paraffin embedding and slide preparation. Skin samples were then subjected to immunohistochemical staining utilizing PCNA antibody. (n=18). The results are shown in FIG. 6B.

Figures 7A, 7B, 8:
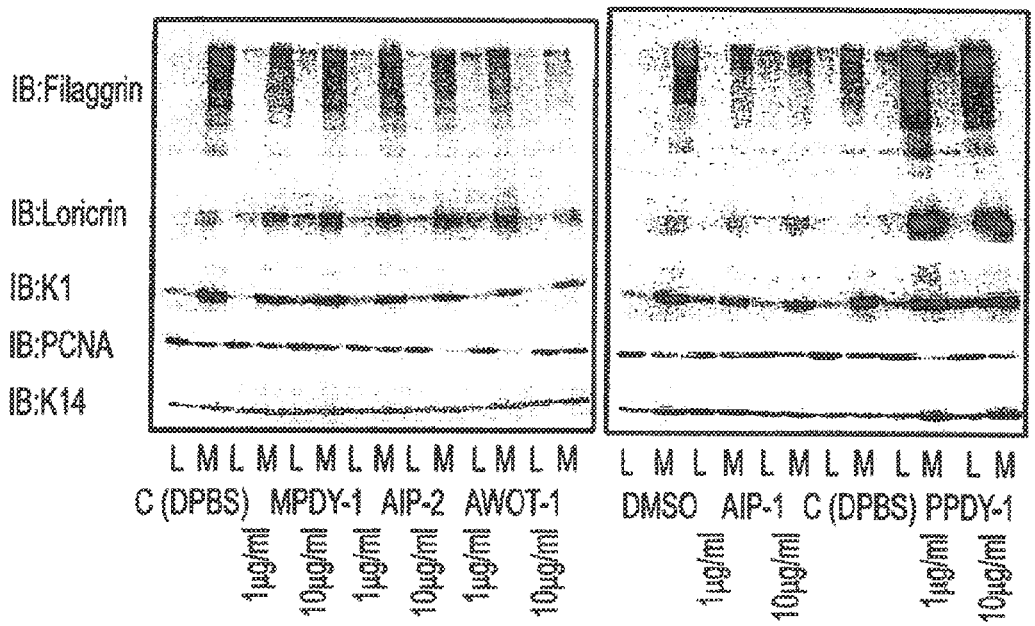
FIGS. 7A-7B are a series of pictorial representations showing expression of Filaggrin (Fil), Loricrin (Lor), Keratin 1 (K1), PCNA and Keratin 14 (K14).
FIG. 8 is graphical representation presenting a summary of protein expression data in keratinocytes for various peptide PKCα inhibitors.

FIGS. 7 and 8 presents a summary of expression data in keratinocytes utilizing various peptide PKCα inhibitors: MPDY-1 (SEQ ID NO: 21) as well as data for the peptide PKCα inhibitors AIP-1 (SEQ ID NO: 3), AIP-2 (SEQ ID NO: 20), AWOT-1 (SEQ ID NO: 5) and PPDY-1 (SEQ ID NO: 22). FIG. 7 shows immunohistochemical staining utilizing anti-PCNA, anti-Filaggrin (Fil), anti-Loricrin (Lor), anti-Keratin 1 (K1) and anti-Keratin 14 (K14) antibody in keratinocytes treated with various peptide PKCα inhibitors. FIG. 8 presents a summary of expression data in keratinocytes for various peptide PKCα inhibitors.

In order to test skin strength and elasticity, a bursting chamber was used to measure the pressure that required for skin samples to burst (a measurable indicator of skin elasticity and durability). The results in FIG. 9, demonstrate that HO/02/10 treated skin exhibited enhanced skin strength. Thus, inhibition of PKCα may be beneficial to psoriatic skin as it was shown to enhance skin integrity and prevent bursting of psoriatic lesions.

Figure 9:
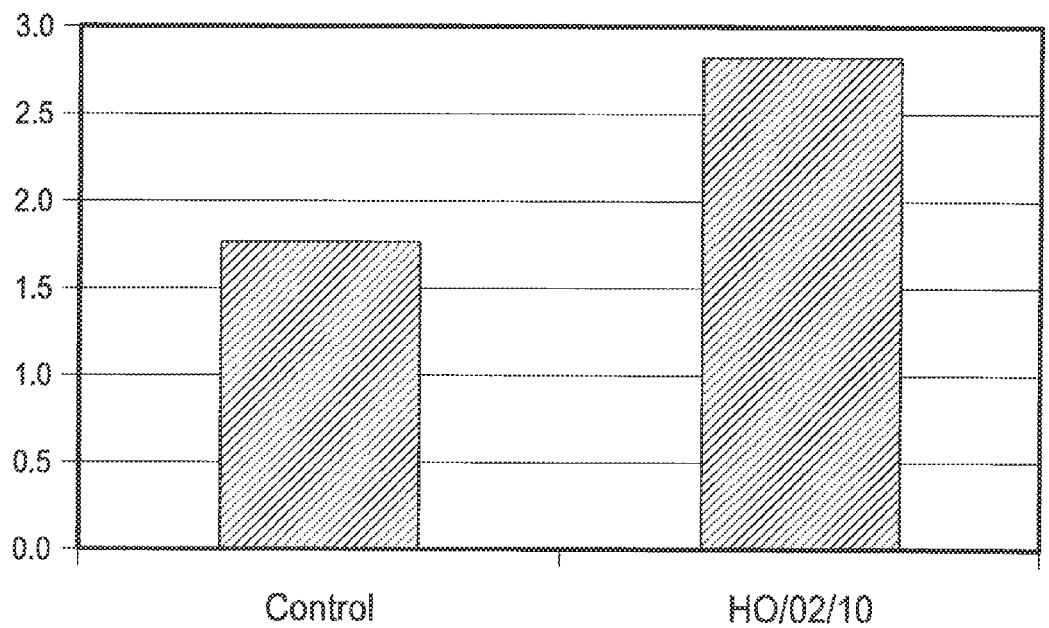
FIG. 9 is a histogram comparing the bursting pressure of skin samples treated with HO/02/10 and control.

FIG. 9 shows that HO/02/10 dramatically enforced skin strength. Mice skin was treated for 14 days with HO/02/10 and subsequently was subjected to bursting pressure analysis. The bursting chamber device consisted of a fixed volume metal cylinder closed on one end and connected to a high-pressure $CO^2$ container via a control valve and a manometer. On the other end of the chamber, an adjustable frame was installed in order to mount and hold the tested skin tissue in place. Gas was gradually released into the chamber, and the pressure inside was continuously monitored until bursting of the tested tissue occurs.

Example 6

Effect of PKC Isoform Inhibitors and Activators on Skin Inflammation

A methodology was developed to detect and quantitatively assess inflammation in skin lesions in a wound setting which allows one to follow cutaneous inflammatory response in the different skin compartments and identify agents that affect this response (as a preliminary screening). Inflammatory response was considered severe when two of the following three conditions were evident: (1) abscess formation; (2) excessive leukocytosis (>100 cells in a fixed field×200); (3) high WBC/RBC ratio in blood vessels, where >20% of WBC content within the blood vessels is shown in a fixed field×200. Mechanistic characterization of the immunological response is studied utilizing markers to identify infiltration and activation of specific immunological cells. Examples for such markers are: ICAM-1 (as a marker activated basal keratinocytes and endothelial cells), MAC-2 (as a marker for activated macrophages) and CD3 (T cell marker). Using this quantitative method, it was possible to demonstrate a strong anti-inflammatory effect of HO/02/10 and other peptide PKCα inhibitors in intact skin and in skin lesions in different cell types and processes in several animal models.

Figure 10:
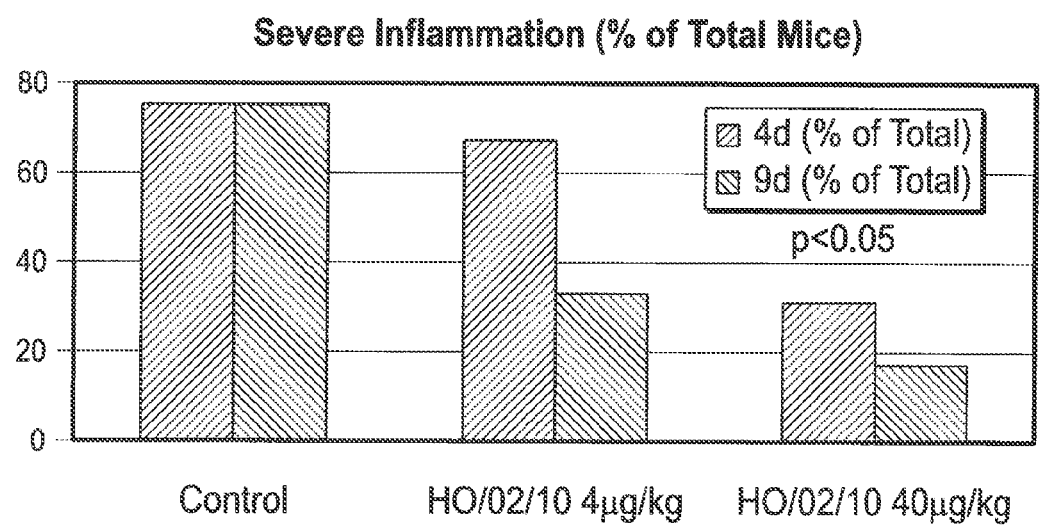
FIG. 10 is a histogram comparing the anti-inflammatory effect of HO/02/10 on skin wound in B57BL/6J mice after 4 and 9 days post wounds.

The representative results below demonstrate the anti-inflammatory effect of HO/02/10 on skin wound in B57BL/6J mice after 4 and 9 days post wounds. FIG. 10 shows the dose response of HO/02/10 effects on inflammation in C57BL/6J mice. Skins of C57BL/6J mice were treated daily by application of HO/02/10 (4 μg/kg/day) or (40 μg/kg/day) (6 mice/group). Treatments were applied topically. Biopsies were collected 4 and 9 days post-wounding. Tissues were excised from euthanized animals for evaluation of inflammation by histology and immunohistochemistry.

HO/02/10 was also shown to decrease pro-inflammatory cytokine secretion from LPS-activated splenocytes. In order to assess general anti-inflammatory effects in vitro, mice-derived primary splenocytes were utilized as an immunological model. Splenocytes were derived from C57BL/6J mice, red blood cells were lysed and cells were incubated at 500,000 per well in a 96 well plate. LPS was added (1 μg/ml for IL-1 and TNFα test, and 0.2 ng/ml for IL-6 test), and cells were treated with MPDY-1 (1 μg/ml) or PBS. No LPS was added in negative control samples. Medium was collected after 2 days and the amount of secreted cytokines was quantified using ELISA.

Figure 11:
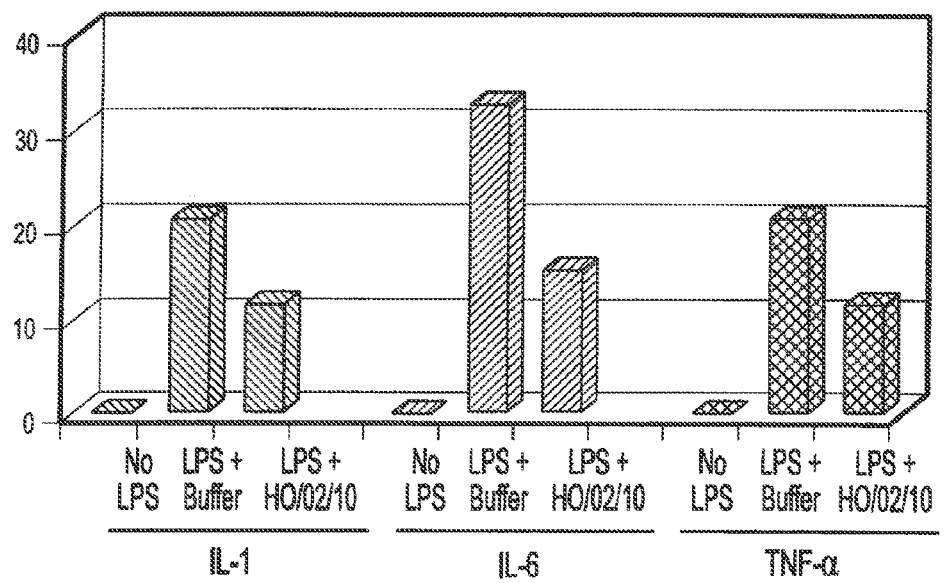
FIG. 11 is a histogram comparing cytokine secretion in splenocytes treated with HO/02/10.
Figure 12A:
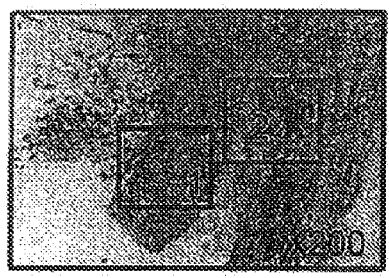
FIGS. 12A-12F are a series of pictorial representations showing ICAM expression in basal keratinocytes and endothelial cells in blood vessels of the skin, following treatment with HO/02/10.
Figure 12B:
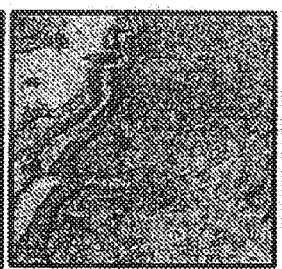
Figure 12C:
Figure 12D:
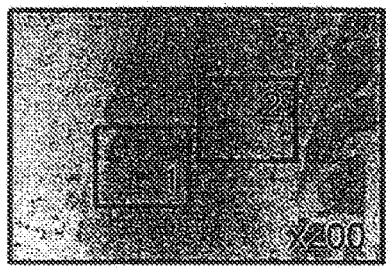
Figure 12E:
Figure 12F:
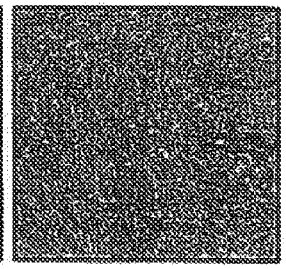

FIG. 11 demonstrate the effect of 1 μg/ml HO/02/10, while FIGS. 17-27, 35 and 40 demonstrate the ability of HO/02/10 to decrease dramatically the secretion of major pro-inflammatory cytokines from activated keratinocytes, such as TNFα, IL-1 and IL-6. Specifically, IL-6 was shown to be essential for the development of TH17 cells that are involved in the pathogenesis of psoriasis, with enhancing effect demonstrated for IL-1 and TNFα. TNFα and IL-6 are known targets for psoriasis therapy. FIG. 11 demonstrates the effect of 1 μg/ml HO/02/10.

HO/02/10 was also shown to inhibit basal keratinocyte and endothelial cell immunological activation in vivo. ICAM is an adhesion molecule that allows leukocytes infiltration into inflammatory lesions. Specifically in skin, basal keratinocytes express ICAM-1 upon immunological activation which may enhance infiltration of neutrophils and CD8-T cells into the epidermis, one of the hallmarks of psoriasis. Thus, the effect of HO/02/10 on ICAM expression in skin was examined by immunohistochemistry in a wound inflammatory setting in vivo.

Down regulation of activated keratinocytes and endothelial cells (ICAM-1 staining) in skin inflammation was observed. A two-cm longitudinal incision was done on the upper back of a C57BL/6J mouse. Following wounding, a sterile pad was sutured to the mouse's skin. Animals were treated daily with HO/02/10 (n=12). Five days post-wounding, when inflammatory phase reaches its peak, the mice were sacrificed, skin tissues were embedded in paraffin and immunohistochemical staining was performed utilizing anti-ICAM-1 antibodies.

As shown in FIG. 12, HO/02/10 dramatically reduces ICAM expression on basal keratinocytes and endothelial in blood vessels of the skin. This effect was shown to be dose dependent with maximal effect, demonstrated at 10 μg/ml.

Figure 13:
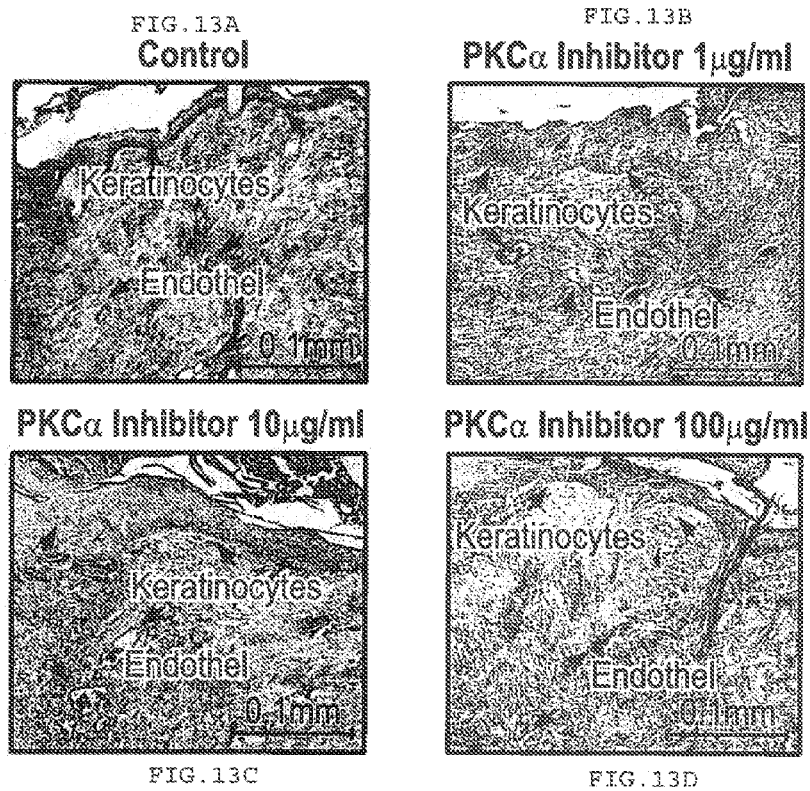
FIGS. 13A-13D are a series of pictorial representations showing ICAM expression in basal keratinocytes and endothelial cells in blood vessels of the skin following treatment with the inhibitory peptide MPDY-1 (SEQ ID NO:21).

FIG. 13 shows additional stains showing down regulation of activated keratinocytes and endothelial cells (ICAM-1 staining) in skin inflammation. As above, a two-cm longitudinal incision was done on the upper back of a C57BL/6J mouse. Following wounding, a sterile pad was sutured to the mouse's skin. Animals were treated daily with MPDY-1 (n=6). Five days post-wounding, when inflammatory phase reaches its peak, the mice were sacrificed, skin tissues were embedded in paraffin and immunohistochemical staining was performed utilizing anti-ICAM-1 antibodies.

Figure 14:
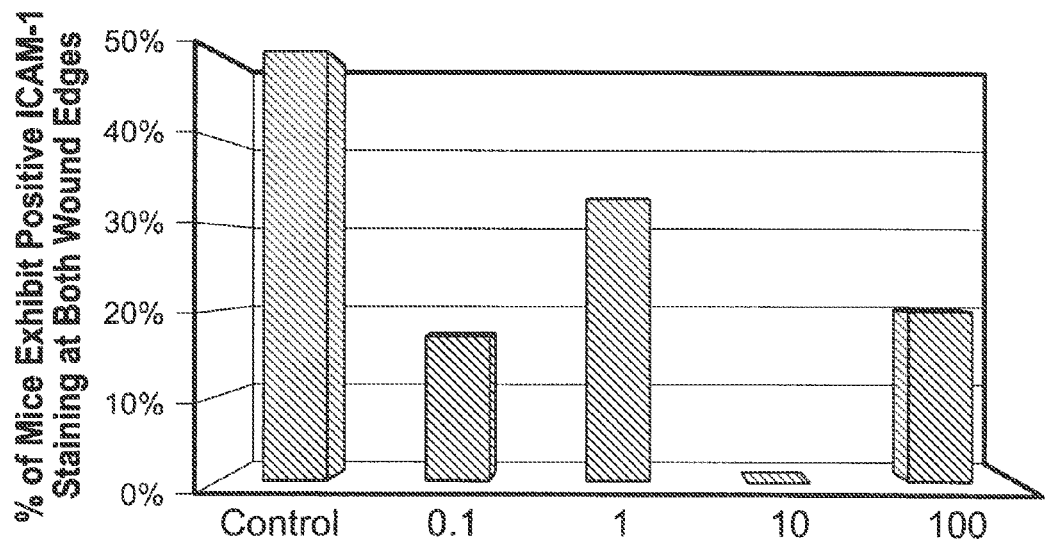
FIG. 14 is a histogram comparing the percent of mice exhibiting positive ICAM-1 staining at wound edges, following treatment with MPDY-1 (SEQ ID NO:21).

FIG. 14 is a histogram comparing the percent of mice exhibiting positive ICAM-1 staining at both wound edges.

Figure 15:
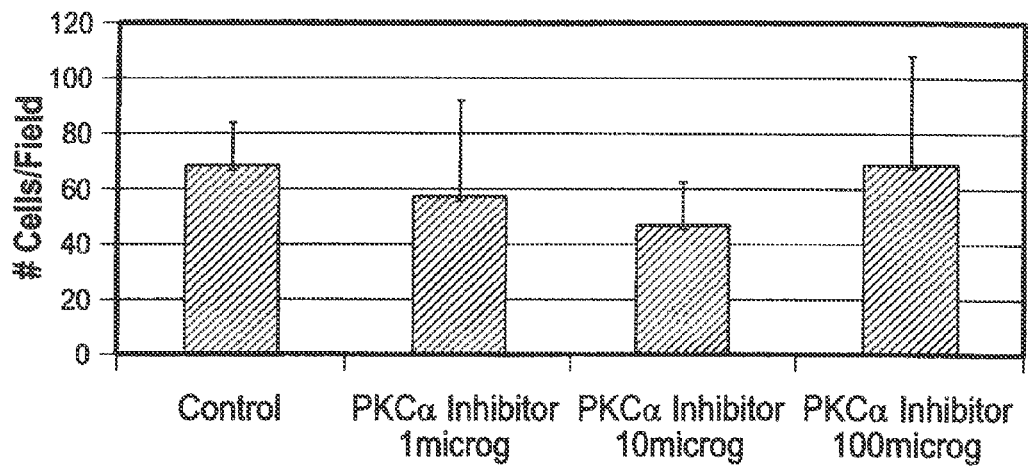
FIG. 15 is a histogram comparing the number of cells per field of Iba-1 positively stained cells, following treatment with MPDY-1 (SEQ ID NO:21).

The effect of MPDY-1 on macrophage infiltration was also shown by Iba-1 staining. Iba-1 is a general marker for macrophages. FIG. 15 is a histogram showing comparing the number of cells per field exhibiting positive Iba-1 staining. As above, a two-cm longitudinal incision was done on the upper back of a C57BL/6J mouse. Following wounding, a sterile pad was sutured to the mouse's skin. Animals were treated daily with MPDY-1 (n=6). Five days post-wounding, when inflammatory phase reaches its peak, the mice were sacrificed, skin tissues were embedded in paraffin and immunohistochemical staining was performed utilizing anti-Iba-1 antibodies. A dose dependent effect of MPDY-1 on macrophage infiltration was observed.

Figures 16A, 16B:
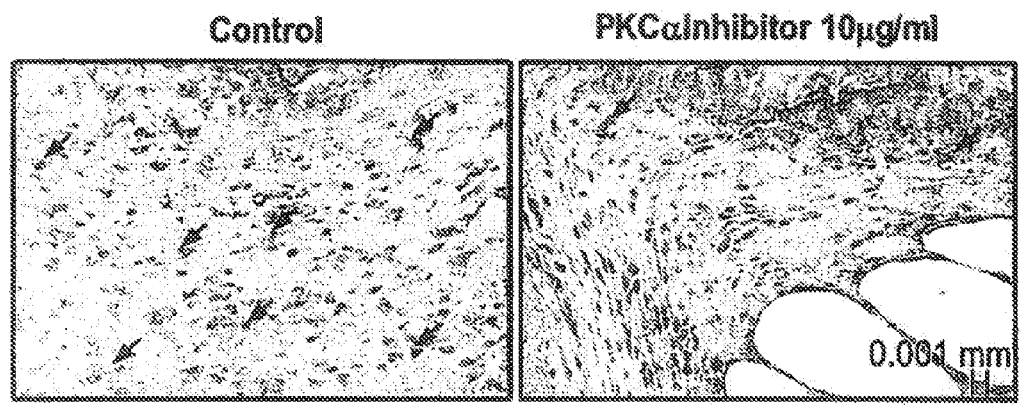
FIGS. 16A-16C are a series of pictorial and graphical representations showing MAC-2 expression in keratinocytes.
Figure 16C:
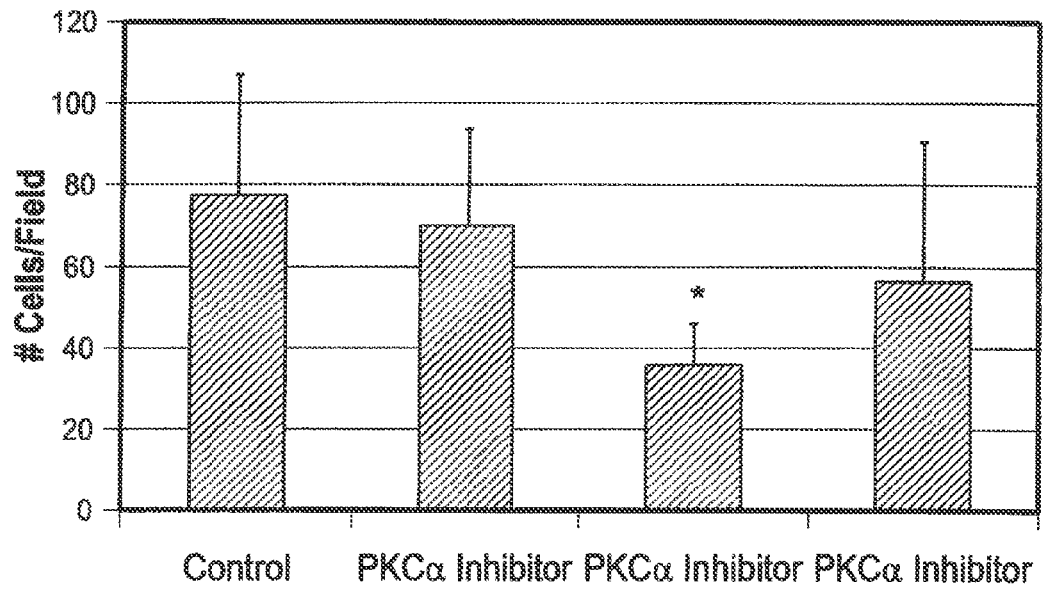
Figure 17A:
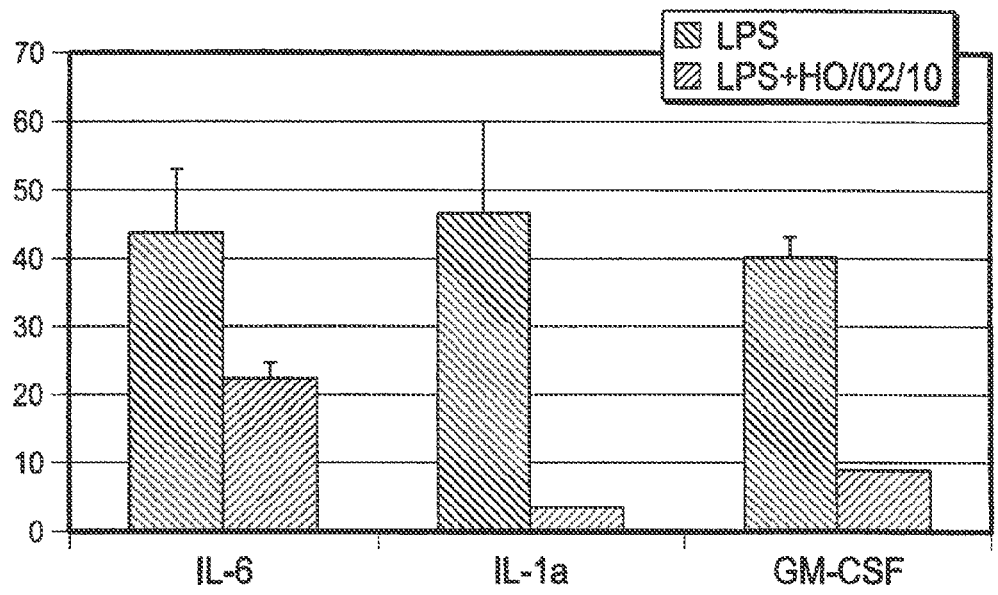
FIGS. 17A, 17B, 17C and 17D are a series of histograms comparing cytokine secretion in LPS activated keratinocytes treated with HO/02/10.
Figure 17B:
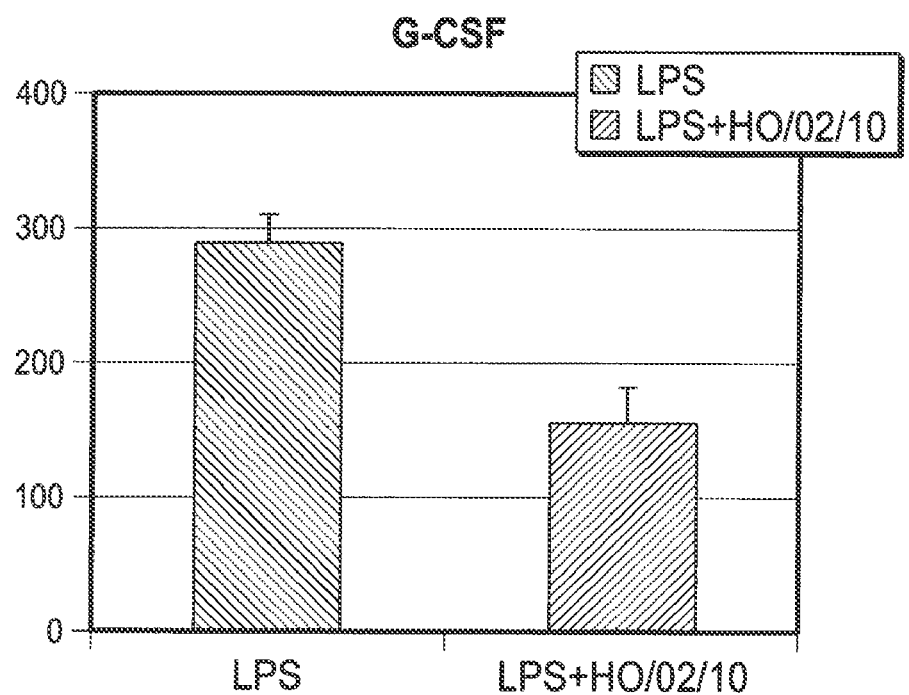
Figure 17C:
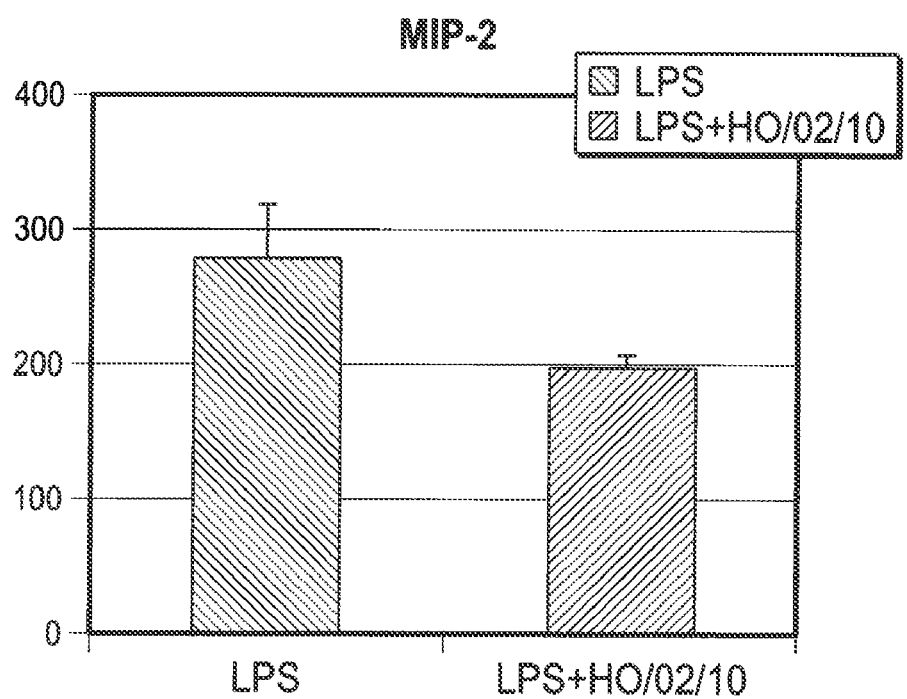
Figure 17D:
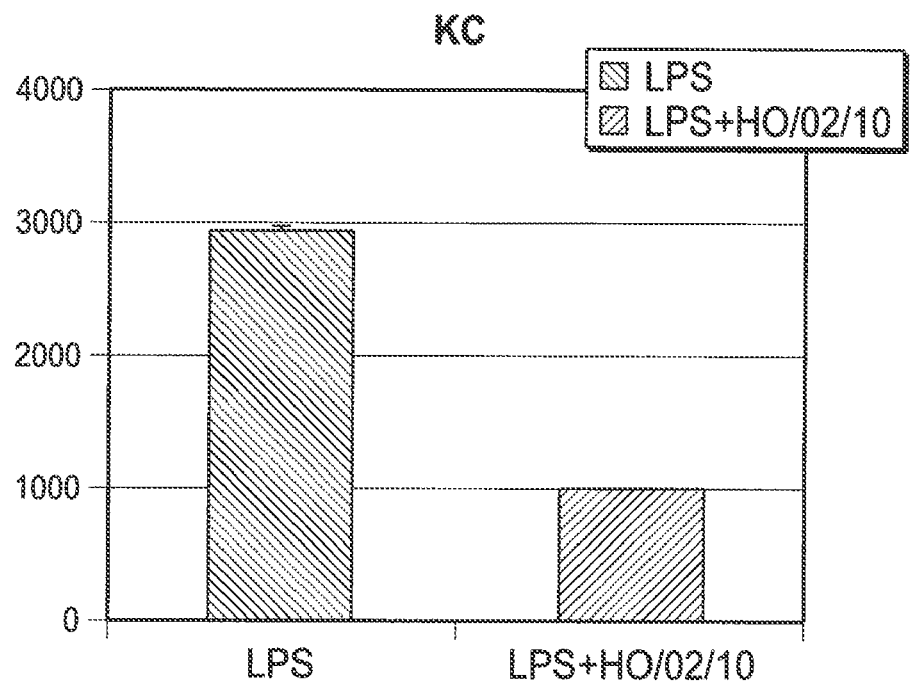

The effect of MPDY-1 on macrophage activation was also shown by MAC-2 staining. MAC-2 is a specific marker for activated macrophages. FIG. 16 shows a series of MAC-2 stains and a histogram comparing the number of cells per field exhibiting positive MAC-2 staining. A two-cm longitudinal incision was done as described above. Animals were treated daily with DPBS$^{-/-}$ (Control) or MPDY-1 in the specified concentrations (n=6). After 5 days immunohistochemical staining was performed utilizing anti-MAC-2 antibodies. Bar 1 μm. (*p(control Vs. MPDY-1 10 μg)=0.0028). Activation of macrophages was significantly inhibited following MPDY-1 treatment.

Figure 32:
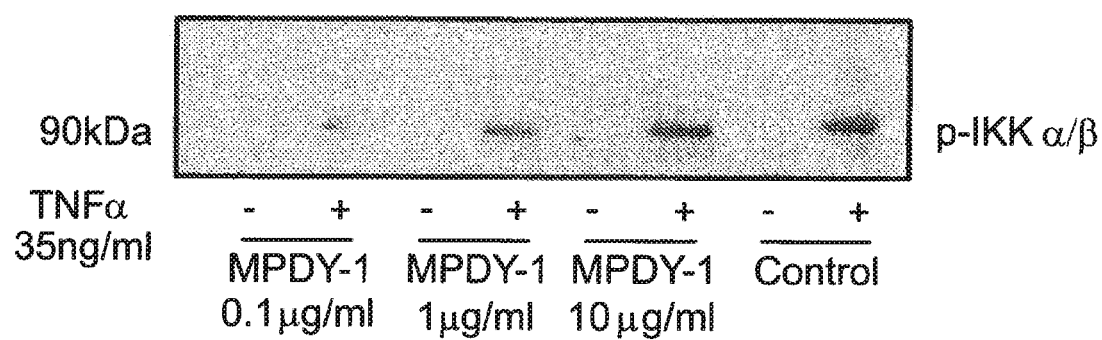
FIG. 32 is a pictorial representation of an SDS PAGE stained with Ser176/180 antibody.

MPDY-1 was also shown to significantly reduce TNFα induced IKK activation in keratinocytes in dose dependant manner as shown in FIG. 32. Murine primary keratinocytes were grown for 4 days to full confluence in Low $Ca^{+2}$ MEM. Cells were pretreated with designated concentration of MPDY-1 as described in the figure for 1 hour, prior to TNFα induction. Following MPDY-1 pretreatment, cells were incubated with TNFα 35 ng/ml for 15 minutes. Reaction was stopped by adding ice-cold dPBS−/− and keratinocytes were homogenized in RIPA buffer. Samples were subjected to SDS PAGE Western Blot analysis, utilizing phospho-IKKa/b (Ser176/180 antibody). Pretreatment with MPDY-1 significantly reduced TNFα induced IKK activation in keratinocytes in dose dependant manner, where lowest MPDY-1 concentration (0.1 mg/ml) exhibited the strongest inhibition thus suppressing NFkB activation.

As discussed above, HO/02/10 was also shown to decrease cytokine secretion from activated keratinocytes and macrophages. In recent years it was found that both immune and skin components are equally contributing to the cycle underlying psoriatic pathogenesis. Resident skin cells and immunological cells (both resident and infiltrating cells) interact in the inflammatory psoriatic process by cell-cell interactions and cytokine secretion. Thus, HO/02/10 was examined for its direct effect on the secretion of pro-inflammatory, chemoattractant and immunological pathway related cytokines form both keratinocytes and immune cells such as macrophages and dendritic cells. The results depicted in FIGS. 17 and 18 demonstrate that HO/02/10 down regulates secretion of immune related cytokines such as IL-6, IL-1α, GM-CSF, MIP-2 and KC from keratinocytes and macrophages.

The results of FIG. 17 show the effect of HO/02/10 on cytokine secretion in keratinocytes. Keratinocytes were derived from newborn C57BL/6J mice skin. The cells were incubated for 5 days in 24 wells plates. Cells were then treated with DPBS−/−, LPS (100 ng/ml), or HO/02/10 (1 μg/ml)+ LPS (100 ng/ml). Medium containing secreted cytokines was collected after 48 hr and analyzed using a LUMINEX system.

Figure 18A:
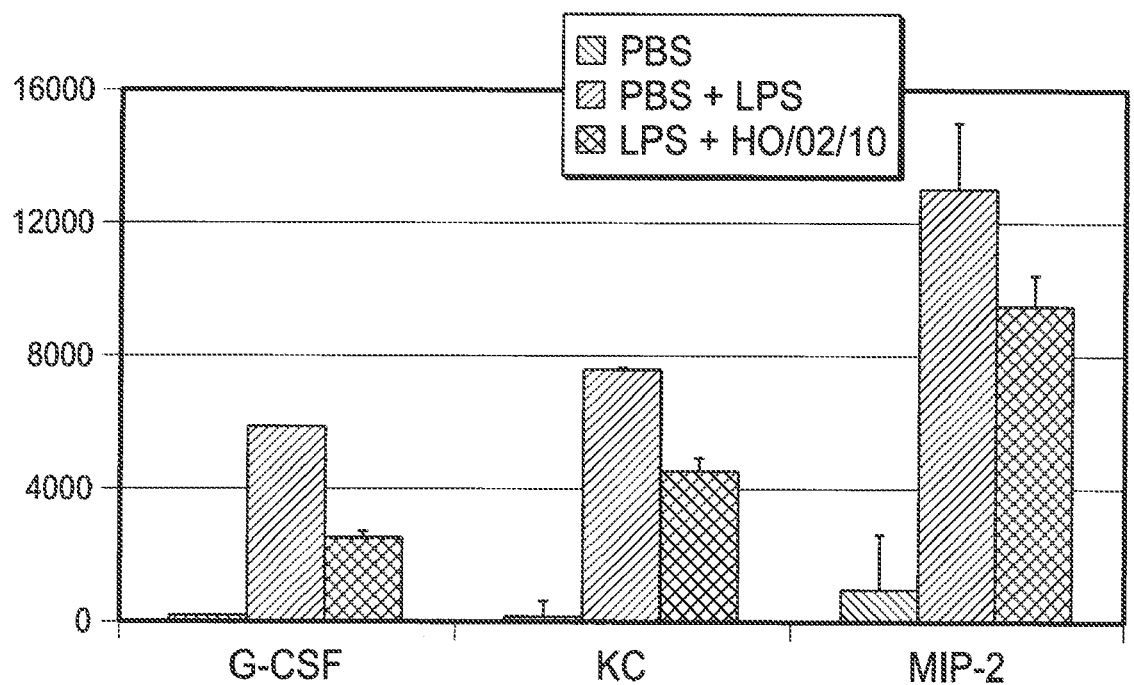
FIGS. 18A, 18B and 18C are a series of histograms comparing cytokine secretion in LPS activated macrophages treated with HO/02/10.
Figure 18B:
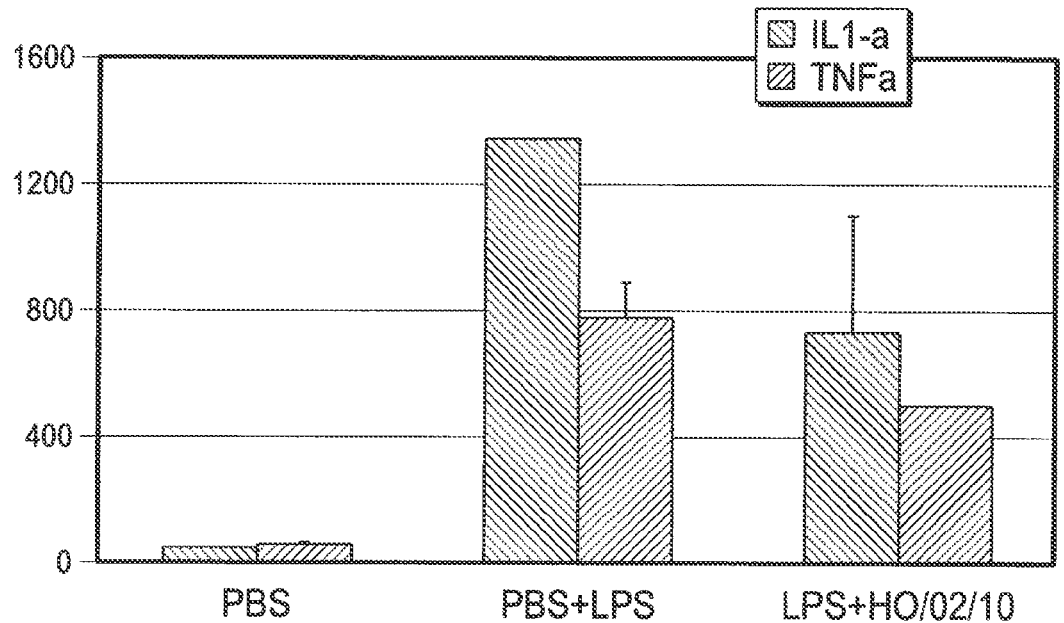
Figure 18C:
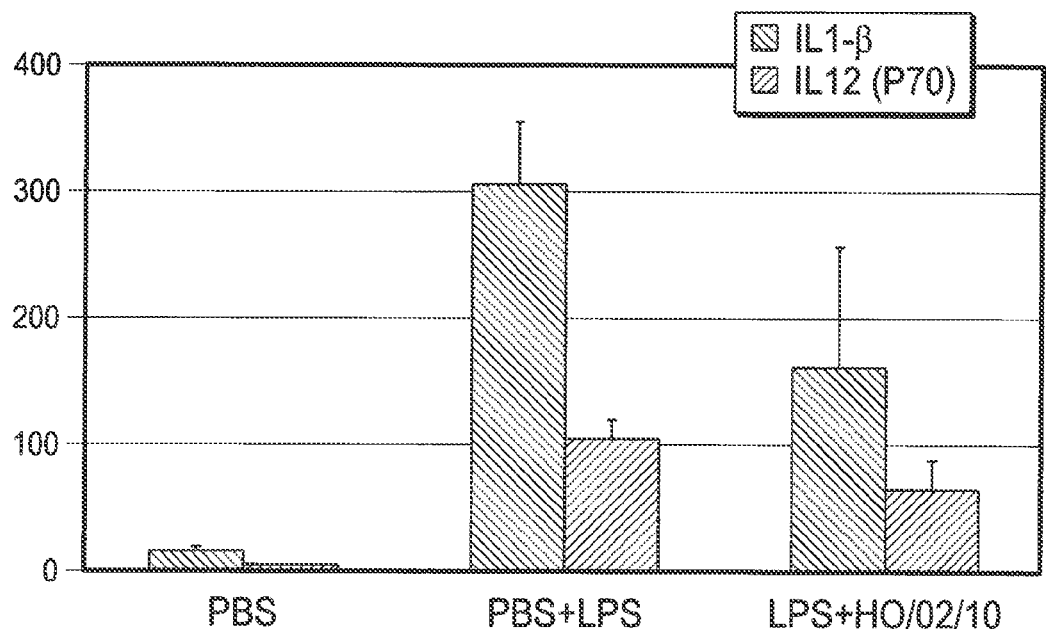
Figure 19:
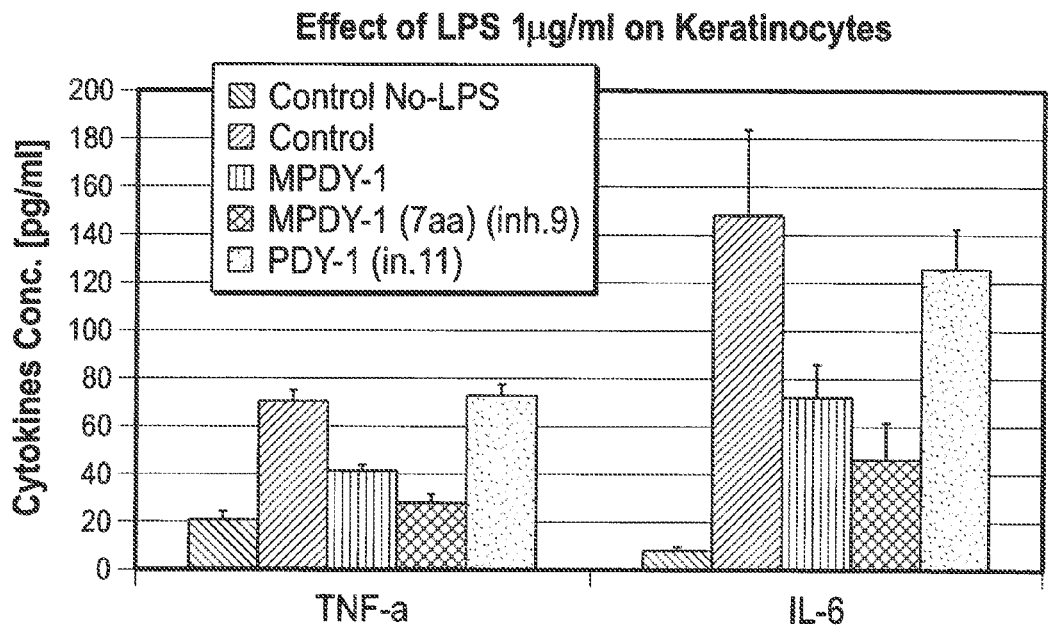
FIG. 19 is a histogram comparing cytokine secretion in LPS activated keratinocytes treated with several peptide PKCα inhibitors, MPDY-1 (SEQ ID NO:21), PDY-1 (AWOT, SEQ ID NO: 5), and AIP-2 (SEQ ID NO: 20).
Figure 20:
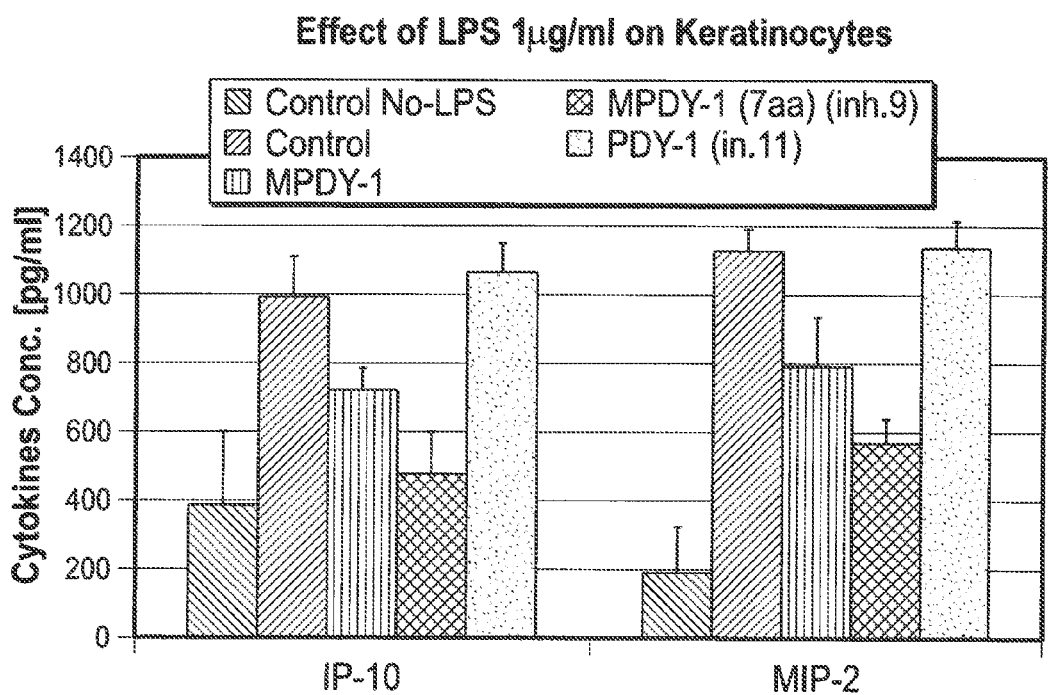
FIG. 20 is a histogram comparing cytokine secretion in LPS activated keratinocytes treated with peptide PKCα inhibitors.
Figure 21A:
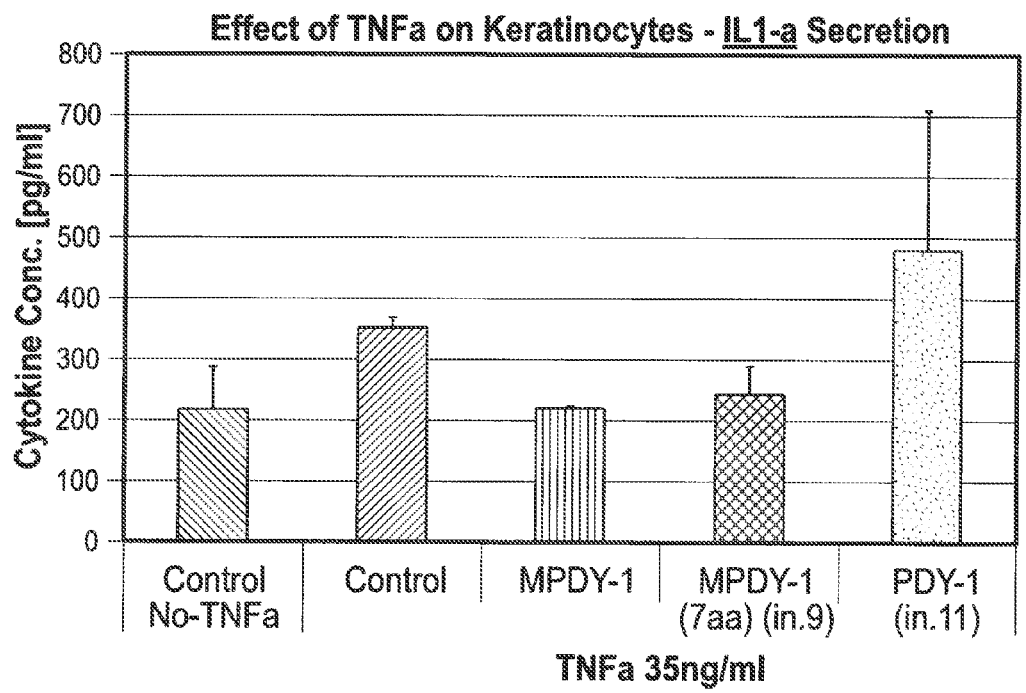
FIGS. 21A and 21B are histograms comparing cytokine secretion in TNFα activated keratinocytes treated with peptide PKCα inhibitors.
Figure 21B:
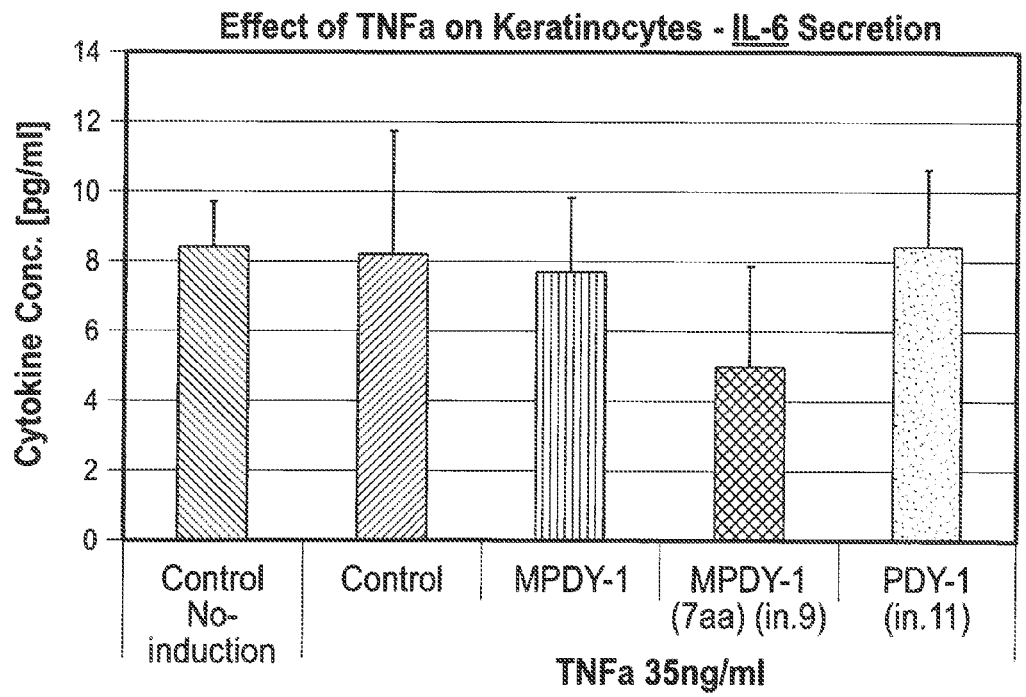
Figure 22A:
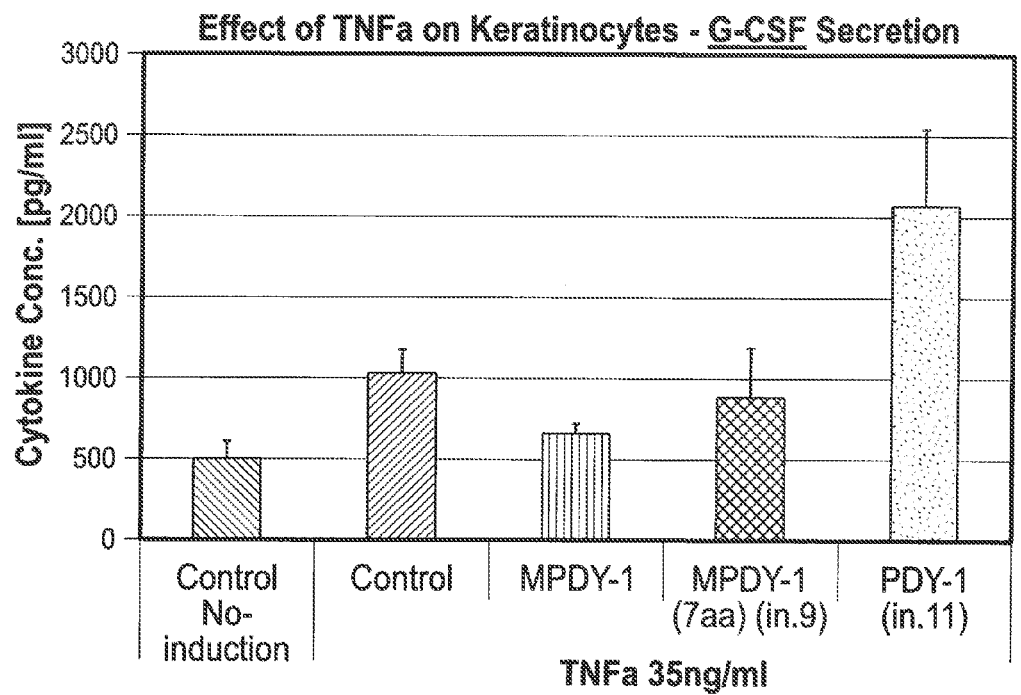
FIGS. 22A and 22B are histograms comparing cytokine secretion in TNFα activated keratinocytes treated with peptide PKCα inhibitors.
Figure 22B:
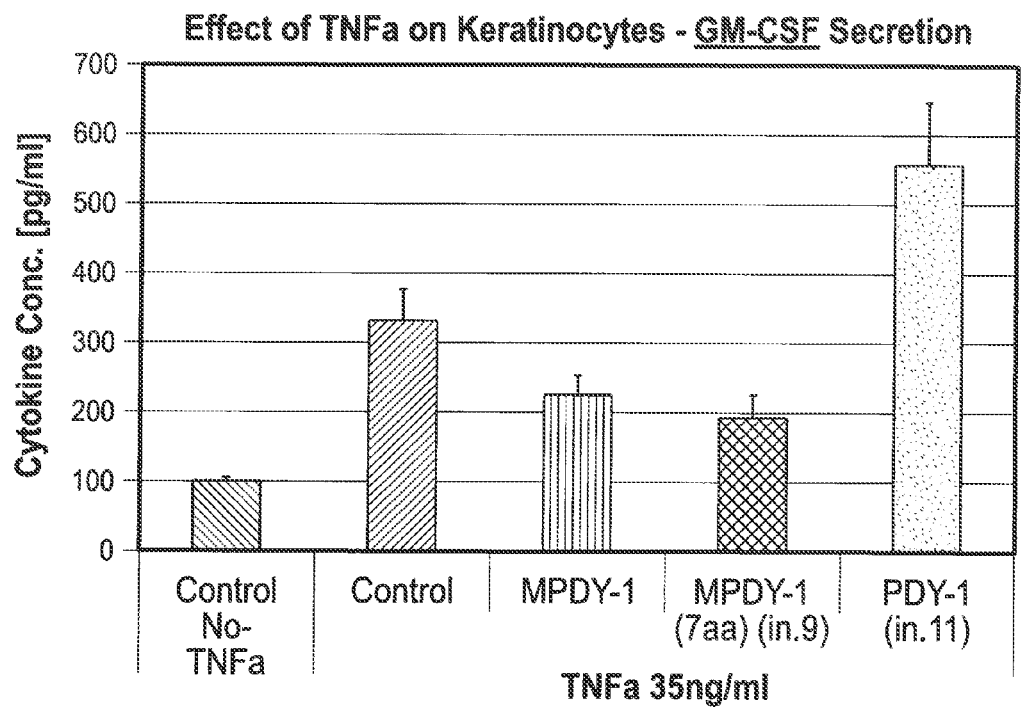
Figure 23A:
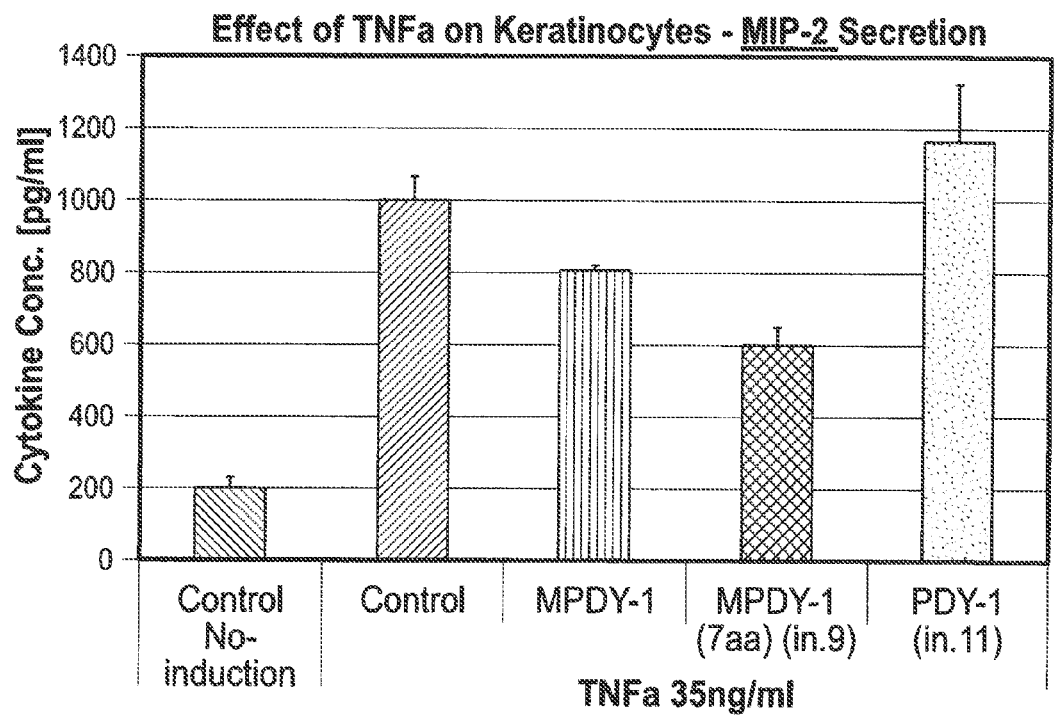
FIGS. 23A and 23B are histograms comparing cytokine secretion in TNFα activated keratinocytes treated with peptide PKCα inhibitors.
Figure 23B:
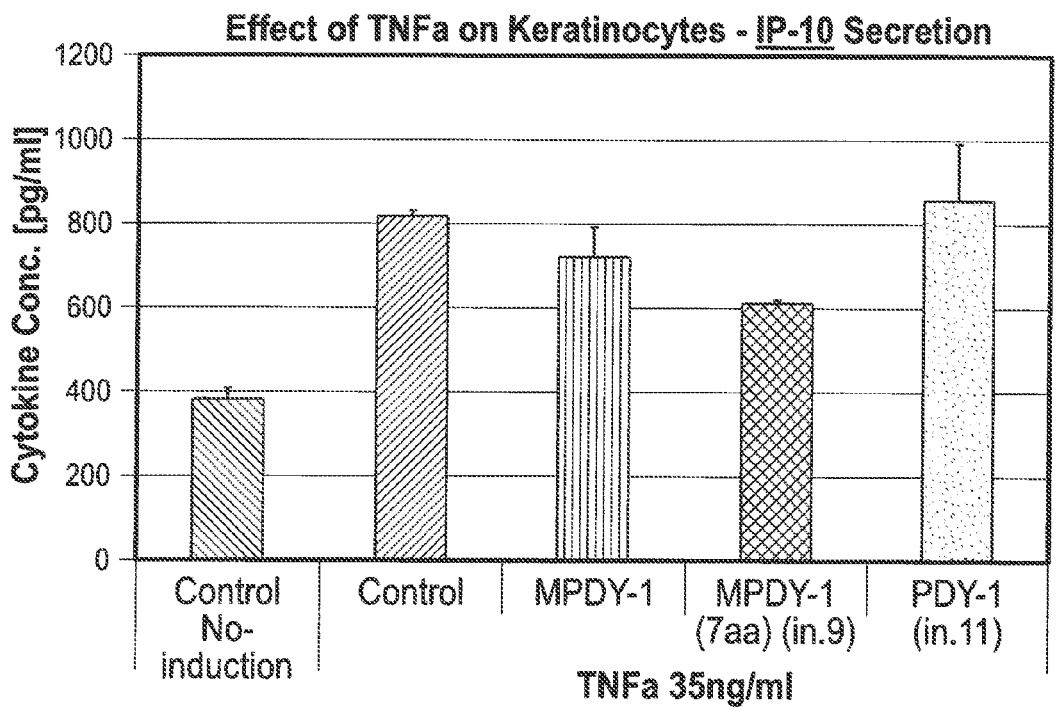

The results of FIG. 18 show that HO/02/10 down regulates cytokine secretion in macrophages. Bone marrow cells were derived from B6 mice. Cells were incubated for 6 days in the presence of GM-CSF (20 ng/ml), and then were treated with DPBS−/−, LPS (100 ng/ml) or HO/02/10+LPS (1 mg/ml and 100 ng/ml, respectively).

Other peptide PKCα inhibitors were also shown to decrease cytokine secretion from activated keratinocytes and macrophages. FIGS. 19 to 23 show that the peptide inhibitors MPDY-1 (SEQ ID NO: 21), AIP-2 (SEQ ID NO: 20) and PDY-1 (SEQ ID NO: 5) decrease cytokine secretion from LPS and TNFα activated keratinocytes. FIGS. 24 to 27 show that the peptide inhibitors MPDY-1 (SEQ ID NO: 21), AIP-2 (SEQ ID NO: 20) and PDY-1 (SEQ ID NO: 5) decrease cytokine secretion from IL-17A activated keratinocytes.

Table 7 summarizes the results of HO/02/10 treatment on cytokine secretion.

The PKCα inhibitors MPDY-1 (SEQ ID NO: 6), AIP-2 (SEQ ID NO: 8), AIP-1 (SEQ ID NO: 9), AWOT (SEQ ID NO: 7) and PPDY-1 (SEQ ID NO: 10) were all shown to be effective in decreasing cytokine secretion in keratinocytes.

HO/02/10 was also shown to attenuate T cell infiltration to the skin. The effect of HO/02/10 on T cell infiltration was studied in vivo using anti-CD3 specific staining.

Figure 28E:
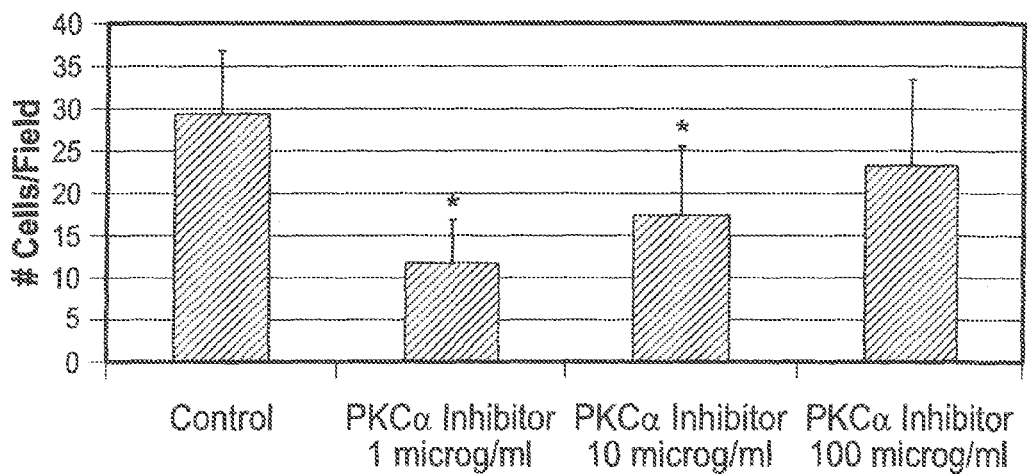
Figures 29A, 29B, 29C:
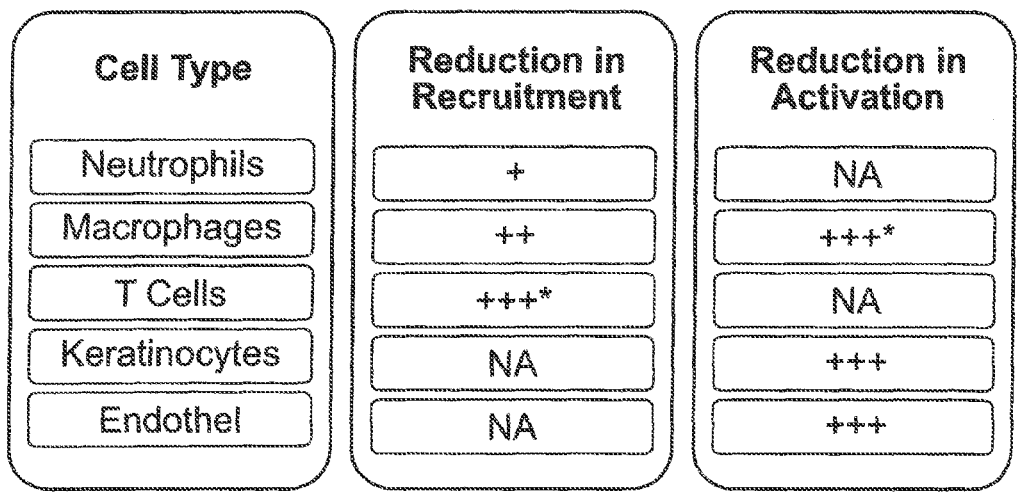
FIGS. 29A-29C are graphical representations summarizing the effects of treatment using the peptide PKCα inhibitor MPDY-1 (SEQ ID NO:21) on different cell types.

As can be seen in FIG. 28, HO/02/10 down regulated T cell infiltration to the dermis and epidermis during the inflammatory stage. Specifically HO/02/10 inhibited T cell infiltration into the epidermis which indicates additional anti-inflammatory properties also characteristic of psoriasis plaques. A two-cm longitudinal incision was done as described above. Animals were treated daily with 1-10/02/10 (n=12). After nine days immunohistochemical staining was performed utilizing anti-CD3 antibodies. FIG. 28B is a histogram comparing the number of cells per field positively stained for CD3. The effect was statistically significant at concentrations of 1 μg/ml and 10 μg/ml, where 1 μg/ml treatment demonstrates stronger effects than 10 μg/ml.

Figure 31A:
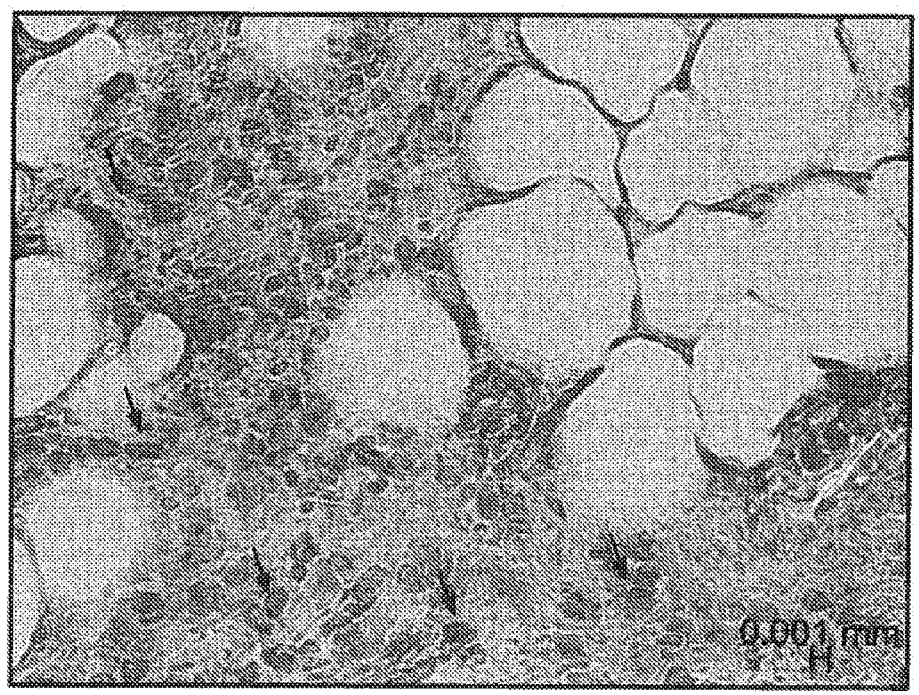
FIGS. 31A-B are a series of pictorial and graphical representations showing down regulation of neutrophil infiltration to the dermis and epidermis during the inflammatory stage after treatment with HO/02/10.
Figure 31B:
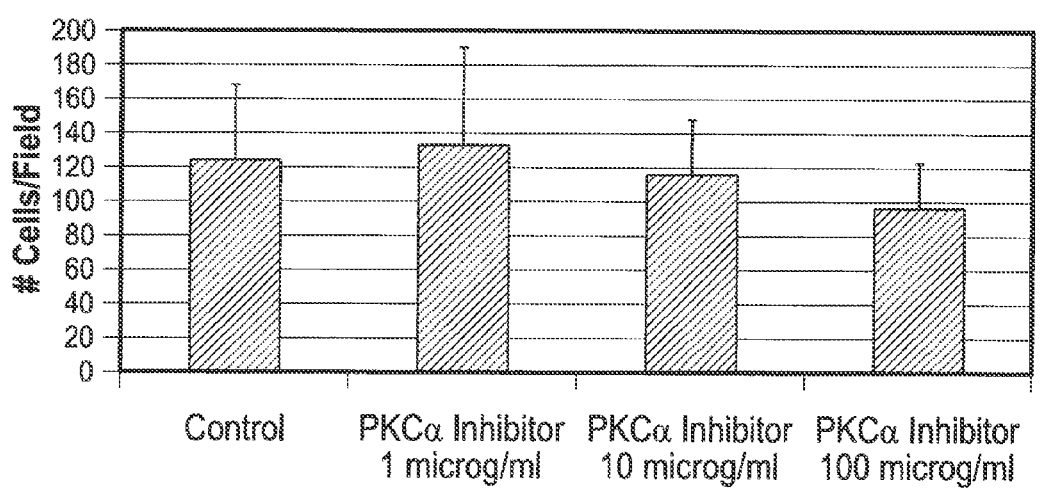

HO/02/10 was also shown to attenuate neutrophil infiltration to the skin (FIG. 31). The effect of HO/02/10 on neutrophil infiltration was studied in vivo using neutrophil specific staining. A two-cm longitudinal incision was done as described above. Animals were treated daily with DPBS−/− (Control) or PKCα inhibitor in the specified concentrations (n=6). After five days the mice were sacrificed, skin tissues were embedded in paraffin and immunohistochemical staining for neutrophils was performed. Although a dose dependent trend was observed, results were not statistically significant.

PKCδ activators were also shown to have an anti-inflammatory effect on keratinocytes and splenocytes. Keratinocytes were derived from newborn BALB/C mice skin. The cells were incubated for 5 days in 24 wells plate. Cells were then incubated with PBS−/− as control or stimulated by LPS or TNFα. The PKCδ inhibitor DAP-1 (SEQ ID NO: 16) was added. Medium containing secreted cytokines was collected

TABLE 7

HO/02/10 Effect on Stimulated Mice Derived-Cells

| | Pro-inflammatory (% inhibition) | Chemo-attractants (% inhibition) | Systemic (% inhibition) | Th1 (% inhibition) | Th17 (% inhibition) |
|---|---|---|---|---|---|
| Keratinocytes | IL-1 (80%) IL-6 (40%) | KC (65%) MIP-2 (30%) | GM-CSF (50%) G-CSF (30%) | | IL-6 (40%) |
| Spleen | IL-1 (50%) IL-6 (40%) TNFa (50%) | | | | |
| Bone marrow macrophages | IL-1 50% TNFa (50%) | KC (40%) MIP-2 (30%) | G-CSF (40%) | IL-12 (40%) TNFα (50%) IP-10 (20%) | |
| Bone marrow DCs | IL-6 (30%) | | | | |

Figure 40:
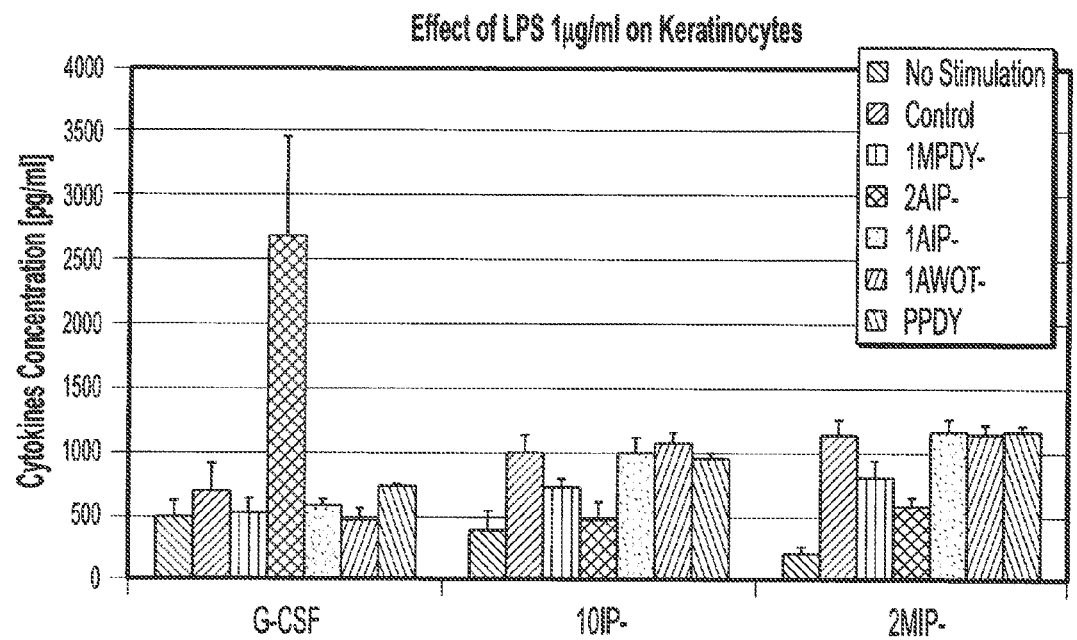
FIG. 40 is a histogram comparing cytokine secretion in LPS activated keratinocytes treated with peptide PKCα inhibitors including MPDY-1 (SEQ ID NO: 21), AWOT-1 (SEQ ID NO. 5), AIP-2 (SEQ ID NO: 20), AIP-1 (SEQ ID NO: 3), and PPDY (SEQ ID NO: 22).
Figure 41:
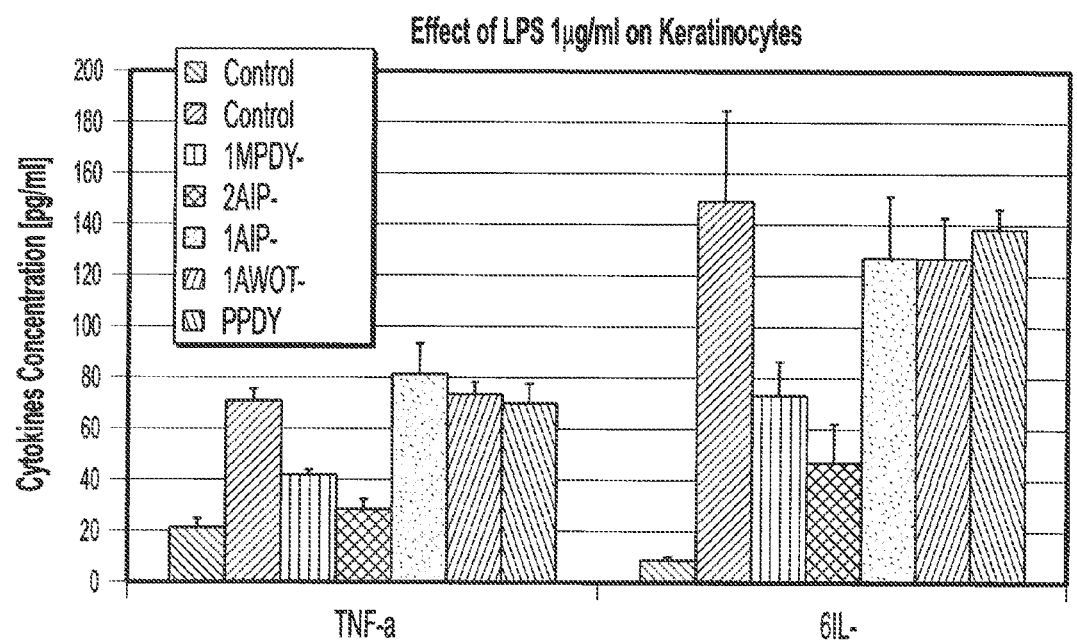
FIG. 41 is a histogram comparing cytokine secretion in LPS activated keratinocytes treated with peptide PKCα inhibitors including MPDY-1 (SEQ ID NO: 21), AWOT-1 (SEQ ID NO. 5), AIP-2 (SEQ ID NO: 20), AIP-1 (SEQ ID NO: 3), and PPDY (SEQ ID NO: 22).
Figure 42:
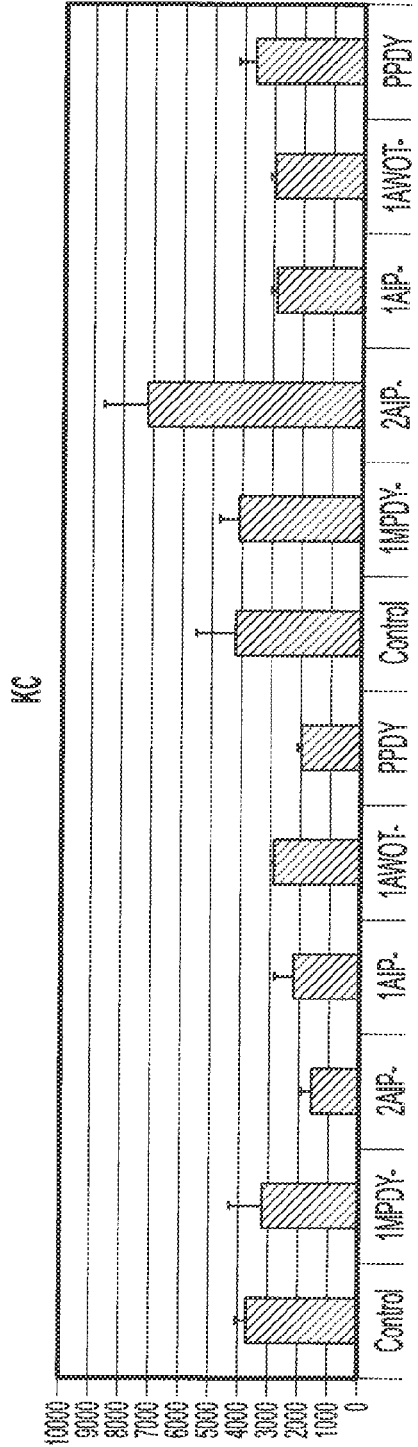
FIG. 42 is a histogram comparing cytokine secretion in LPS activated keratinocytes treated with peptide PKCα inhibitors including MPDY-1 (SEQ ID NO: 21), AWOT-1 (SEQ ID NO. 5), ATP-2 (SEQ ID NO: 20), AIP-1 (SEQ ID NO: 3), and PPDY (SEQ ID NO: 22).
Figure 43:
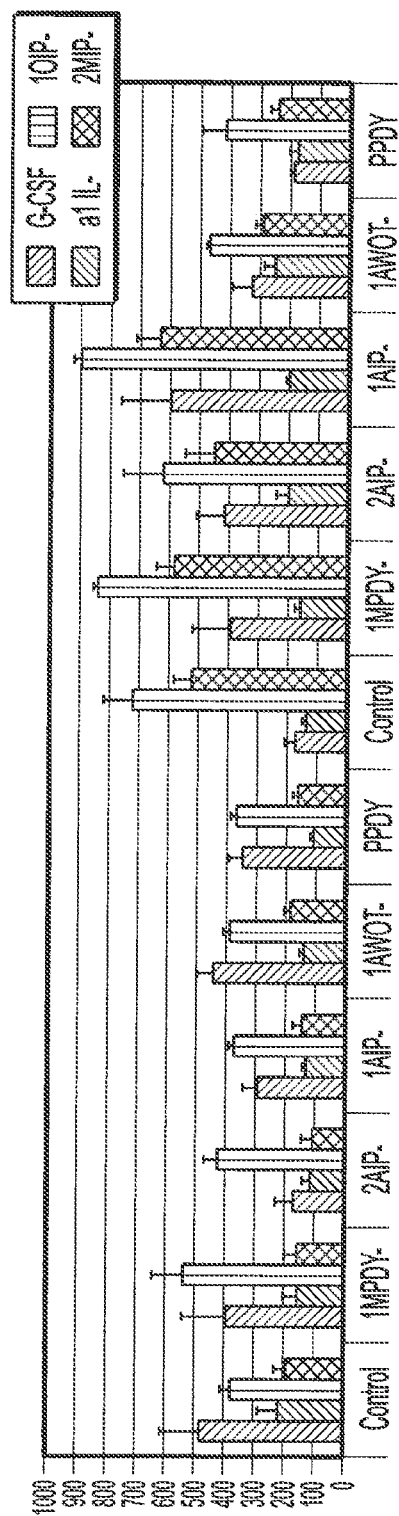
FIG. 43 is a histogram comparing cytokine secretion in LPS activated keratinocytes treated with peptide PKCα inhibitors including MPDY-1-(SEQ ID NO: 21), AWOT-1 (SEQ ID NO. 5), AIP-2 (SEQ ID NO: 20), AIP-1 (SEQ ID NO: 3), and PPDY (SEQ ID NO: 22).
Figure 44:
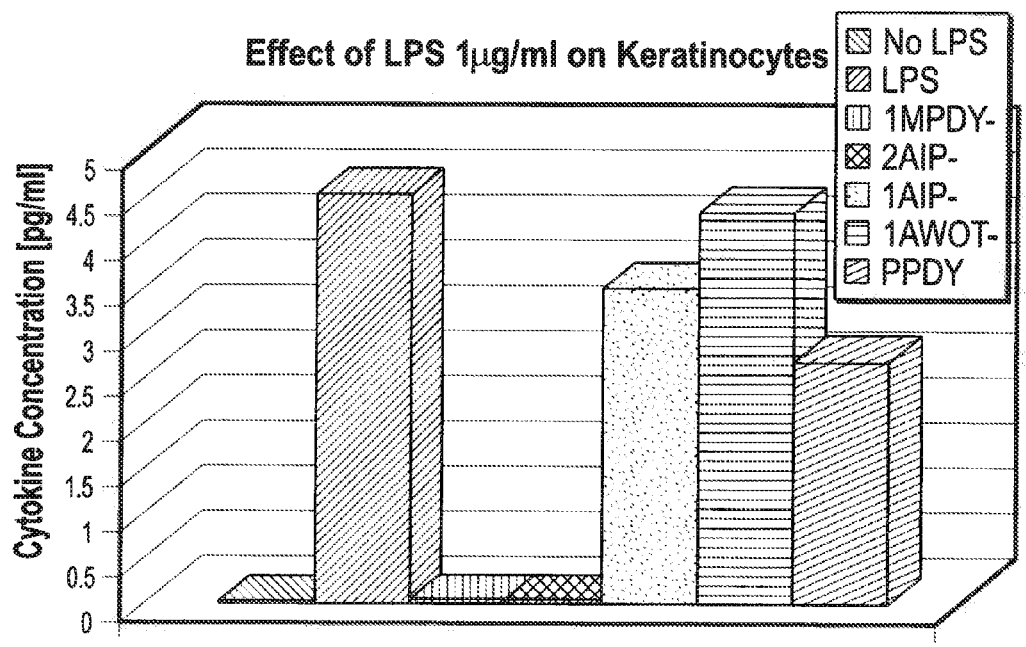
FIG. 44 is a histogram comparing cytokine secretion in LPS activated keratinocytes treated with peptide PKCα inhibitors including MPDY-1 (SEQ ID NO: 21), AWOT-1 (SEQ ID NO. 5), AIP-2 (SEQ ID NO: 20), AIP-1 (SEQ ID NO: 3), and PPDY (SEQ ID NO: 22).
Figure 45:
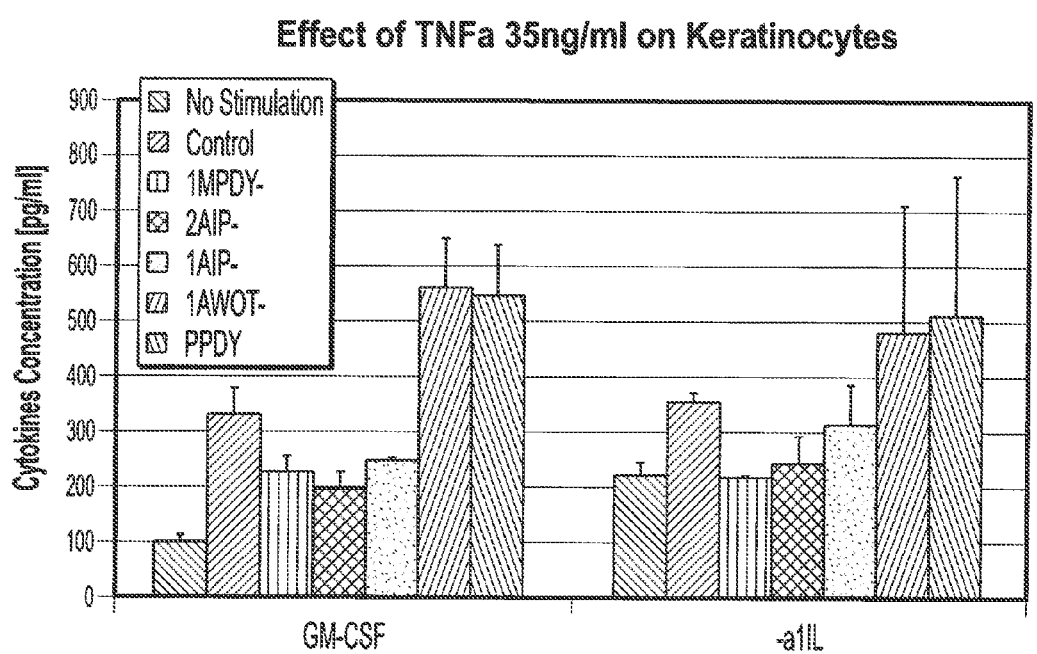
FIG. 45 is a histogram comparing cytokine secretion in TNFα activated keratinocytes treated with peptide PKCα inhibitors including MPDY-1 (SEQ ID NO: 21), AWOT-1 (SEQ ID NO. 5), AIP-2 (SEQ ID NO: 20), AIP-1 (SEQ ID NO: 3), and PPDY (SEQ ID NO: 22).
Figure 46:
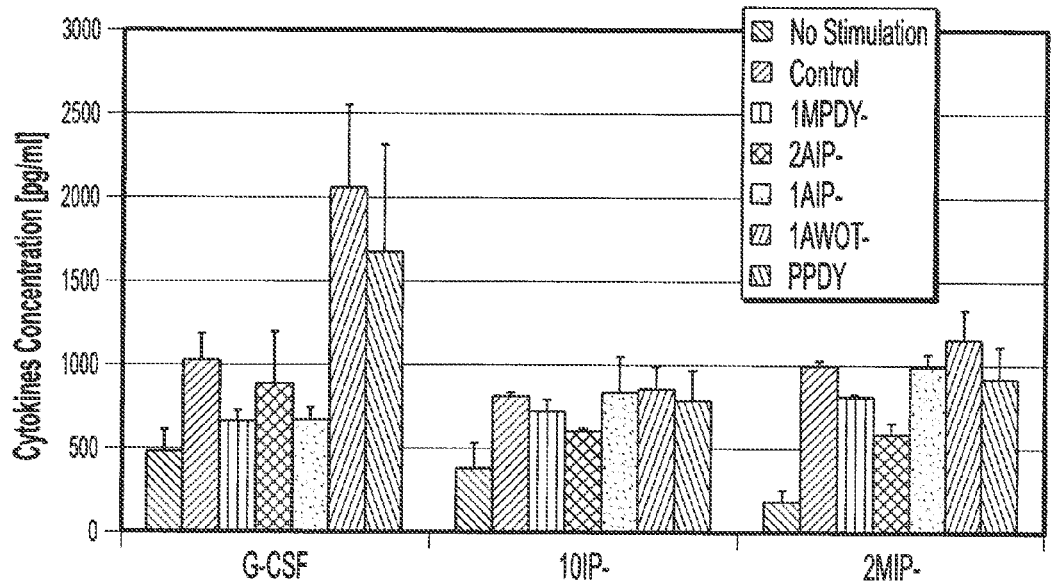
FIG. 46 is a histogram comparing cytokine secretion in TNFα activated keratinocytes treated with peptide PKCα inhibitors including MPDY-1 (SEQ ID NO: 21), AWOT-1 (SEQ ID NO. 5), AIP-2 (SEQ ID NO: 20), AIP-1 (SEQ ID NO: 3), and PPDY (SEQ ID NO: 22).
Figure 47:
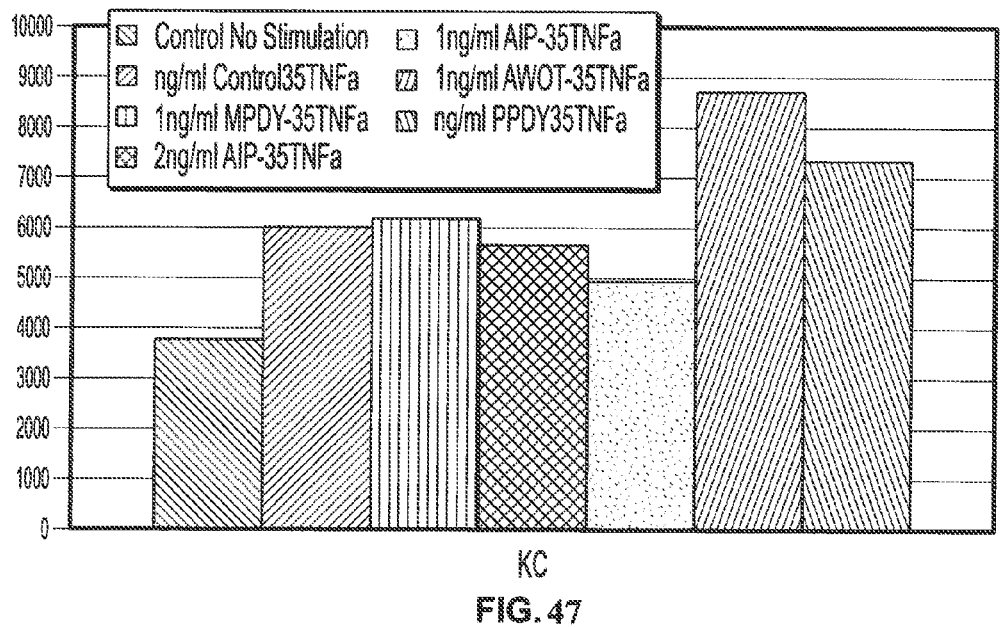
FIG. 47 is a histogram comparing cytokine secretion in TNFα activated keratinocytes treated with peptide PKCα inhibitors including MPDY-1 (SEQ ID NO: 21), AWOT-1 (SEQ ID NO. 5), AIP-2 (SEQ ID NO: 20), AIP-1 (SEQ ID NO: 3), and PPDY (SEQ ID NO: 22).
Figure 48:
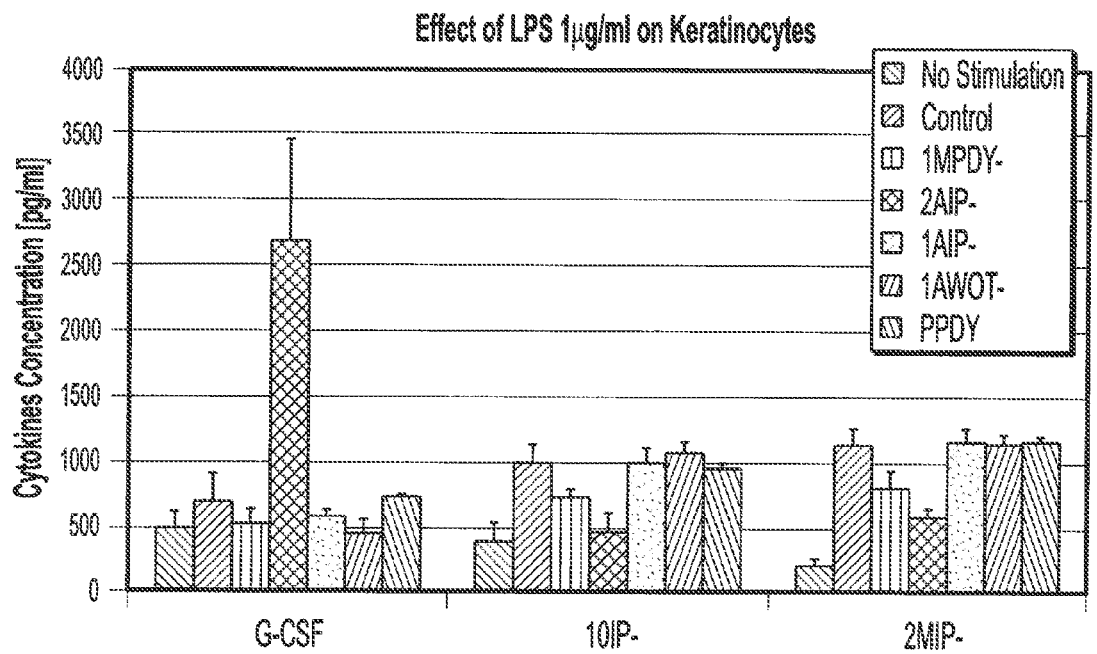
FIG. 48 is a histogram comparing cytokine secretion in LPS activated keratinocytes treated with peptide PKCα inhibitors including MPDY-1 (SEQ ID NO: 21), AWOT-1 (SEQ ID NO. 5), AIP-2 (SEQ ID NO: 20), AIP-1 (SEQ ID NO: 3), and PPDY (SEQ ID NO: 22).
Figure 49:
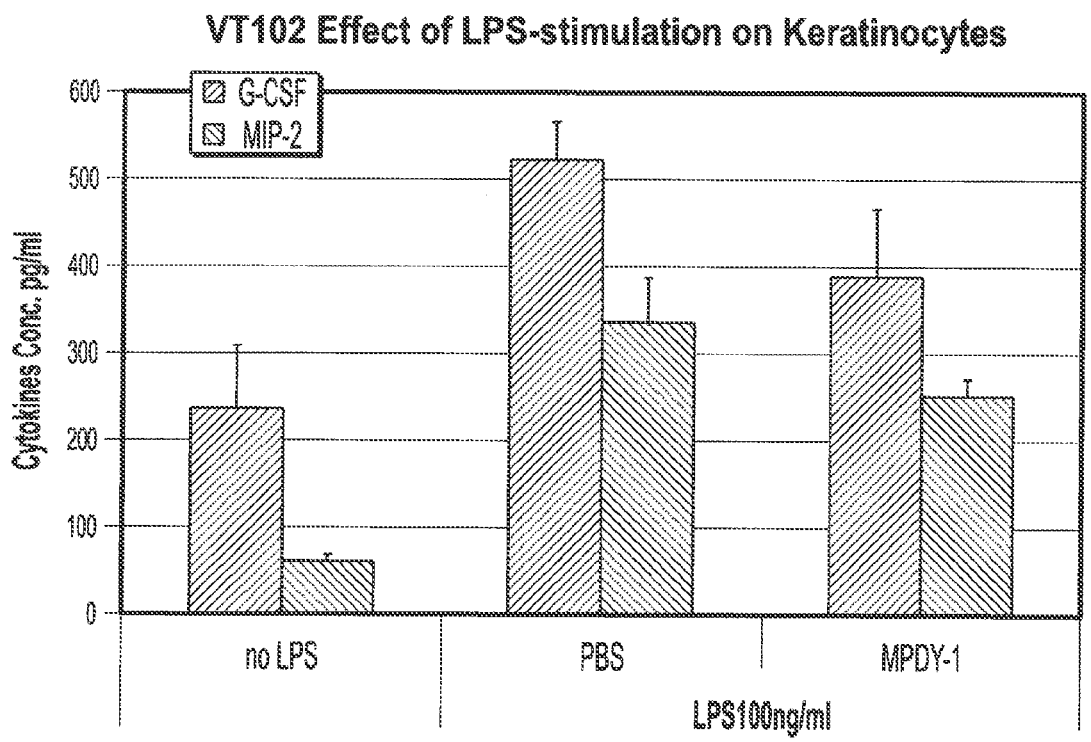
FIG. 49 is a histogram comparing cytokine secretion in LPS activated keratinocytes treated with peptide PKCα inhibitor MPDY-1 (SEQ ID NO: 21).
Figure 50:
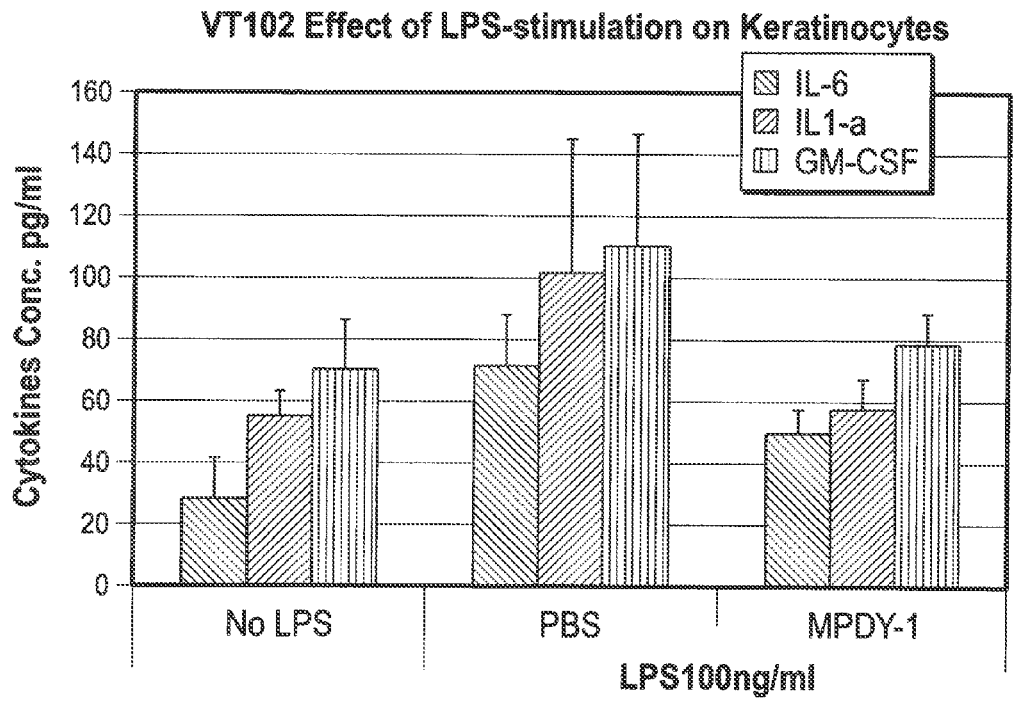
FIG. 50 is a histogram comparing cytokine secretion in LPS activated keratinocytes treated with peptide PKCα inhibitor MPDY-1 (SEQ ID NO: 21).
Figure 51:
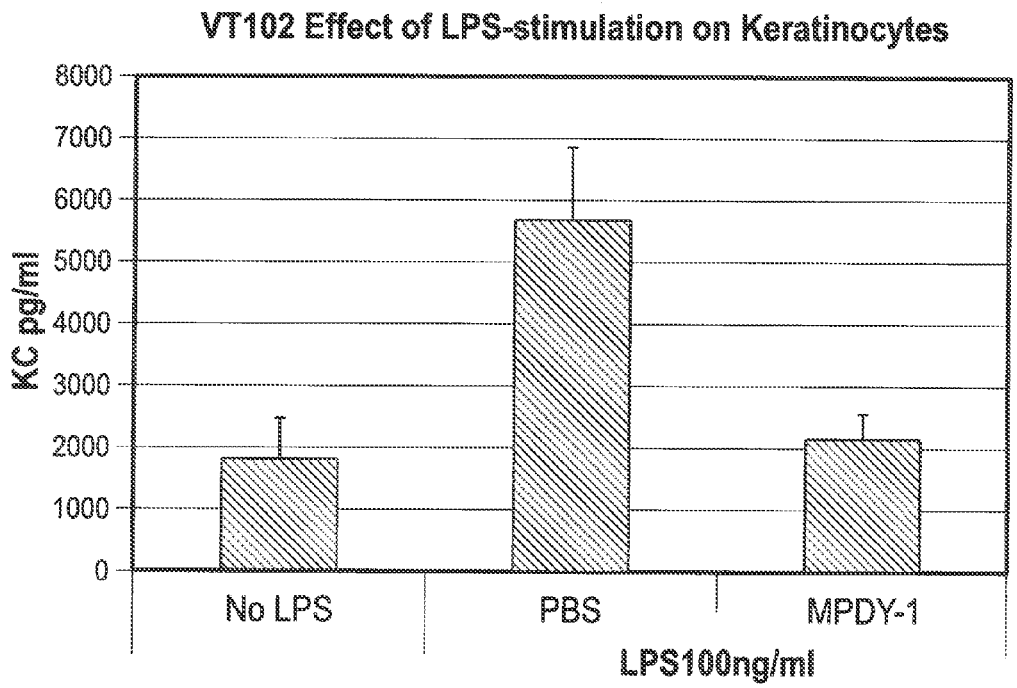
FIG. 51 is a histogram comparing cytokine secretion in LPS activated keratinocytes treated with peptide PKCα inhibitor MPDY-1 (SEQ ID NO: 21).
Figure 52:
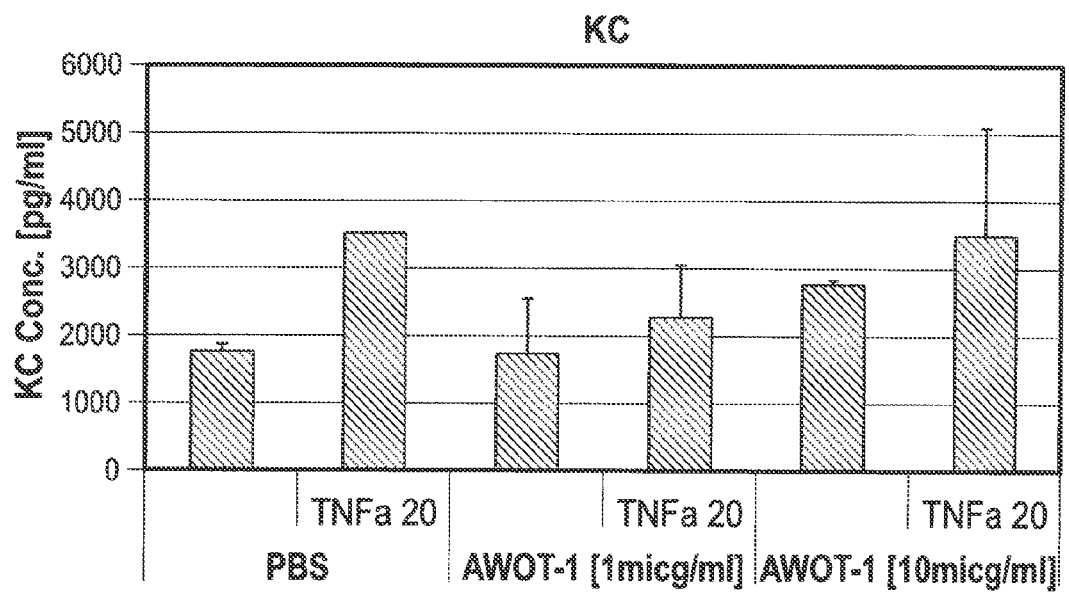
FIG. 52 is a histogram comparing cytokine secretion in LPS activated keratinocytes treated with peptide PKCα inhibitor AWOT-1 (SEQ ID NO: 7).
Figure 53:
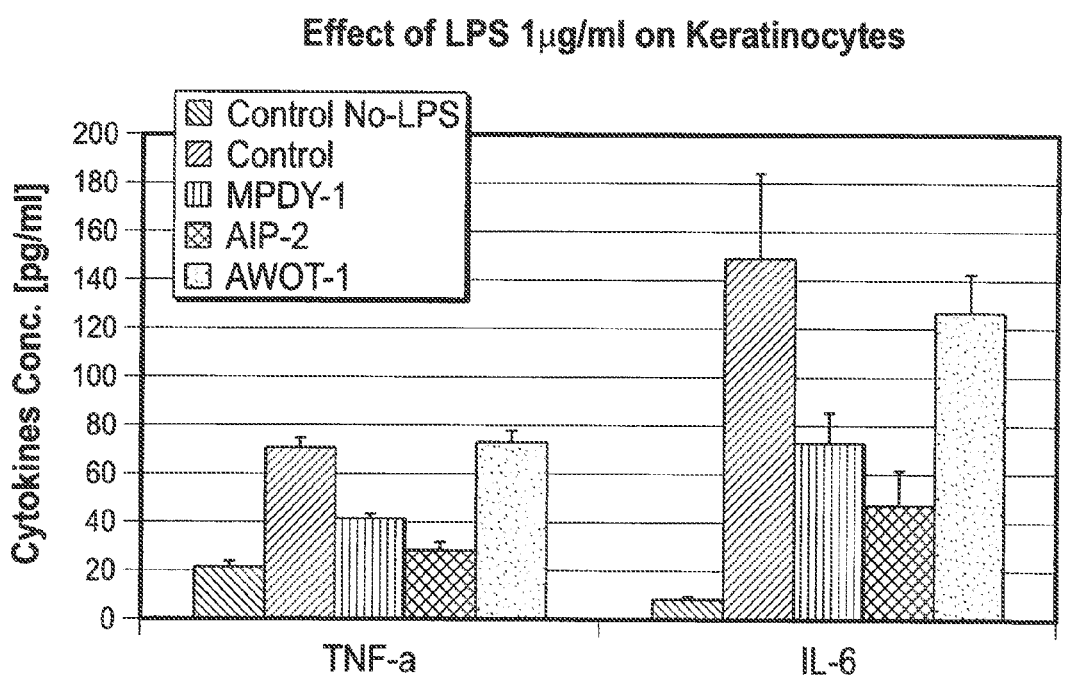
FIG. 53 is a histogram comparing cytokine secretion in LPS activated keratinocytes treated with peptide PKCα inhibitors MPDY-1 (SEQ ID NO: 21), AWOT-1 (SEQ ID NO: 5), and AIP-2 (SEQ ID NO: 20).
Figure 54:
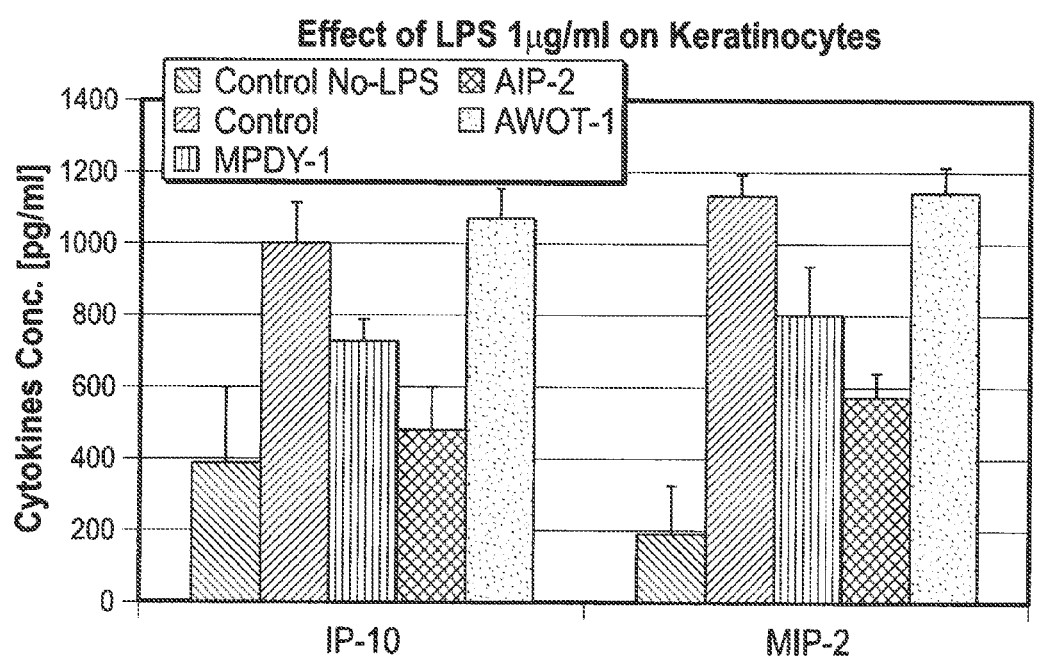
FIG. 54 is a histogram comparing cytokine secretion in LPS activated keratinocytes treated with peptide PKCα inhibitors MPDY-1 (SEQ ID NO: 21), AWOT-1 (SEQ ID NO: 5), and AIP-2 (SEQ ID NO: 20).
Figure 55:
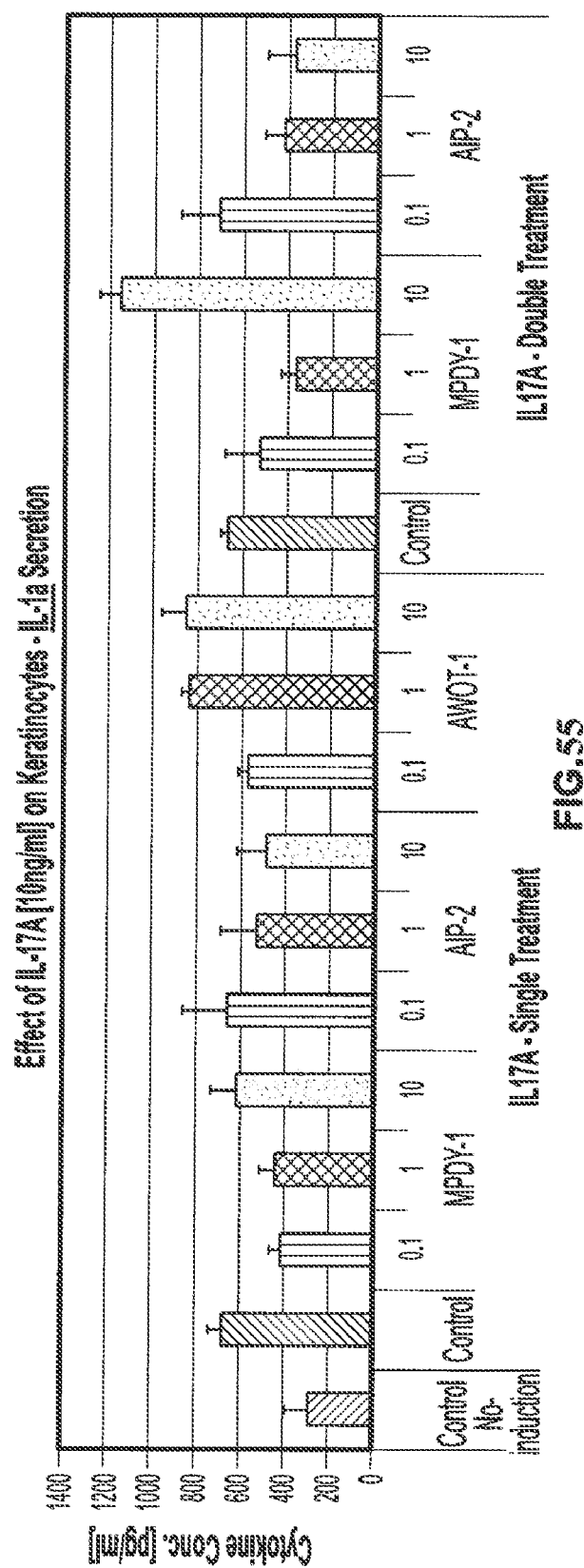
FIG. 55 is a histogram comparing cytokine secretion in IL-17A activated keratinocytes treated with peptide PKCα inhibitors MPDY-1 (SEQ ID NO: 21), AWOT-1 (SEQ ID NO: 5), and AIP-2 (SEQ ID NO: 20).
Figure 56:
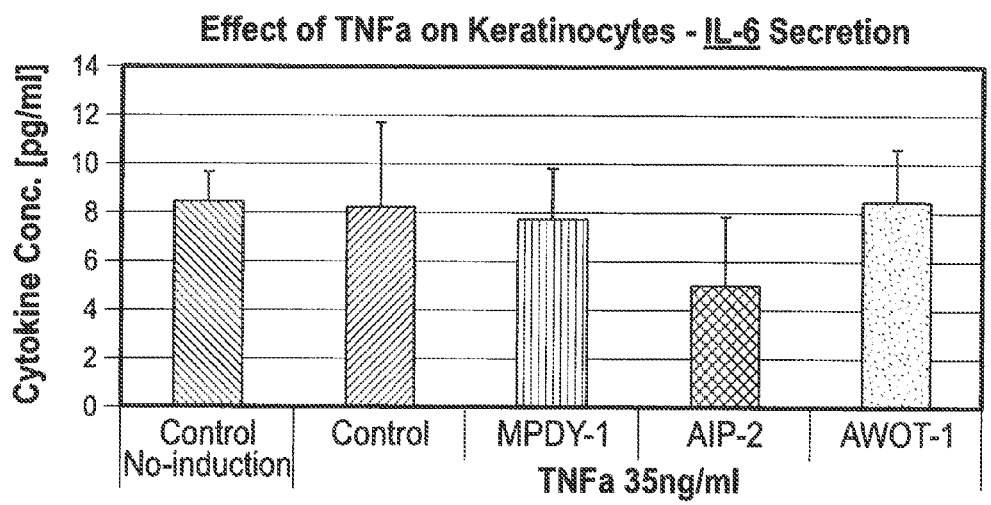
FIG. 56 is a histogram comparing cytokine secretion in TNFα activated keratinocytes treated with peptide PKCα inhibitors MPDY-1 (SEQ ID NO: 21), AWOT-1 (SEQ ID NO: 5), and AIP-2 (SEQ ID NO: 20).
Figure 57:
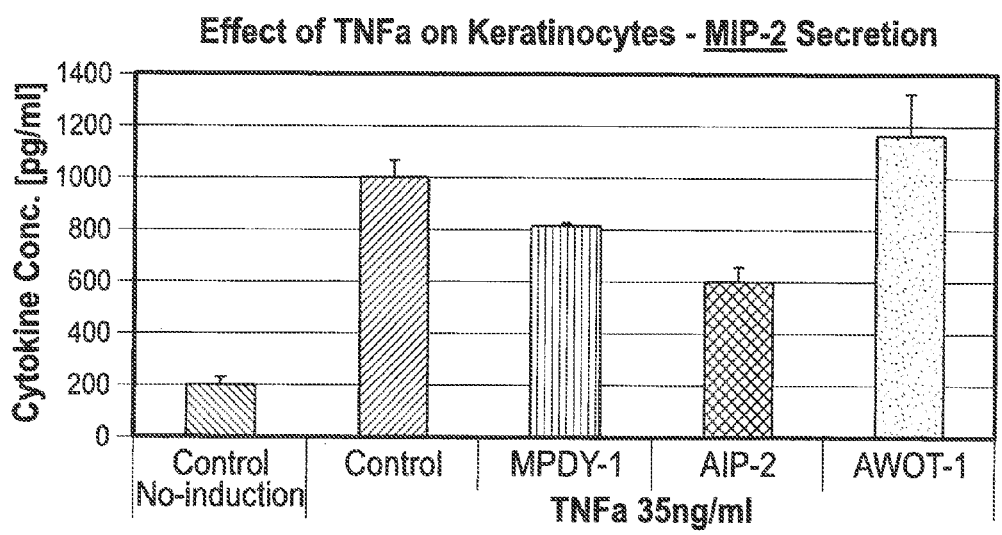
FIG. 57 is a histogram comparing cytokine secretion in TNFα activated keratinocytes treated with peptide PKCα inhibitors MPDY-1 (SEQ ID NO: 21), AWOT-1 (SEQ ID NO: 5), and AIP-2 (SEQ ID NO: 20).
Figure 58:
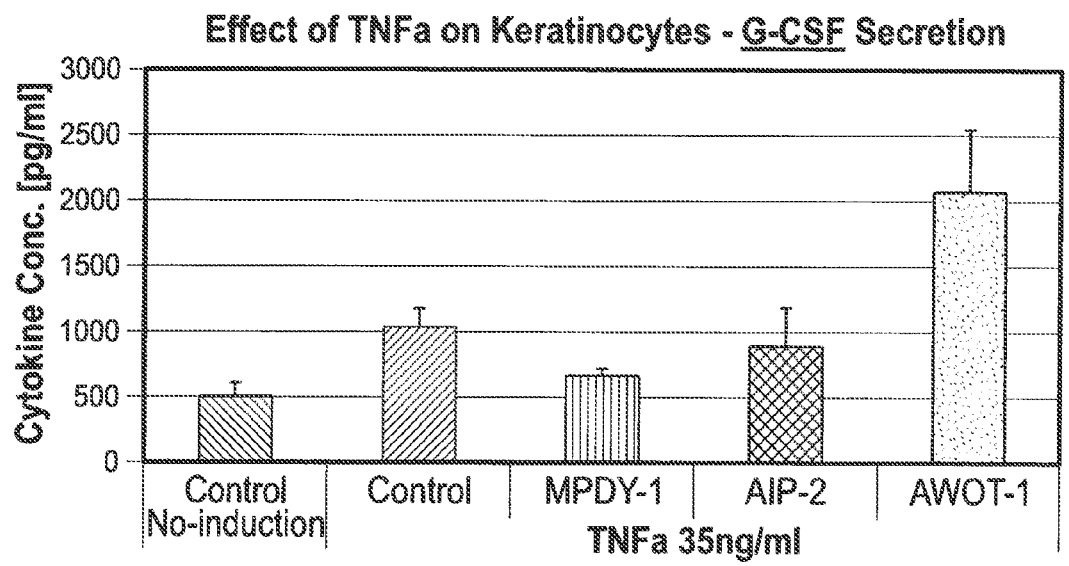
FIG. 58 is a histogram comparing cytokine secretion in TNFα activated keratinocytes treated with peptide PKCα inhibitors MPDY-1 (SEQ ID NO: 21), AWOT-1 (SEQ ID NO: 5), and AIP-2 (SEQ ID NO: 20).
Figure 59:
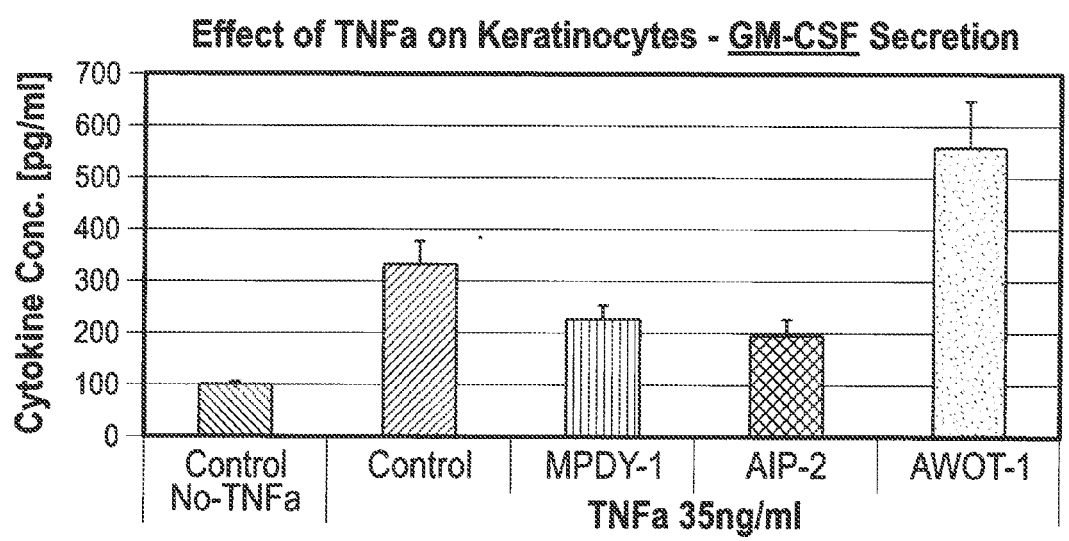
FIG. 59 is a histogram comparing cytokine secretion in TNFα activated keratinocytes treated with peptide PKCα inhibitors MPDY-1 (SEQ ID NO: 21), AWOT-1 (SEQ ID NO: 5), and AIP-2 (SEQ ID NO: 20).
Figure 60:
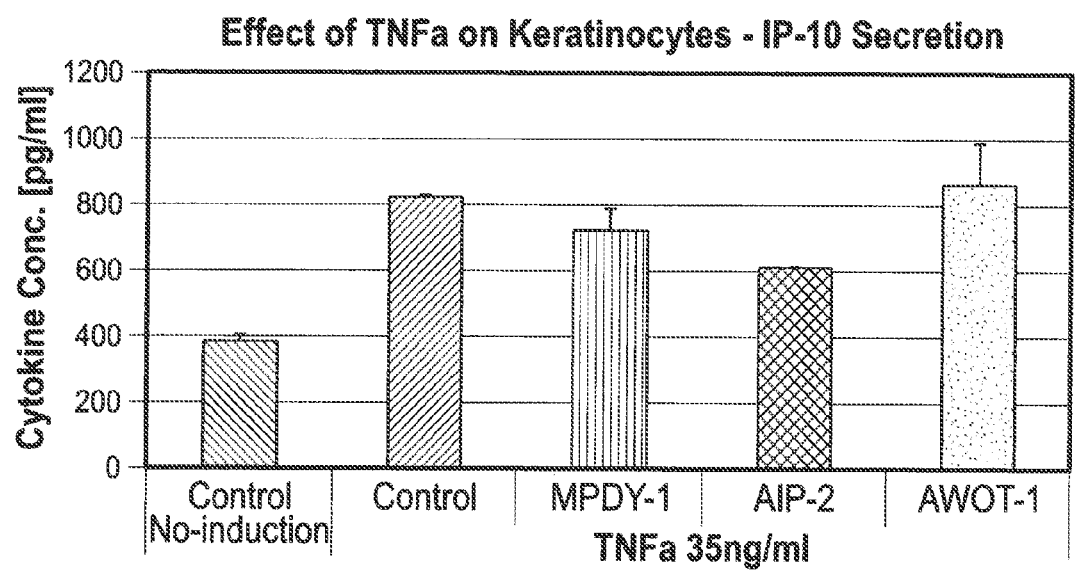
FIG. 60 is a histogram comparing cytokine secretion in TNFα activated keratinocytes treated with peptide PKCα inhibitors MPDY-1 (SEQ ID NO: 21), AWOT-1 (SEQ ID NO: 5), and AIP-2 (SEQ ID NO: 20).
Figure 61:
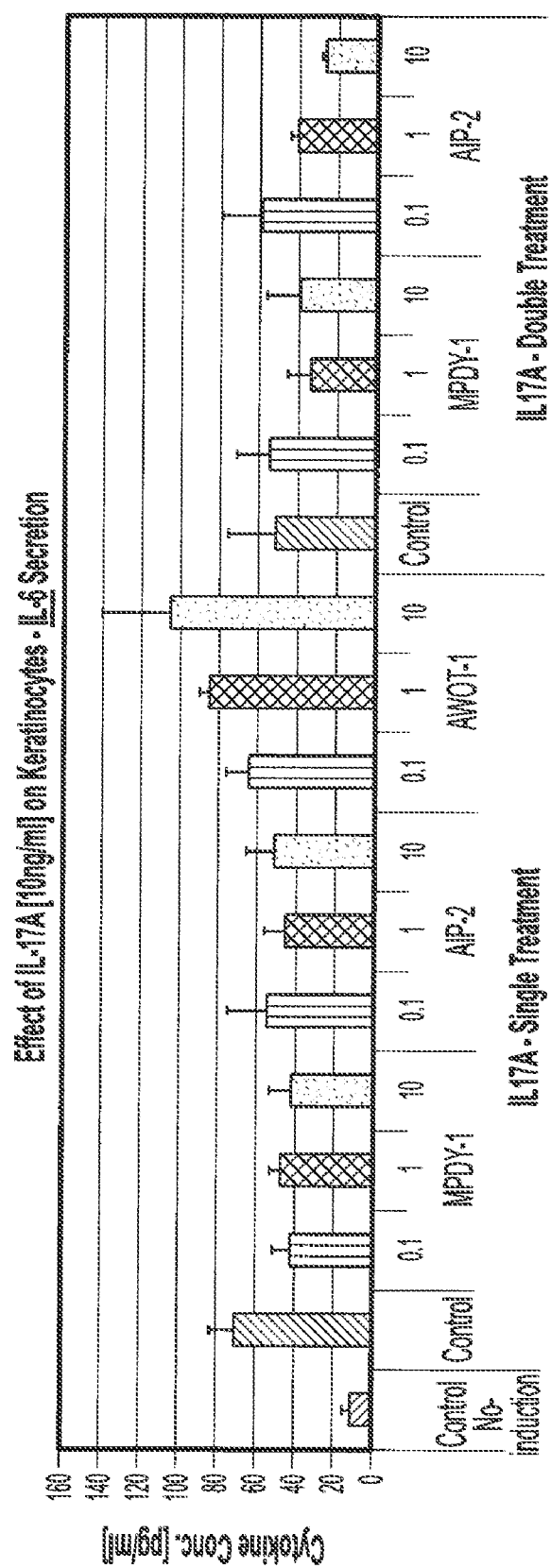
FIG. 61 is a histogram comparing cytokine secretion in IL-17A activated keratinocytes treated with peptide PKCα inhibitors MPDY-1 (SEQ ID NO: 21), AWOT-1 (SEQ ID NO: 5), and AIP-2 (SEQ ID NO: 20).
Figure 66:
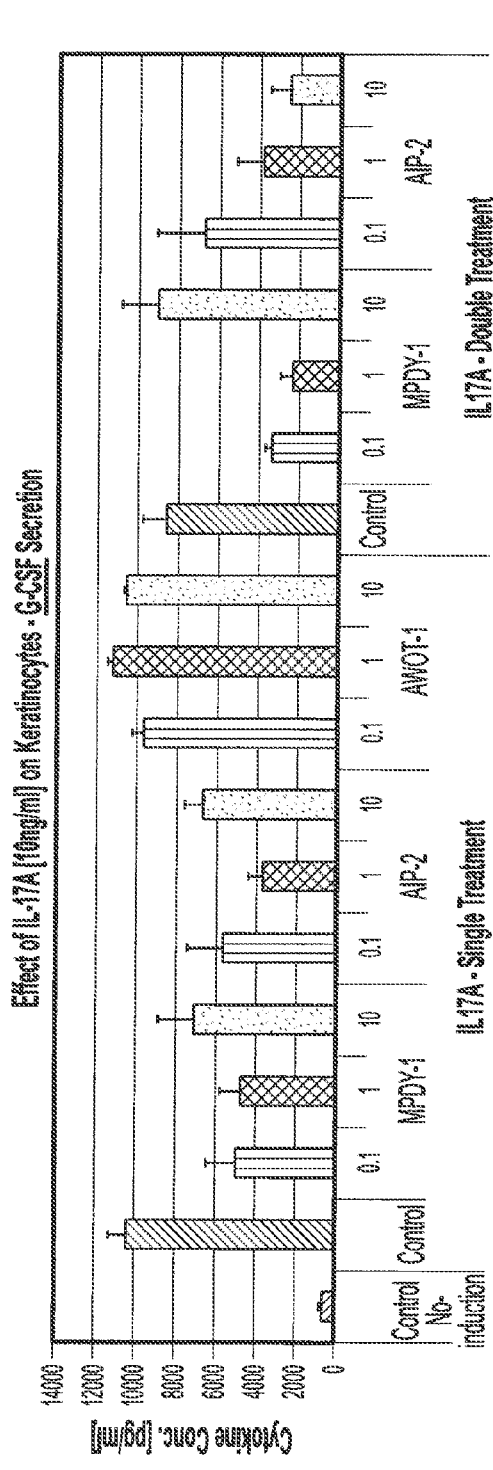
FIG. 66 is a histogram comparing cytokine secretion in IL-17A activated keratinocytes treated with peptide PKCα inhibitors MPDY-1 (SEQ ID NO: 21), AWOT-1 (SEQ ID NO: 5), and AIP-2 (SEQ ID NO: 20).
Figure 67:
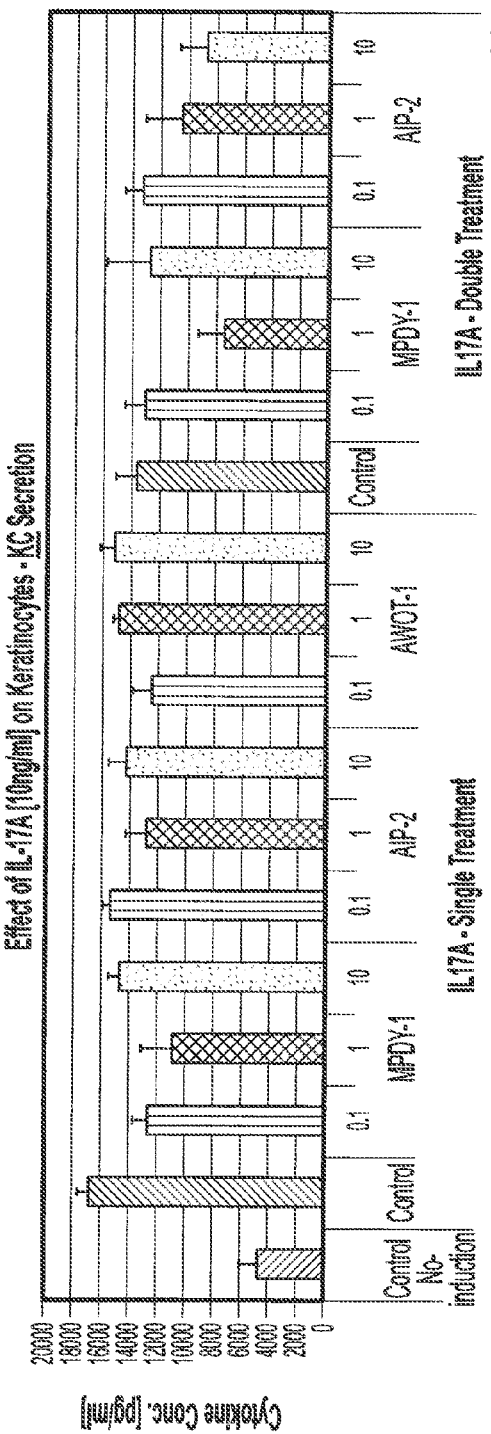
FIG. 67 is a histogram comparing cytokine secretion in IL-17A activated keratinocytes treated with peptide PKCα inhibitors MPDY-1 (SEQ ID NO: 21), AWOT-1 (SEQ ID NO: 5), and AIP-2 (SEQ ID NO: 20).
Figure 68:
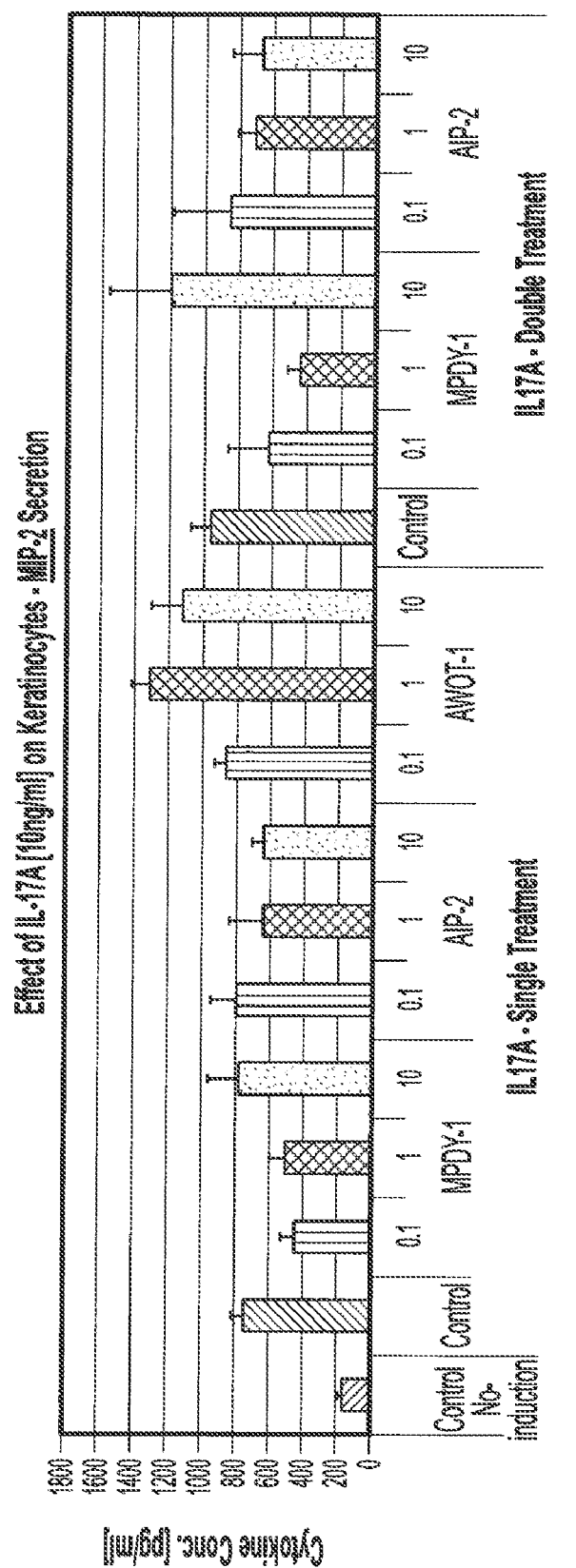
FIG. 68 is a histogram comparing cytokine secretion in IL-17A activated keratinocytes treated with peptide PKCα inhibitors MPDY-1 (SEQ ID NO: 21), AWOT-1 (SEQ ID NO: 5), and AIP-2 (SEQ ID NO: 20).
Figure 69:
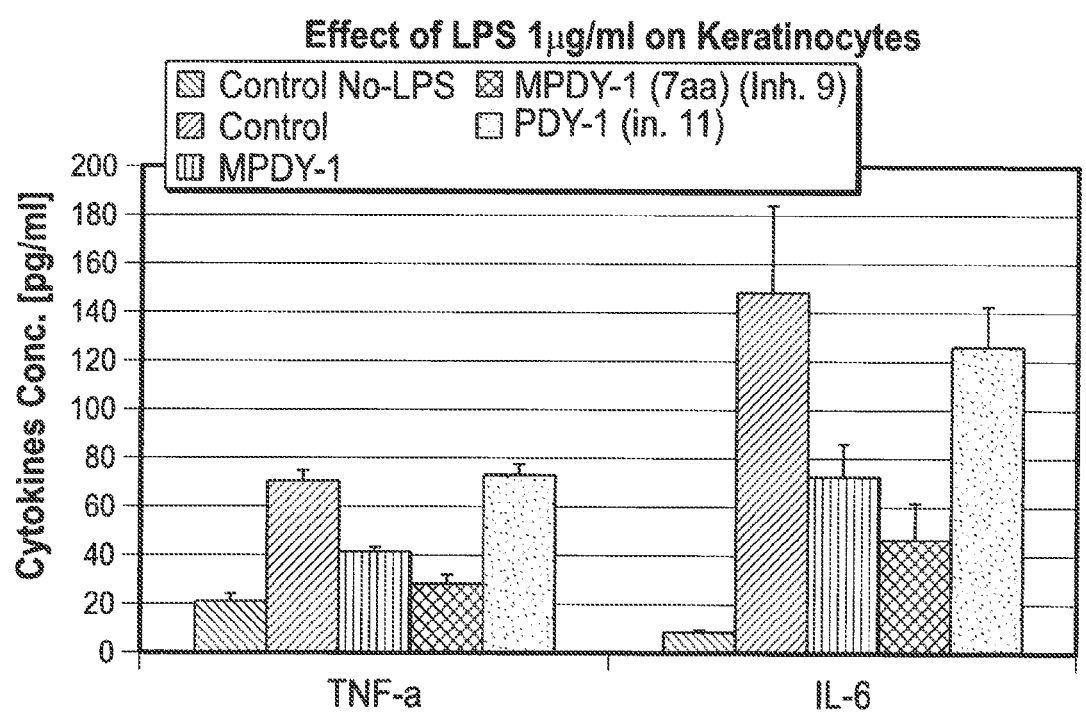
FIG. 69 is a histogram comparing cytokine secretion in LPS activated keratinocytes treated with peptide PKCα inhibitors MPDY-1 (SEQ ID NO: 21) and PDY-1 (AWOT, SEQ ID NO: 5), and AIP-2 (SEQ ID NO:20).

Various other PKCα inhibitors were also shown to decrease cytokine secretion in activated keratinocytes. To determine their effects, keratinocytes were derived from newborn BALB/C mice skin. The cells were incubated for 5 days in 24 wells plate. Cells were then incubated with PBS−/− as control or stimulated by LPS, TNFα, or IL-17. PKCα inhibitors were added as indicated. Medium containing secreted cytokines was collected after 48 hr and analyzed using ELISA. FIG. 40 is a tabular summary of cytokine secretion.

after 48 hr and analyzed using ELISA. FIG. 35 is a tabular summary showing cytokine secretion in splenocytes stimulated with LPS. DAP-1 was shown to significantly decease inflammatory cytokine secretion in both keratinocytes and splenocytes. Cytokine secretion in keratinocytes stimulated by TNFα: following stimulation with 35 ng/ml TNFα. And treatment with 10 μg/ml of DAP-1, the cytokine levels of IL-1α, G-CSF, MIP-2 and KC were reduced by 95%, 70%, 20% and 30# respectively.

PKCε inhibitors were also shown to have an anti-inflammatory effect on keratinocytes. Keratinocytes were derived from newborn BALB/C mice skin. The cells were incubated for 5 days in 24 wells plate. Cells were then incubated with PBS−/− as control or stimulated by LPS or TNFα. The PKCε-inhibitors EPIP-1 (SEQ ID NO: 20), EPIP-2 (SEQ ID NO: 21), or EPIP-4 (SEQ ID NO: 23) were added. Medium containing secreted cytokines was collected after 48 hr and analyzed using ELISA. FIGS. 36-39 show the results for secretion of specific cytokines while Table 8 summarizes cytokine secretion for the various PKCε inhibitors:

TABLE 8 cytokine secretion following treatment with PKCε inhibitors

| Stimulation | Treatment | Results |
| --- | --- | --- |
| TNF [35 ng/ml] | EPIP-1 [10 g/ml] | IL-6 (−95%), G-CSF (−85%), IP-10 (−45%) |
| | EPIP-2 [1 g/ml] | IL-6 (−95%), G-CSF (−100%), IP-10 (−65%) |
| | EPIP-2 [10 g/ml] | IL-6 (−95%), G-CSF (−100%), IP-10 (−40%) |
| | EPIP-4 [1 g/ml] | IL-6 (−100%), G-CSF (−100%), IP-10 (−80%) |
| LPS 1 [μg/ml] | EPIP-1 [10 g/ml] | IL-6 (−55%), G-CSF (−70%), IP-10 (−60%), KC (−100%) |
| | EPIP-2 [1 g/ml] | IL-6 (−40%), G-CSF (−50%), IP-10 (−50%), KC (−90%) |
| | EPIP-2 [10 g/ml] | IL-6 (−55%), G-CSF (−75%), IP-10 (−40%), KC (−90%) |
| | EPIP-4 [1 g/ml] | IL-6 (−55%), G-CSF (−75%), IP-10 (−60%), KC (−100%) |

Several of the PKCε inhibitors were shown to significantly decease inflammatory cytokine secretion in keratinocytes.

In summary, the mechanism of action of PKC isoform inhibitors and activators was determined implicating their use as an effective therapy for inflammation and inflammatory disease. Such peptides were shown to 1) normalize epidermal differentiation markers expression by reducing terminal differentiation; 2) attenuate abnormal hyper-proliferation; 3) regulate skin structure and augment skin strength; and 4) down-regulate inflammation by differentially affecting different cell type recruitment and activation in various steps of the inflammatory process.

Figure 30:
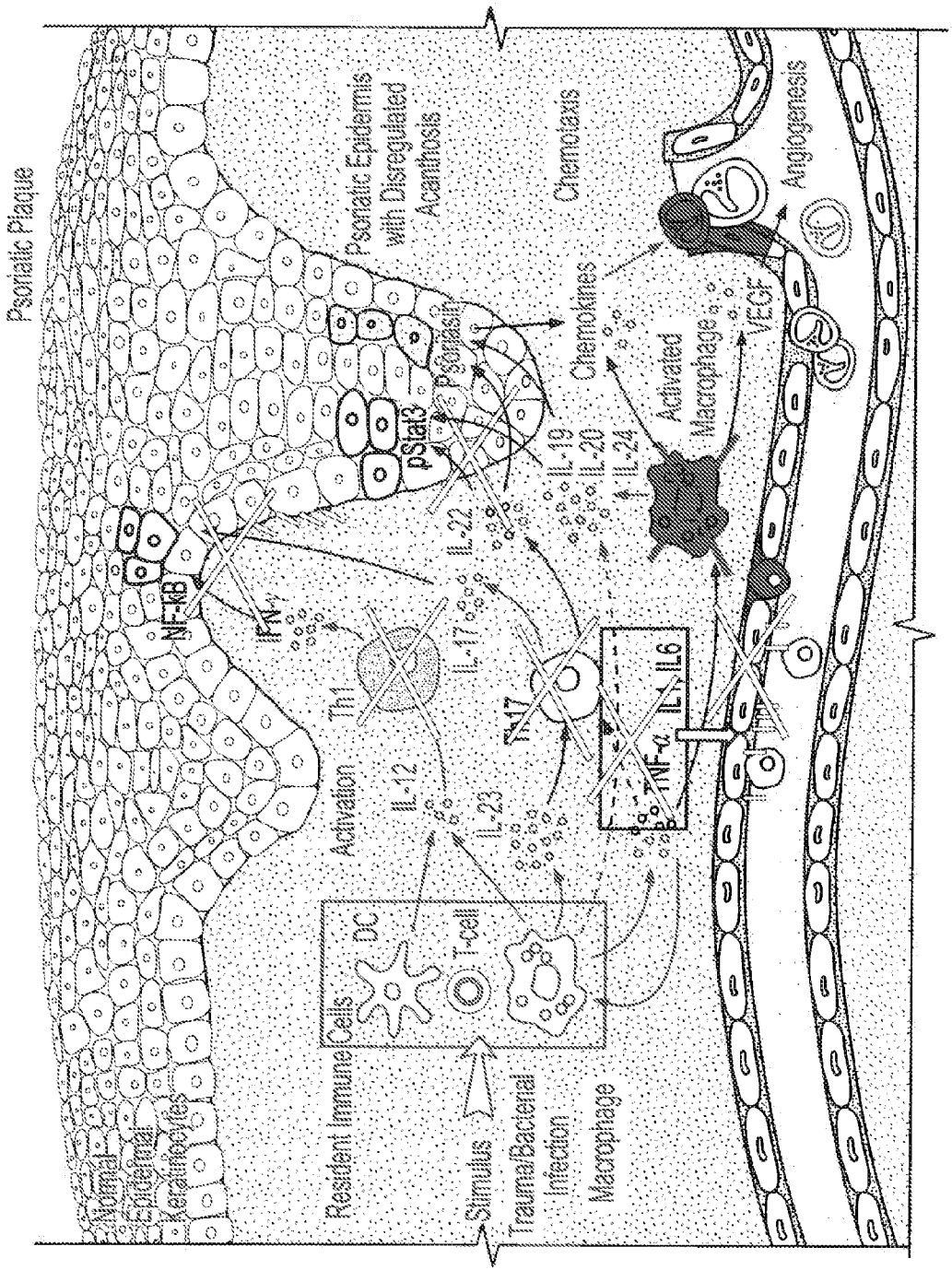
FIG. 30 is a graphical representation showing a schema of the overall effect of HO/02/10 on the psoriatic related pathway.

FIG. 30 shows a schema depicting the overall effect of the PKC isoform inhibitors and activators of the present disclosure on the skin inflammatory and psoriatic related pathway. The scheme summarizes the inhibitory effect of the inhibitors and activators on various cell types and inflammatory stages in the skin. PKC isoform inhibitors and activators inhibit secretion of pro-inflammatory cytokines (such as, IL-1, IL-6 and TNFα) by resident skin immune cells. Accordingly, a decrease in endothelial cells and keratinocytes activation is achieved, resulting a significant reduction in ICAM-1 expression, chemokines secretion and reduce in leukocytes infiltration to the site of inflammation, including neutrophils, macrophages, and T-cells. Cytokines involved in the development and progression of the Th1 and Th17 pathways, both main pathways in psoriasis, were also down regulated.

Example 7

In Vivo Assessment of Pruritus Treatment

Figure 33:
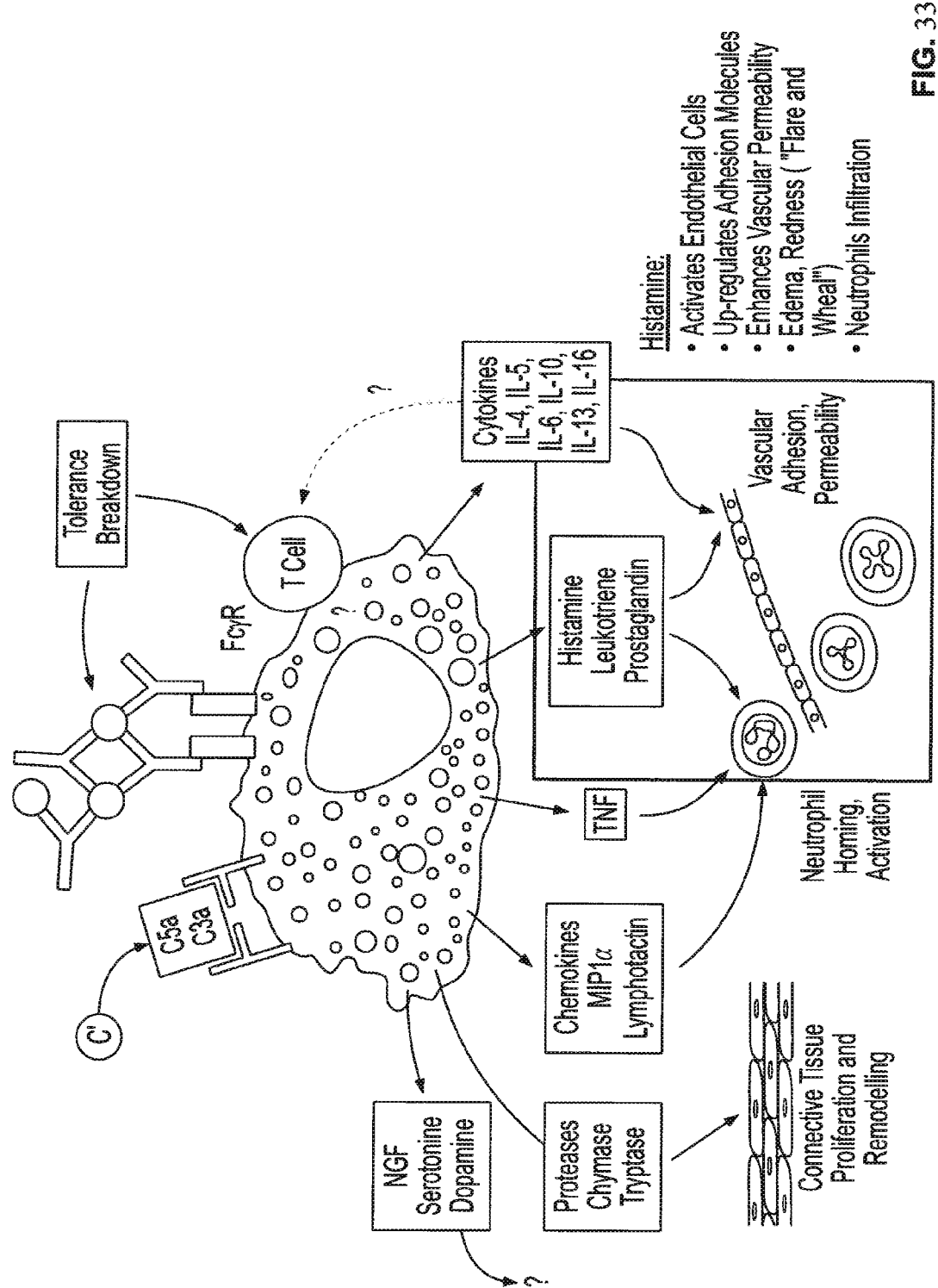
FIG. 33 is a pictorial representation of the mechanism of action of histamine that is used in a prick test model to assess MPDY-1 (SEQ ID NO:21) effect on pruritus.

A prick test model utilizing histamine to assess pruritus was developed as shown in FIG. 33. Forearms of individual subjects were injected with histamine solution and placebo. The formulation of Example 4 was topically applied with MPDY-1 at various concentrations and pruritus was assessed over a time course as shown, for example in FIG. 34.

This test was performed by placing a drop of a solution containing a possible allergen on the skin, and a series of scratches or needle pricks allow the solution to enter the skin. The extract enters into the outer layer of the skin (epidermis) using a fine needle (such as a. 26G disposable needle). This testing is not painful, and generally there is no bleeding involved since the needle only scratches the surface of the skin. If the skin develops a red, raised itchy area (called a wheal), it is as a result of allergic reaction to that allergen. This is called a positive reaction. A drop of extract is introduced through a fine needle (such as a No. 26 disposable needle). The test causes no discomfort and minimal trauma so that controls and negative test show only the site of the prick; if anything.

26G needles were utilized to introduce histamine stock (Histatrol Positive Control Histamine, 1 mg/ml, code #HIST14999V, Trupharm). The test was conducted on healthy volunteers in a double-blind, randomized test. The formulations were applied on the forearms. Three treatment areas were chosen and marked (the surface of the forearm from the elbow to the wrist was divided transversely into proximal, middle and distal thirds); the areas were pricked prior the below treatments.

An area was treated with the active formulation in a double-blind manner, for 10 minutes—marked as A.

An area was treated with the Placebo in a double-blind manner, for 10 minutes—marked as C.

A color photograph was taken at time zero ($T_0$), after 10, 20, 30 minutes.

Pruritus questionnaire was answered by the subjects 5 and 15 minutes after treatment.

In one study, three subjects were treated, in the left or right arm, with MDPY-1 in gel or cream formulations, or with control formulations, as shown in Table 9.

Subjects were provided with pruritus sensation forms and asked to indicate the level of pruritus sensed from 0 (no response) to 4 (uncontrollable pruritus) at different time intervals. Results are shown in Table 7 below.

TABLE 9

Prick Test Groups, treatments and results

| | | | Pruritus score after minutes of histamine | |
| --- | --- | --- | --- | --- |
| Subject & Site | Forearm treated | Treatment | 5 minutes | 15 minutes |
| 1-A5 | left | 10 ppm MPDY-1 in gel | 2 | 0 |
| 1-A4 | | 10 ppm MPDY-1 in cream | 1 | 0 |
| 2-A2 | | MPDY-1 10 μg/ml in DPBS | 2 | 0 |
| 2-A5 | | MPDY-1 10 μg/ml in DPBS | 1 | 0 |
| 3-A4 | | 10 ppm MPDY-1 in cream | 1 | 0 |
| 3-A1 | | MPDY-1 1 μg/ml in DPBS | 3 | 1 |
| 1-C2 | right | Gel W/O active material | 3 | 4 |
| 1-C1 | | Cream W/O active material | 4 | 4 |
| 2-C3 | | DPBS | 4 | 4 |
| 2-C2 | | Gel W/O Active material | 3 | 4 |
| 3-C1 | | Cream W/O active material | 3 | 3 |
| 3-C3 | | DPBS | 4 | 4 |

Figure 34:
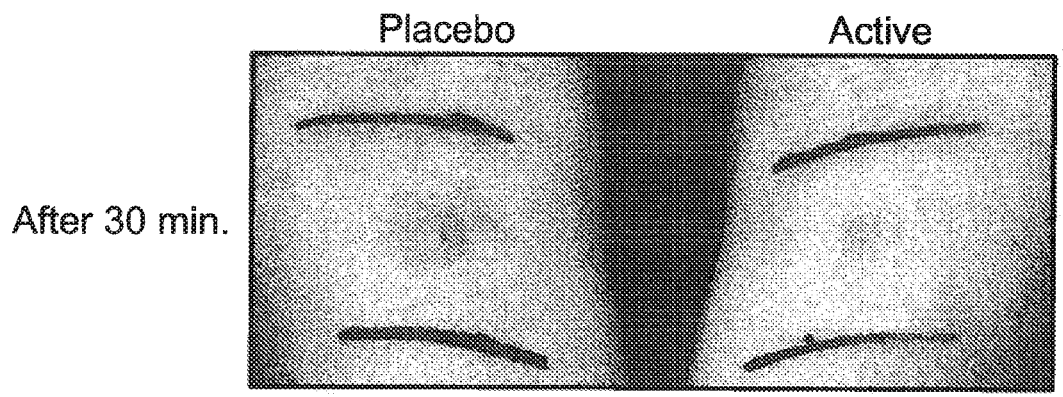
FIG. 34 is a pictorial representation showing subject's forearms injected with histamine and treated with or without MPDY-1.
Figure 36:
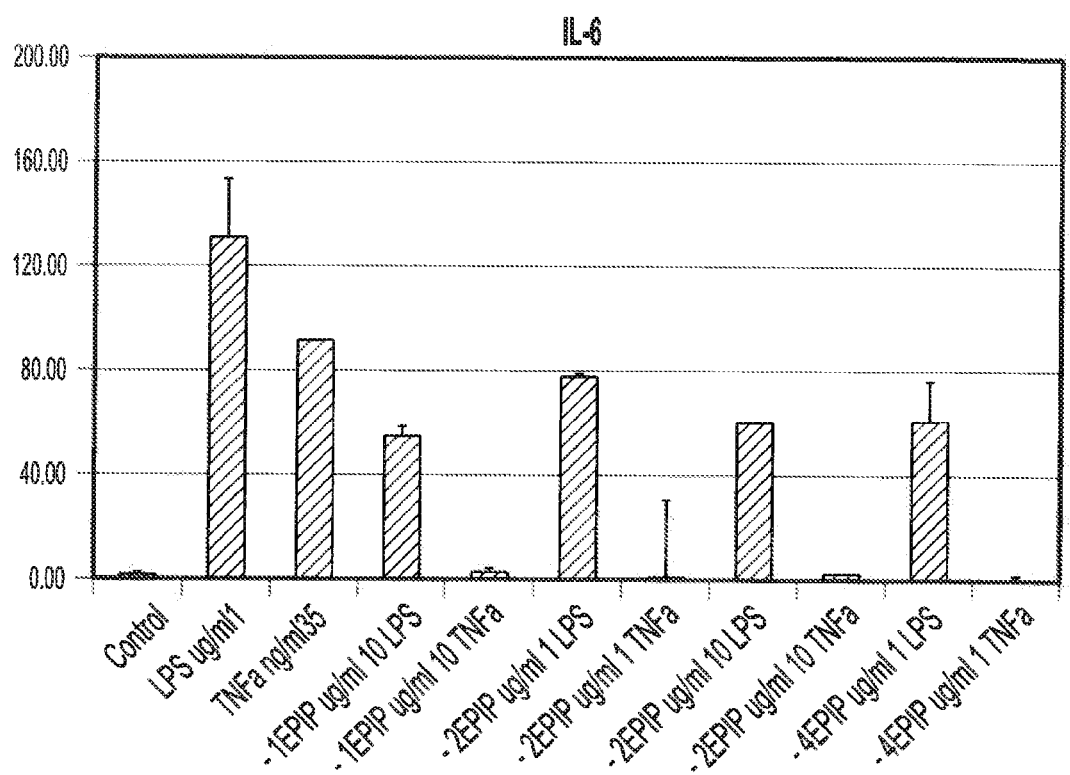
FIG. 36 is a histogram showing comparing cytokine secretion in keratinocytes treated with LPS or TNFα and various PKCε inhibitors.
Figure 37:
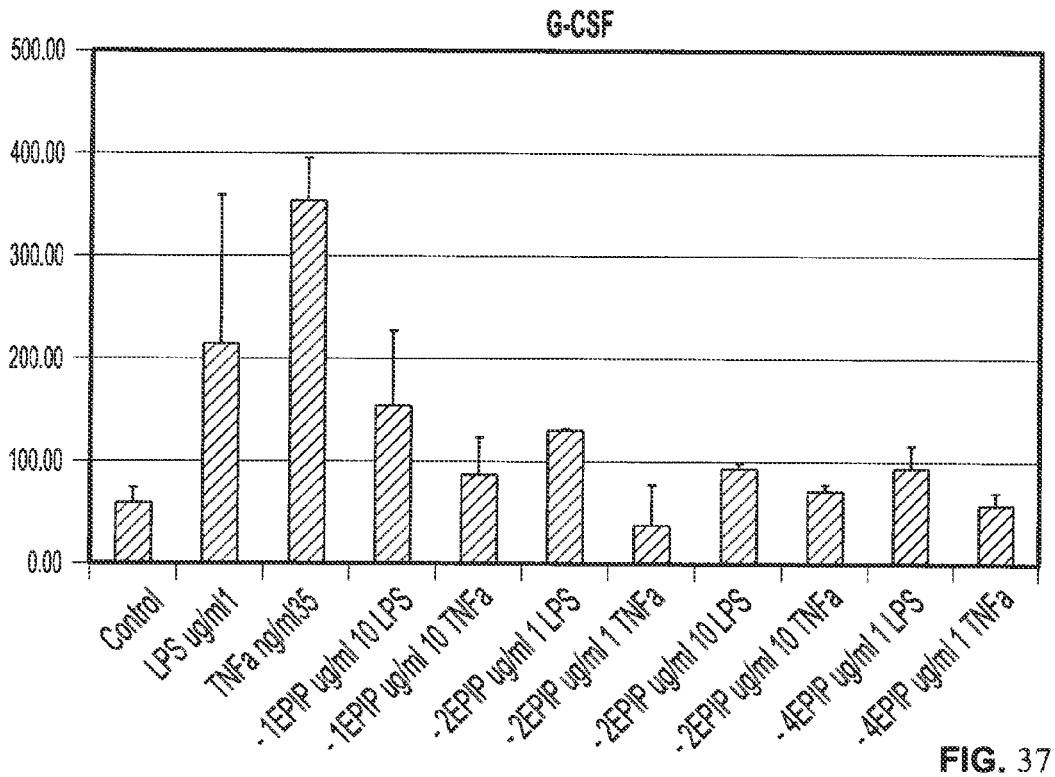
FIG. 37 is a histogram showing comparing cytokine secretion in keratinocytes treated with LPS or TNFα and various PKCε inhibitors.
Figure 38:
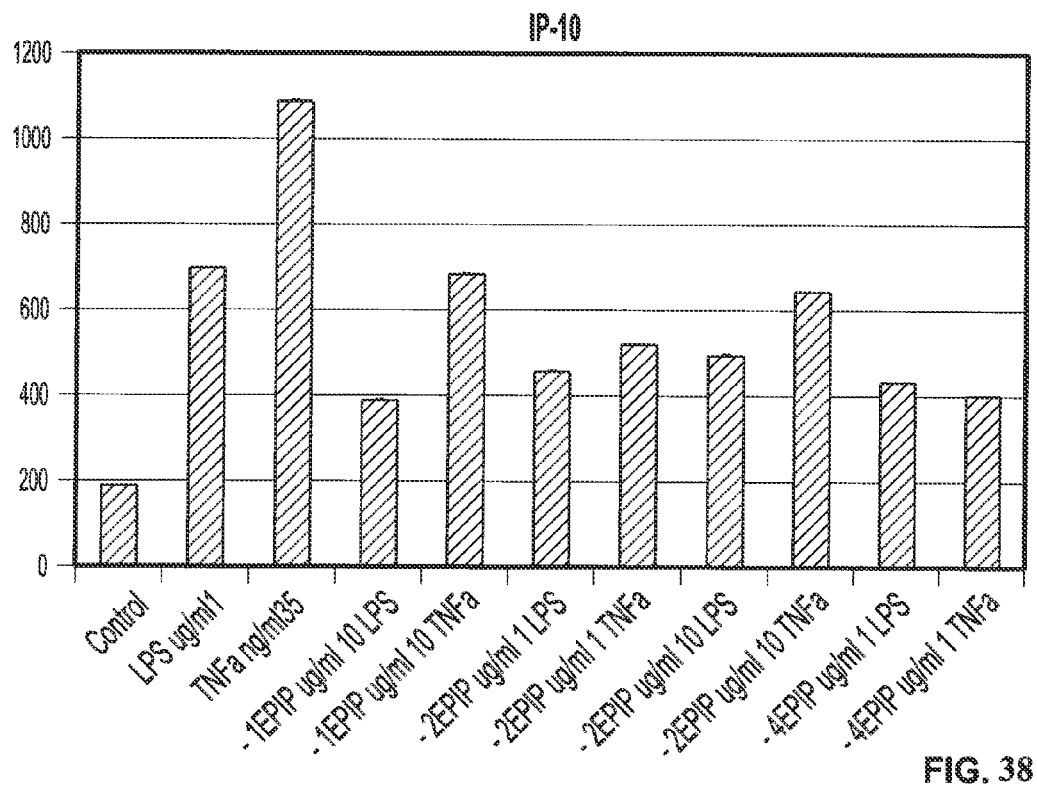
FIG. 38 is a histogram showing comparing cytokine secretion in keratinocytes treated with LPS or TNFα and various PKCε inhibitors.
Figure 39:
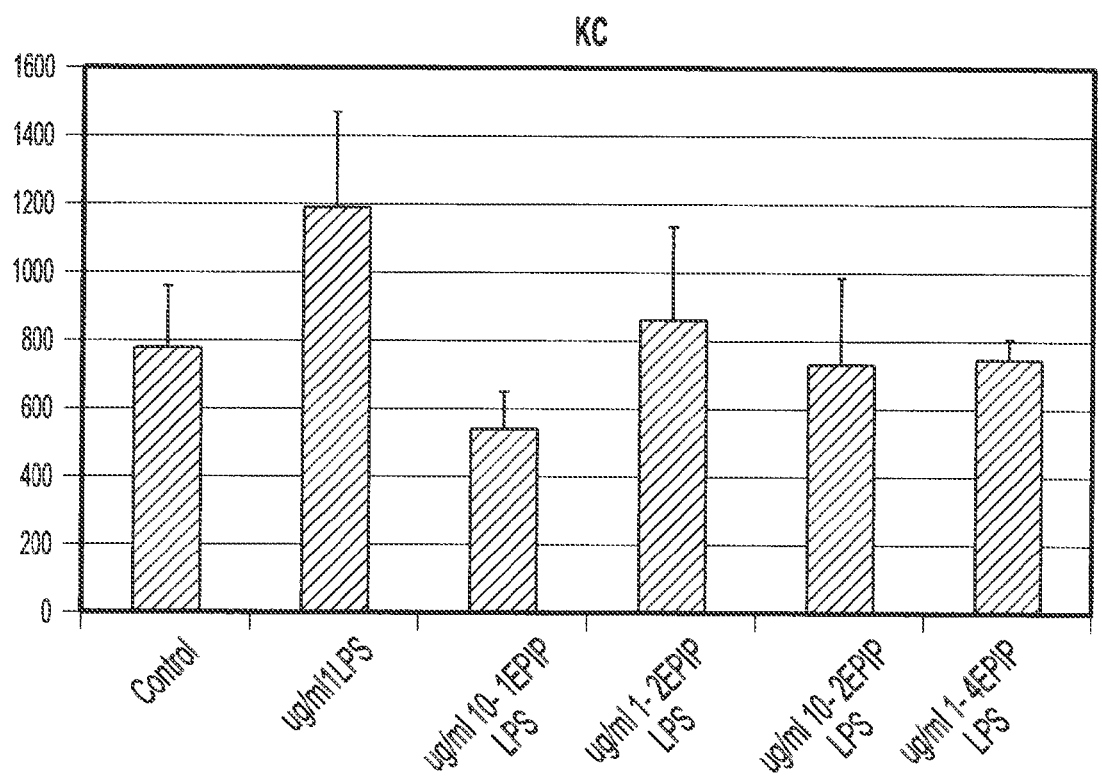
FIG. 39 is a histogram showing comparing cytokine secretion in keratinocytes treated with LPS or TNFα and various PKCε inhibitors.

Additionally, as is evident for example in FIG. 34, application of MPDY-1 significantly attenuated redness, inflammation and pruritus as compared with control over the time course.

Example 8

Cytokine Sectetion in Splenocytes Following Treatment with PKC Inhibitory Peptides Inhibitory effect on activated splenocytes: Splenocytes were derived from B6 mice. Red blood cells were removed and cells were treated with DPBS$^{-/-}$, LPS (100 ng/ml) or TNF alpha (25 ng/ml) in the presence or absence of the indicated peptide inhibitors. Medium containing secreted cytokines was collected after 48 hr and analyzed using ELISA.

Table 10 describes the reduction in cytokine secretion following stimulation of splenocytes with LPS or TNFα and treatment with various peptide inhibitors of PKC.

TABLE 10

Reduction in cytokine secretion in splenocytes

| Stimulant | Peptide/conc. | G-CSF | GM-CSF | IFN-γ | IL-10 | IL-17 | IL-1a | IL-4 | IL-6 | IP-10 | KC | MIP-2 |
|---|---|---|---|---|---|---|---|---|---|---|---|---|
| LPS 1 µg/ml | EPIP.2 1 µg/ml | 30 | 20 | | | | 25 | 10 | 10 | 20 | 10 | 25 |
| | EPIP.2 10 µg/ml | 50 | 40 | 15 | | 40 | 45 | 20 | 25 | 15 | 40 | 35 |
| | EPIP.4 1 µg/ml | | | | | | | | 15 | | | |
| | EPIP.4 10 µg/ml | | | | | | | | 20 | | | 10 |
| | MPE-1 1 µg/ml | | | | | | 10 | 10 | | 10 | | 10 |
| | MPE-1 10 µg/ml | 20 | | | 15 | 15 | 20 | 15 | 15 | 15 | 20 | 15 |
| TNFα 25 ng/ml | EPIP.2 1 µg/ml | | | | | 80 | | 15 | | 20 | | |
| | EPIP.2 10 µg/ml | 30 | | | 30 | 85 | | | 25 | 10 | | |
| | EPIP.4 1 µg/ml | 45 | | 25 | 30 | 85 | 10 | | 15 | | | |
| | EPIP.4 10 µg/ml | 20 | | 55 | 10 | 90 | | | | 15 | | |
| | MPE-1 1 µg/ml | 40 | | | | 90 | | | 25 | | | |
| | MPE-1 10 µg/ml | 15 | | | | 90 | | | | | | |

Tables 11 and 12 summarize the effects of the peptides EPIP1 (SEQ ID NO: 6), EPIP2 (SEQ ID NO: 7), EPIP3 (SEQ ID NO: 8), EPIP4 (SEQ ID NO: 9), DAP1 (SEQ ID NO: 16), and DAP3 (SEQ ID NO: 15) on several parameters related to inflammation of skin and epithelial tissues. The parameters modulated by the tested peptides are: differentiation and proliferation markers, migration and activity on the immune system cells, splenocytes and keratinocytes.

TABLE 11

Effects of the PKC epsilon inhibitory peptides EPIP1, EPIP2, EPIP3, and EPIP4 on cytokine secretion in keratinocytes

| PKC epsilon inhibitors | Differentiation markers | Proliferation markers | Migration | Immunology system |
|---|---|---|---|---|
| EPIP1 | Reduces granular and spainous Differentiation (1 µg/ml, 10 µg/ml) | Induces (PCNA) | Induces (200%) | TNFa stim (35 ng/ml 1 µg/ml of peptide: Reduces proinflammatory cytokines IL-6 (95%), systemic cytokines G-SCF(−85%) and Chemokines IP 10 (45%) LPS (1 µg/ml): IL-6 (−55%), G-CSF (−70%), IP-10 (−60%), KC (−100%) |
| EPIP2 | Reduces granular Slightly induces spainous Differentiation (10 µg/ml) | Induces (1 µg/ml) Slightly Reduce 10 µg/ml | Induces (200%) | TNFa stim (35 ng/ml 1 µg/ml of peptide: Reduces proinflammatory cytokines IL-6 (95%), systemic cytokines G-SCF (100%) and Chemokines IP 10 (65%) LPS (1 µg/ml): IL-6 (−40%), G-CSF (−50%), IP-10 (−50%), KC (−90%) |
| EPIP3 | Reduces granular Does not effect of spainous differentiation | Induces | Induces (200%) | Reduces pro-inflammatory cytokines, chemokines, better than MPDY-1 upon LPS and TNFa activation. IL-17: similar effect to MPDY-1 |

TABLE 11-continued

Effects of the PKC epsilon inhibitory peptides EPIP1, EPIP2, EPIP3, and EPIP4 on cytokine secretion in keratinocytes

| PKC epsilon inhibitors | Differentiation markers | Proliferation markers | Migration | Immunology system |
|---|---|---|---|---|
| EPIP4 | No influence on granular differentiation but Slightly reduces spainous differentiation | Slightly Induces | Induces (200%) | TNFa stim (35 ng/ml): Reduces proinflammatory cytokines IL-6(−100%), systemic cytokines G-SCF (−100%)) and Chemokines IP 10 (−80%) LPS (1 mg/ml): Reduces proinflammatory IL-6 (−55%), systemic cytokines G-CSF (−75%), and Chemokines IP-10 (−60%), KC (−100%) |

The effect of the PKC epsilon inhibitory peptides on splenocytes is summarized in Table 8.

TABLE 12

Effects of the PKC delta activator peptides DAP1 and DAP3 on cytokine secretion in splenocytes and keratinocytes

| | Keratinocytes physiology | | | Immunology system | |
|---|---|---|---|---|---|
| PKC delta activators | Differentiation markers | Proliferation markers | Migration | Splenocytes | Keratinocytes |
| DAP1 | Slightly induces granular But reduces spainous Differentiation (1 µg/ml, 10 µg/ml) | Reduces (PCNA) | Induces (200%) | Induction: LPS (1 µg/ml) DAP1 (10 µg/ml) significantly reduces systemic cytokine: G-SCF (40%), reduces proinflamatory cytokine: IL-6 (30%) and IL-1α (45%), Reduces Chemokine: KC (32%), as well as TNFa expression (28%). DAP1 (1 µg/ml) induces antiinflamatory cytokine: IL 10 (200%) | Induction: TNFα (35 ng/ml) DAP1 (10 µg/ml)- Reduces systemic cytokine: GM-CSF (50%) and G-SCF (40%) Reduces Chemokines: KC (32%), MIP2 (30%) Reduces proinflamatory cytokine: IL-6 (20%) and IL-1a (40%) |
| DAP3 | induces granular But does not effect or reduce spainous differentiation | induces | Induces (200%) | DAP3 (10 µg/ml) Reduces systemic cytokine: G-SCF (25%), Reduces proinflamatory cytokines: IL-6 (50%) and IL-1α (45%), Reduces Chemokines: KC (20%) and MIP2 (25%) | Induction: TNFα (35 ng/ml) DAP3 (10 µg/ml) Reduces systemic cytokine: GM-CSF and G-SCF (25%), Reduces Chemokines: KC (25%), Reduces proinflamatory cytokine: IL-6 (45%) and IL-1a (50%) |

FIGS. 35-70 depict the experimental data used in summarizing the results in Tables 11 and 12.

As can be seen from the above detailed results, peptide inhibitors of the present invention promote strong attenuation of skin and systemic inflammation and regulate basal keratinocyte differentiation and proliferation. The unique combination of effects enables those peptides to halt the inflammation while controlling the skin physiology, which is a clear benefit when treating dermal and epidermal diseases.

Although the objects of the disclosure have been described with reference to the above example, it will be understood that modifications and variations are encompassed within the spirit and scope of the disclosure. Accordingly, the disclosure is limited only by the following claims.

What is claimed is:

1. An isolated peptide or salts thereof, wherein the isolated peptide:
   comprises SEQ ID NO: 9, SEQ ID NO: 15, SEQ ID NO: 16 or SEQ ID NO: 17;
   is up to 30 amino acids in length; and
   modulates PKC.

2. The isolated peptide according to claim 1 comprising SEQ ID NO: 9 or SEQ ID NO: 16.

3. The isolated peptide according to claim 1, wherein the isolated peptide is connected to a fatty acid at the N-terminus of the isolated peptide, wherein the fatty acid functions as a permeability moiety.

4. A pharmaceutical composition comprising at least one isolated peptide according to claim 1, and a pharmaceutically acceptable vehicle, diluent or excipient.

5. A peptide multimer or salts thereof comprising at least two, identical or different, sequences selected from the group consisting of SEQ ID NOs: 9, 15, 16 and 17, wherein the peptide multimer is up to 60 amino acids in length, and wherein the isolated peptide multimer modulates PKC.

6. The peptide multimer according to claim 5 comprising a SEQ ID NO: 15 or SEQ ID NO:17.

7. The peptide multimer according to claim 5 wherein the peptide multimer is connected to a fatty acid at the N-terminus of the peptide multimer, wherein the fatty acid functions as a permeability moiety.

8. A pharmaceutical composition comprising at least one peptide multimer according to claim 5, and a pharmaceutically acceptable vehicle, diluent or excipient.

* * * * *

SEQUENCE LISTING

<160> NUMBER OF SEQ ID NOS: 26

<210> SEQ ID NO 1
<211> LENGTH: 6
<212> TYPE: PRT
<213> ORGANISM: Artificial Sequence
<220> FEATURE:
<223> OTHER INFORMATION: Synthetic peptide

<400> SEQUENCE: 1

Phe Ala Arg Lys Gly Ala
1               5

<210> SEQ ID NO 2
<211> LENGTH: 8
<212> TYPE: PRT
<213> ORGANISM: Artificial Sequence
<220> FEATURE:
<223> OTHER INFORMATION: Synthetic peptide

<400> SEQUENCE: 2

Phe Ala Arg Lys Gly Ala Arg Gln
1               5

<210> SEQ ID NO 3
<211> LENGTH: 8
<212> TYPE: PRT
<213> ORGANISM: Artificial Sequence
<220> FEATURE:
<223> OTHER INFORMATION: Synthetic peptide

<400> SEQUENCE: 3

Thr Leu Asn Pro Gln Trp Glu Ser
1               5

<210> SEQ ID NO 4
<211> LENGTH: 7
<212> TYPE: PRT
<213> ORGANISM: Artificial Sequence
<220> FEATURE:
<223> OTHER INFORMATION: Synthetic peptide

<400> SEQUENCE: 4

Phe Ala Arg Lys Gly Ala Leu
1               5

<210> SEQ ID NO 5
<211> LENGTH: 9
<212> TYPE: PRT
<213> ORGANISM: Artificial Sequence
<220> FEATURE:
<223> OTHER INFORMATION: Synhtetic peptide

<400> SEQUENCE: 5

Phe Ala Arg Lys Gly Ala Leu Arg Gln
1               5

<210> SEQ ID NO 6
<211> LENGTH: 8
<212> TYPE: PRT
<213> ORGANISM: Artificial Sequence
<220> FEATURE:
<223> OTHER INFORMATION: Synthetic peptide

<400> SEQUENCE: 6

Glu Ala Val Ser Leu Lys Pro Thr

-continued

```
<210> SEQ ID NO 7
<211> LENGTH: 8
<212> TYPE: PRT
<213> ORGANISM: Artificial Sequence
<220> FEATURE:
<223> OTHER INFORMATION: Synthetic peptide

<400> SEQUENCE: 7

Pro Tyr Ile Ala Leu Asn Val Asp
1               5

<210> SEQ ID NO 8
<211> LENGTH: 5
<212> TYPE: PRT
<213> ORGANISM: Artificial Sequence
<220> FEATURE:
<223> OTHER INFORMATION: Synthetic peptide

<400> SEQUENCE: 8

Pro Ala Trp His Asp
1               5

<210> SEQ ID NO 9
<211> LENGTH: 12
<212> TYPE: PRT
<213> ORGANISM: Artificial Sequence
<220> FEATURE:
<223> OTHER INFORMATION: Synthetic peptide

<400> SEQUENCE: 9

Leu Glu Pro Glu Ala Ala Ala Ala Ala Ala Gly Lys
1               5                   10

<210> SEQ ID NO 10
<211> LENGTH: 7
<212> TYPE: PRT
<213> ORGANISM: Artificial Sequence
<220> FEATURE:
<223> OTHER INFORMATION: Synthetic peptide

<400> SEQUENCE: 10

His Phe Glu Asp Trp Ile Asp
1               5

<210> SEQ ID NO 11
<211> LENGTH: 7
<212> TYPE: PRT
<213> ORGANISM: Artificial Sequence
<220> FEATURE:
<223> OTHER INFORMATION: Synthetic peptide

<400> SEQUENCE: 11

Val Tyr Val Ile Ile Asp Leu
1               5

<210> SEQ ID NO 12
<211> LENGTH: 5
<212> TYPE: PRT
<213> ORGANISM: Artificial Sequence
<220> FEATURE:
<223> OTHER INFORMATION: Synthetic peptide

<400> SEQUENCE: 12

Lys Arg Thr Leu Arg
1               5
```

```
<210> SEQ ID NO 13
<211> LENGTH: 17
<212> TYPE: PRT
<213> ORGANISM: Artificial Sequence
<220> FEATURE:
<223> OTHER INFORMATION: Synthetic peptide

<400> SEQUENCE: 13

Thr Arg Lys Arg Gln Arg Ala Met Arg Arg Val His Gln Ile Asn
1               5                   10                  15

Gly

<210> SEQ ID NO 14
<211> LENGTH: 7
<212> TYPE: PRT
<213> ORGANISM: Artificial Sequence
<220> FEATURE:
<223> OTHER INFORMATION: Synthetic peptide

<400> SEQUENCE: 14

His Phe Glu Asp Trp Ile Asp
1               5

<210> SEQ ID NO 15
<211> LENGTH: 14
<212> TYPE: PRT
<213> ORGANISM: Artificial Sequence
<220> FEATURE:
<223> OTHER INFORMATION: SEQ ID NO:16

<400> SEQUENCE: 15

His Phe Glu Asp Trp Ile Asp His Phe Glu Asp Trp Ile Asp
1               5                   10

<210> SEQ ID NO 16
<211> LENGTH: 12
<212> TYPE: PRT
<213> ORGANISM: Artificial Sequence
<220> FEATURE:
<223> OTHER INFORMATION: Synthetic peptide

<400> SEQUENCE: 16

Met Arg Ala Ala Glu Ala Ala Ala Ala Glu Pro Met
1               5                   10

<210> SEQ ID NO 17
<211> LENGTH: 14
<212> TYPE: PRT
<213> ORGANISM: Artificial Sequence
<220> FEATURE:
<223> OTHER INFORMATION: Synthetic peptide

<400> SEQUENCE: 17

Val Tyr Val Ile Ile Asp Leu His Phe Glu Asp Trp Ile Asp
1               5                   10

<210> SEQ ID NO 18
<211> LENGTH: 13
<212> TYPE: PRT
<213> ORGANISM: Artificial Sequence
<220> FEATURE:
<223> OTHER INFORMATION: Synthetic peptide

<400> SEQUENCE: 18

Ser Ile Tyr Arg Arg Gly Ala Arg Arg Trp Arg Lys Leu
1               5                   10
```

-continued

<210> SEQ ID NO 19
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Modified with palmitoyl group

<400> SEQUENCE: 19

Phe Ala Arg Lys Gly Ala Arg Gln
1               5

<210> SEQ ID NO 20
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Modified with myristoyl group

<400> SEQUENCE: 20

Phe Ala Arg Lys Gly Ala Leu
1               5

<210> SEQ ID NO 21
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Modified with myristoyl group

<400> SEQUENCE: 21

Phe Ala Arg Lys Gly Ala Leu Arg Gln
1               5

<210> SEQ ID NO 22
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Modified with palmitoyl group

<400> SEQUENCE: 22

Phe Ala Arg Lys Gly Ala Leu Arg Gln
1               5

<210> SEQ ID NO 23
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Modified with myristoyl group -continued

```
<400> SEQUENCE: 23

Lys Arg Thr Leu Arg
1               5

<210> SEQ ID NO 24
<211> LENGTH: 17
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Modified with myristoyl group

<400> SEQUENCE: 24

Thr Arg Lys Arg Gln Arg Ala Met Arg Arg Val His Gln Ile Asn
1               5                   10                  15

Gly

<210> SEQ ID NO 25
<211> LENGTH: 13
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Modified with myristoyl group

<400> SEQUENCE: 25

Ser Ile Tyr Arg Arg Gly Ala Arg Arg Trp Arg Lys Leu
1               5                   10

<210> SEQ ID NO 26
<211> LENGTH: 5
<212> TYPE: PRT
<213> ORGANISM: Artificial Sequence
<220> FEATURE:
<223> OTHER INFORMATION: Synthetic peptide

<400> SEQUENCE: 26

Glu Ala Ala Ala Ala
1               5
```